US012207789B2

United States Patent
Lagow et al.

(10) Patent No.: US 12,207,789 B2
(45) Date of Patent: Jan. 28, 2025

(54) DISPOSABLE VALVE FOR AN ENDOSCOPE OPTIONALLY HAVING A LUBRICANT AND/OR AN ANTIMICROBIAL AGENT

(71) Applicant: Medivators Inc., Minneapolis, MN (US)

(72) Inventors: Robert Lagow, Shepard, TX (US); John Schreiner, St. Louis, MO (US); David C. Hemink, Minnetonka, MN (US)

(73) Assignee: Medivators Inc., Minneapolis, MN (US)

( * ) Notice: Subject to any disclaimer, the term of this patent is extended or adjusted under 35 U.S.C. 154(b) by 899 days.

(21) Appl. No.: 16/981,342

(22) PCT Filed: Mar. 19, 2019

(86) PCT No.: PCT/US2019/022841
§ 371 (c)(1),
(2) Date: Sep. 16, 2020

(87) PCT Pub. No.: WO2019/183013
PCT Pub. Date: Sep. 26, 2019

(65) Prior Publication Data
US 2021/0378487 A1 Dec. 9, 2021

Related U.S. Application Data

(60) Provisional application No. 62/645,951, filed on Mar. 21, 2018.

(51) Int. Cl.
*A61B 1/00* (2006.01)
*A61B 1/015* (2006.01)
*A61M 39/22* (2006.01)

(52) U.S. Cl.
CPC ........ *A61B 1/00068* (2013.01); *A61B 1/0011* (2013.01); *A61B 1/015* (2013.01);
(Continued)

(58) Field of Classification Search
CPC ............ A61M 39/22; A61M 2205/273; A61M 2039/224; A61M 2036/2466;
(Continued)

(56) References Cited

U.S. PATENT DOCUMENTS 4,261,343 A 4/1981 Ouchi et al.
4,325,362 A 4/1982 Ouchi et al.
(Continued)

FOREIGN PATENT DOCUMENTS

EP 0055394 3/1985
EP 1099393 A1 5/2001
(Continued)

OTHER PUBLICATIONS

Pentax Owner's Manual Pentax Video GI Scopes EG-290Kp, EC-380LKp, Nov. 2009.
(Continued)

*Primary Examiner* — Kelsey E Cary
(74) *Attorney, Agent, or Firm* — Sorell, Lenna & Schmidt, LLP

(57) ABSTRACT

A disposable valve assembly configured for use with an endoscope is disclosed. The disposable valve assembly may include a stem comprised of thermoplastic material, a spring stanchion configured to receive the stem and allow movement of the stem in an upward and downward position relative to the spring stanchion, a spring configured to contact that spring stanchion and the stem. In some embodiments, a lubricant is disposed on the stem, the spring stanchion and/or the spring. The disposable valve assembly may also include an antimicrobial agent disposed in the
(Continued)

lubricant, or in the thermoplastic material and/or can be coated thereon. A method for manufacturing the disposable valve assemblies for use with an endoscope may include several steps.

19 Claims, 37 Drawing Sheets

(52) U.S. Cl.
CPC ..... *A61M 39/22* (2013.01); *A61M 2205/0205* (2013.01); *A61M 2205/273* (2013.01)

(58) Field of Classification Search
CPC .................. A61M 1/00068; A61M 1/0011; A61M 1/015; A61M 1/00103; A61B 1/00068; A61B 1/0011; A61B 1/015
See application file for complete search history.

(56) References Cited

U.S. PATENT DOCUMENTS

| | | | |
|---|---|---|---|
| 4,361,138 A | 11/1982 | Kinoshita | |
| 4,402,310 A | 9/1983 | Kimura | |
| 4,561,428 A | 12/1985 | Konomura | |
| 4,800,869 A | 1/1989 | Nakajima | |
| D300,361 S | 3/1989 | Tokarz | |
| 4,844,052 A | 7/1989 | Iwakoshi et al. | |
| 4,852,551 A | 8/1989 | Opie et al. | |
| 4,900,305 A | 2/1990 | Smith | |
| 4,982,726 A | 1/1991 | Taira | |
| 5,127,909 A * | 7/1992 | Shichman | A61B 17/3498 604/272 |
| 5,386,817 A | 2/1995 | Jones | |
| 5,391,145 A | 2/1995 | Dorsey, III | |
| 5,522,796 A | 6/1996 | Dorsey, III | |
| 5,840,016 A | 11/1998 | Kitanao et al. | |
| 5,871,441 A * | 2/1999 | Ishiguro | A61B 1/122 600/159 |
| 5,876,326 A | 3/1999 | Takamura et al. | |
| 6,095,971 A | 8/2000 | Takahashi | |
| 6,132,369 A | 10/2000 | Takahashi | |
| 6,346,075 B1 | 2/2002 | Arai et al. | |
| 6,358,224 B1 | 3/2002 | Tims et al. | |
| 6,383,132 B1 | 5/2002 | Wimmer | |
| D473,646 S | 4/2003 | Baillargeon et al. | |
| D473,941 S | 4/2003 | Cise et al. | |
| 6,786,865 B2 | 9/2004 | Dhindsa | |
| 6,849,043 B2 | 2/2005 | Kondo | |
| 6,908,429 B2 | 6/2005 | Heimberger | |
| 7,220,226 B2 | 5/2007 | Rovegno | |
| D546,946 S | 7/2007 | Blake et al. | |
| D565,731 S | 4/2008 | Eisenkolb et al. | |
| 7,481,764 B2 | 1/2009 | Soutorine et al. | |
| 8,241,208 B2 | 8/2012 | Jiang et al. | |
| 8,568,303 B2 | 10/2013 | Yamane | |
| 8,821,389 B2 | 9/2014 | Yamane | |
| 9,125,550 B2 | 9/2015 | Shener-Irmakoglu et al. | |
| 9,144,374 B2 | 9/2015 | Maurice, Jr. | |
| 9,161,680 B2 | 10/2015 | Bellofatto et al. | |
| 9,247,862 B2 | 2/2016 | Shen et al. | |
| 9,307,890 B2 | 4/2016 | Ouchi | |
| D761,420 S | 7/2016 | Hayamizu | |
| 9,398,842 B2 | 7/2016 | Furuta | |
| 9,408,523 B2 | 8/2016 | Grudo et al. | |
| 11,589,738 B2 | 2/2023 | Anderson et al. | |
| 2003/0181905 A1 | 9/2003 | Long | |
| 2004/0238014 A1 | 12/2004 | Halstead et al. | |
| 2006/0041190 A1 | 2/2006 | Sato | |
| 2006/0100485 A1 | 5/2006 | Arai et al. | |
| 2006/0116552 A1 | 6/2006 | Noguchi et al. | |
| 2006/0135851 A1 | 6/2006 | Yamazaki | |
| 2006/0276689 A1 | 12/2006 | Litscher et al. | |
| 2007/0179432 A1 | 8/2007 | Bar Or et al. | |
| 2010/0240956 A1 | 9/2010 | Secrest et al. | |
| 2011/0298169 A1 | 12/2011 | Nguyen et al. | |
| 2012/0088975 A1 | 4/2012 | Morimoto | |
| 2012/0091092 A1 | 4/2012 | Adams et al. | |
| 2013/0138061 A1 * | 5/2013 | Yamane | A61B 1/015 604/319 |
| 2013/0303844 A1 | 11/2013 | Grudo et al. | |
| 2013/0338442 A1 | 12/2013 | Anderson et al. | |
| 2016/0058518 A1 | 3/2016 | Mason | |
| 2016/0120395 A1 | 5/2016 | Qi | |
| 2016/0143516 A1 | 5/2016 | Xu et al. | |
| 2016/0227984 A1 | 8/2016 | Hatano | |
| 2016/0309987 A1 | 10/2016 | Grudo et al. | |
| 2016/0331214 A1 | 11/2016 | Fujitani et al. | |
| 2016/0338577 A1 | 11/2016 | Viebach et al. | |

FOREIGN PATENT DOCUMENTS

| | | |
|---|---|---|
| EP | 000279039-0004 | 3/2005 |
| JP | 58-010031 A | 1/1983 |
| JP | S61-124602 A | 8/1986 |
| JP | S62-133929 A | 6/1987 |
| JP | 62-189041 A | 8/1987 |
| JP | H8-215137 A | 2/1995 |
| JP | 08238211 A | 9/1996 |
| JP | 08-266461 A | 10/1996 |
| JP | 09-122069 A | 5/1997 |
| JP | 1998-248791 A | 9/1998 |
| JP | H10-24879 A | 9/1998 |
| JP | 2000217777 A | 8/2000 |
| JP | 2001346761 A | 12/2001 |
| JP | 3828433 B2 | 10/2002 |
| JP | 2002306405 A | 10/2002 |
| JP | 2003-310542 A | 5/2003 |
| JP | 2004-169805 A | 6/2004 |
| JP | 2005261512 A | 9/2005 |
| JP | 2006-55447 A | 2/2006 |
| JP | 2006-175175 A | 7/2006 |
| JP | 2007075417 A | 3/2007 |
| JP | 2007-185276 A | 7/2007 |
| JP | 2004223121 A | 8/2007 |
| JP | 4242142 B | 3/2009 |
| JP | 4583915 B2 | 11/2010 |
| JP | 4589315 B | 11/2010 |
| JP | 2013523394 A | 6/2013 |
| JP | 2013545555 A | 12/2013 |
| JP | 2014133011 A | 7/2014 |
| WO | 2009-016352 A2 | 2/2009 |

OTHER PUBLICATIONS

Photos of Pentax OF-B120 Suction Control Valve, Pentax OF-B188 Air/Water Feeding Valve and Pentax OF-B121 Air/Water Valve, 2009.
Photos of Olympus Suction Valve MH-443 with parts separated, 2003.
Photos of Olympus Air/Water Valve MH-438 with parts separated, 2003.
Photo of Olympus suction valve MH-443 from internet website www.partsfinder.com, website visited Jan. 8, 2019 at https://www.partsfinder.com/parts/olympus-america-inc/MH443.
Photo of Olympus air/water valve MH-438 from internet website www.dotmed.com, website visited Jan. 8, 2019 at https://www.dotmed.com/listing/endoscope/olympus/mh-438/2101261.
Supplementary Partial European Search Report of the European Patent Office dated Nov. 22, 2016 and mailed on Dec. 2, 2016 of European Patent Application No. EP 11 84 5027 filed on Nov. 30, 2011.
Supplementary European Search Report dated Apr. 25, 2017 and mailed May 9, 2017 of European Patent Application No. EP 11 84 5027 filed on Nov. 30, 2011.
European Search Report of the European Searching Authority dated Mar. 15, 2016 of European Patent Application No. EP 11 84 5986 filed Nov. 30, 2011.
Olympus Operation Manual, dated 2003, 102 pages, entire document.

(56) References Cited

OTHER PUBLICATIONS

Third party submission filed on Jul. 17, 2014 in U.S. Appl. No. 13/989,573 (filing date Jul. 17, 2013).
Third party submission filed on Jul. 17, 2014 in U.S. Appl. No. 13/989,649 (filing date Jul. 17, 2013).
International Search Report and Written Opinion by the International Searching Authority Filed in Application No. PCT/US2011/062594 on Nov. 30, 2011 and mailed on Mar. 29, 2012.
JP3828433B2—Oct. 4, 2022—Yasuta Ishibiki—Google Patents English Translation.
JP08238211A—Sep. 17, 1996—Asahi Optical Co Ltd.—English Abstract Only.
JP08238211A—Sep. 17, 1996—Asahi Optical Co Ltd.—Google Patents English Translation.
JP2014133011A—Jul. 24, 2014—Hoya Corp—English Abstract Only.
JP2014133011A—Jul. 24, 2014—Hoya Corp—Google Patents English Translation.
JP2001346761A—Dec. 18, 2001—Asahi Optical Co Ltd.—English Abstract Only.
JP2001346761A—Dec. 18, 2001—Asahi Optical Co Ltd.—Google Patents English Translation.
End Definition and Meaning. Merriam-Webster Dictionary. Feb. 20, 2024. 9 pgs.
Reprocessing Summary and Guide for Fujinon/Fujifilm Flexible GI Endoscopes. Fujifilm Medical Systems USA Inc. Endoscopy Division. Wayne, NJ. Feb. 2018.
Olympus Reprocessing Manual / Instructions. 2009 Olympus Medical Systems Corp.
Fujifilm Endoscopes EG-L590ZW, EC-L590ZW/L Operation Manual (Cleaning, Disinfection and Storage). 2013 Fujifilm Corp.
Fujifilm Endoscope EC-600WL Operation Manual (Preparation and Operation). Fujifilm Corp. Jan. 2018.
Fujinon Electronic Video Endoscopes EVE 530/590 Series Operation Manual (Cleaning, Disinfection and Storage). Fujinon Corporation. Jan. 2015.
Pentax Owner's Manual Video GI Scopes EG-290Kp, EC-380MKp, EC-380MK2p, EC-380FKp, EC-380FK2p, EC-380LKp. Pentax Corporation. Nov. 2009.
Pentax Instructions for Use. Pentax Video GI Scopes 90i Series. Pentax Corp. Mar. 2014.
5.1 Preparing the equipment for reprocessing. Chapter 5: Reprocessing the Endoscope (and related reprocessing accessories). Olympus EVIS EXERA II TJF Type Q180V Reprocessing Manual. 2009.
Photo of Fuji and Olympus endoscope valves. Feb. 2016.

\* cited by examiner

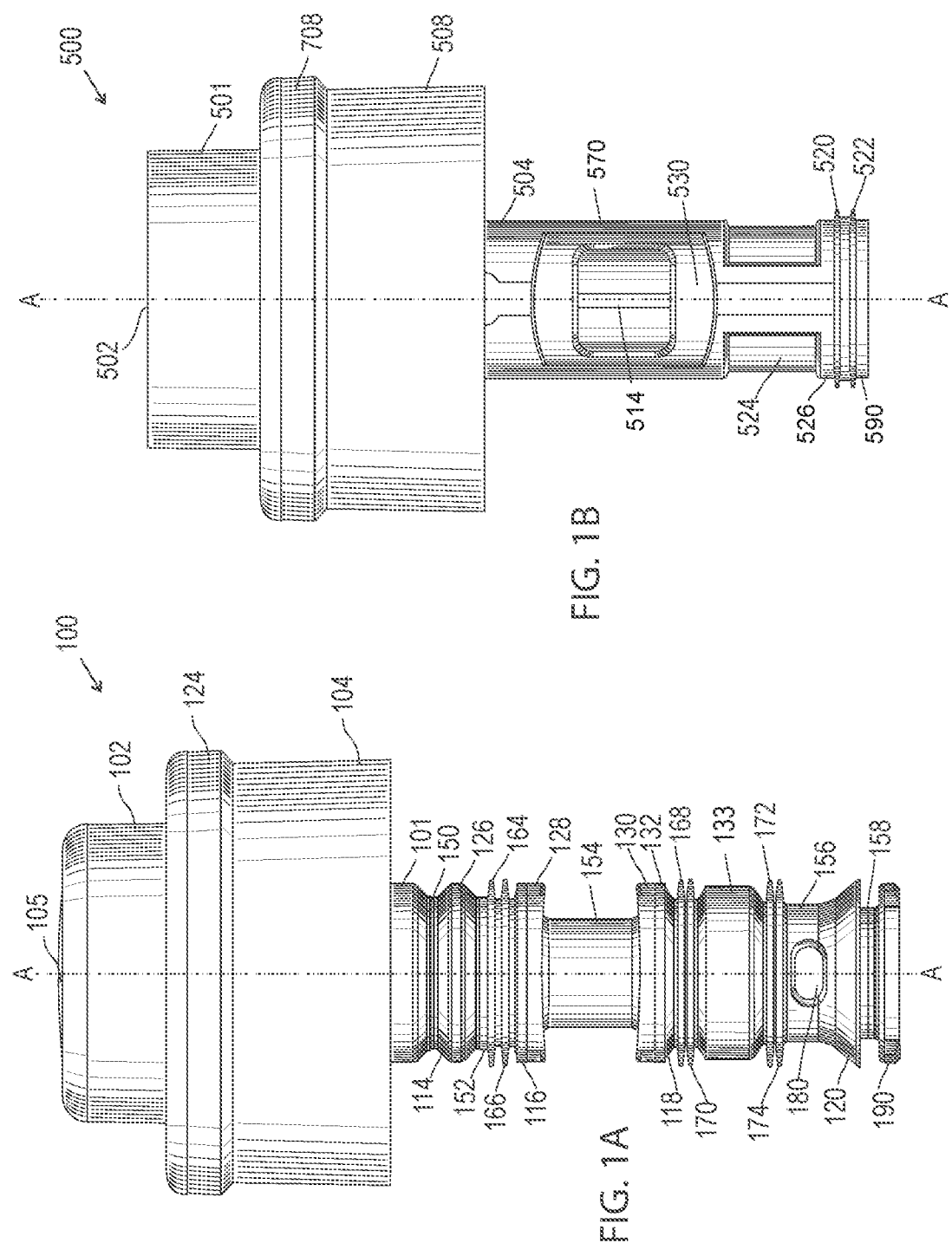

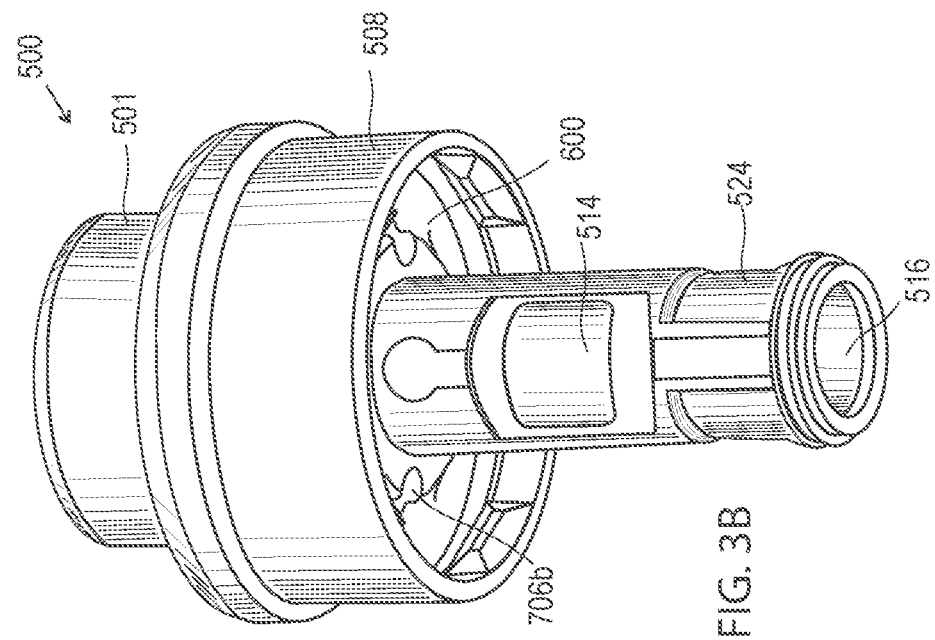
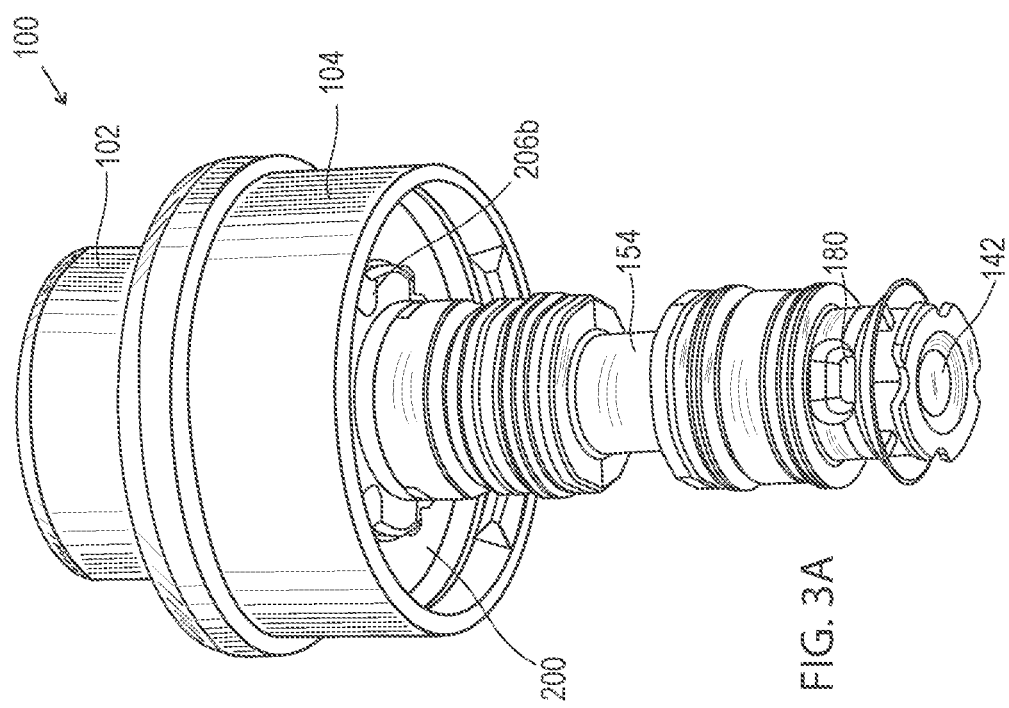

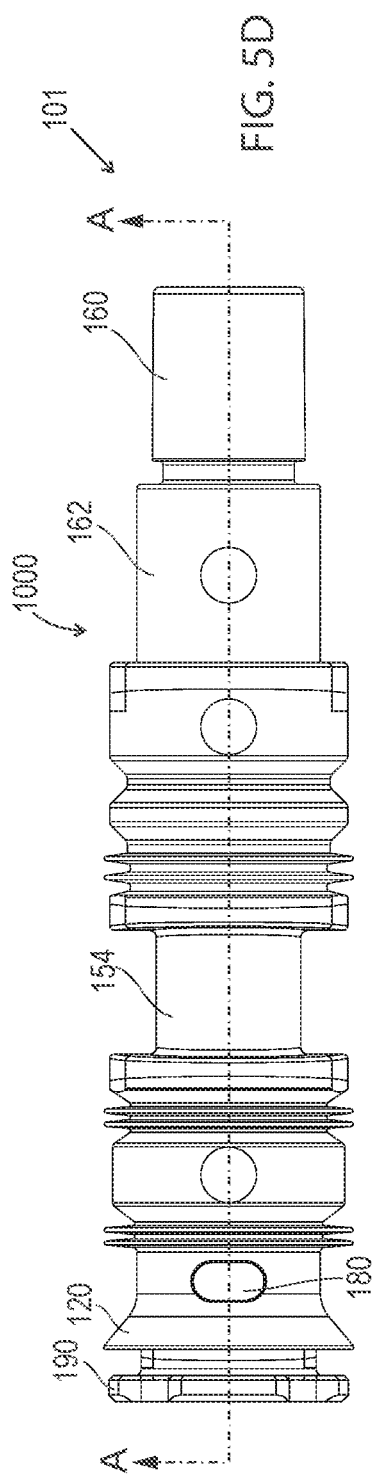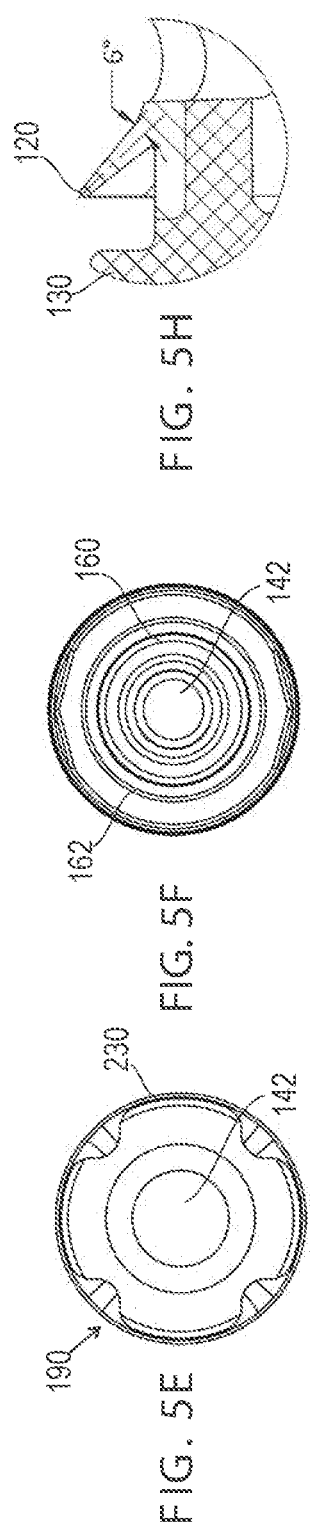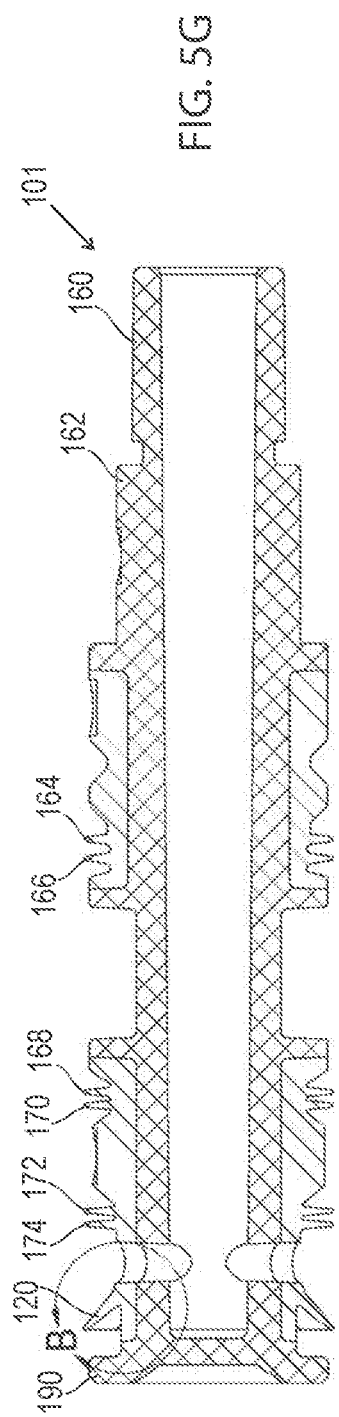

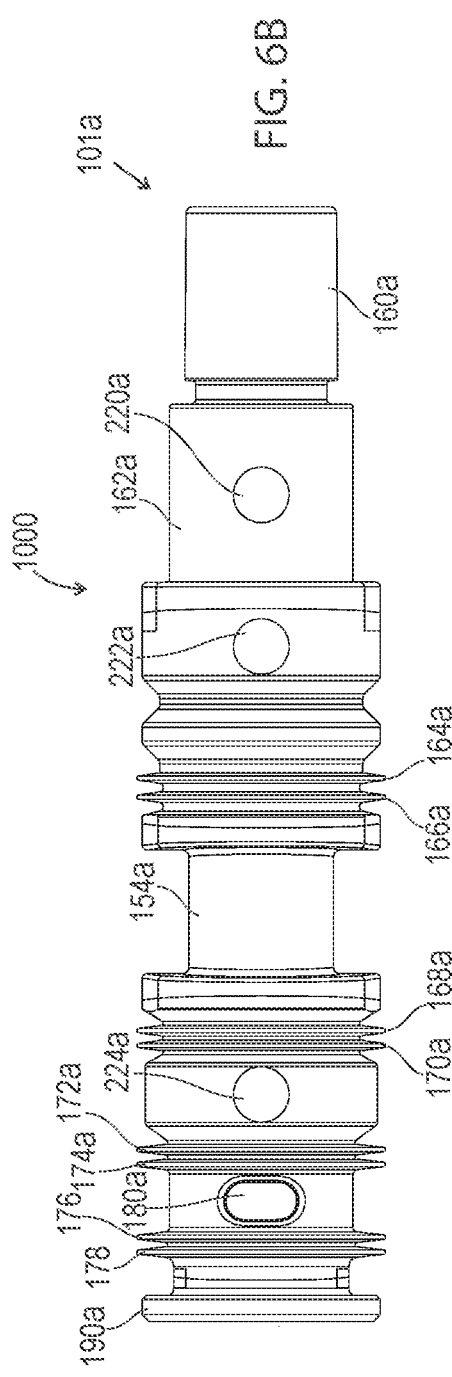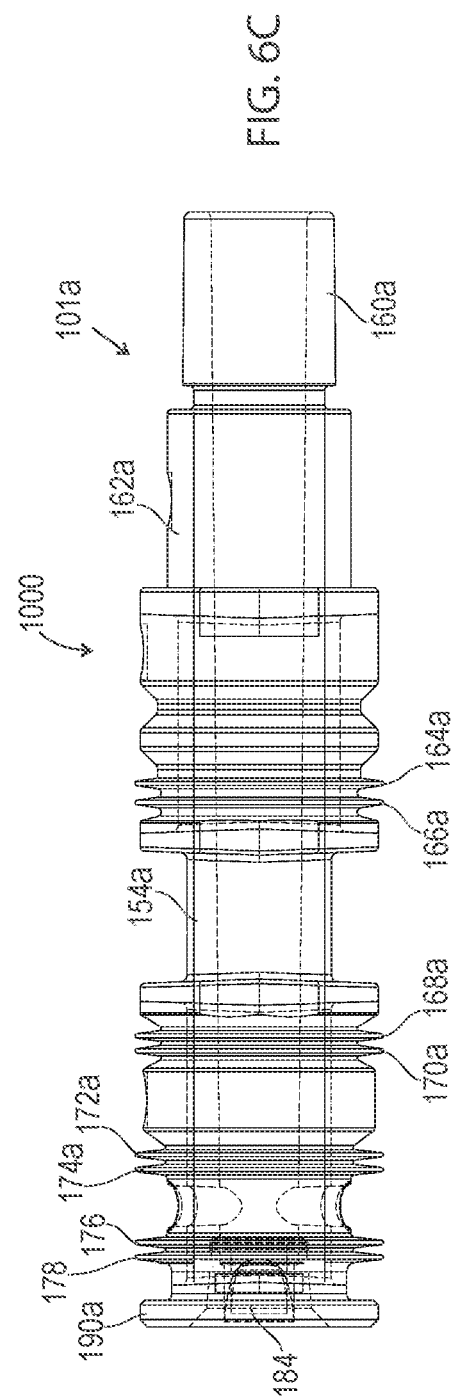

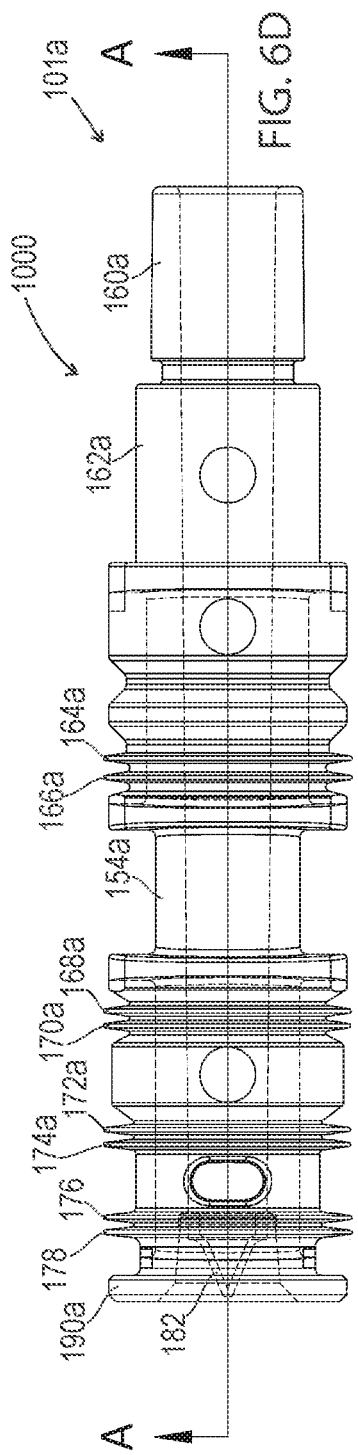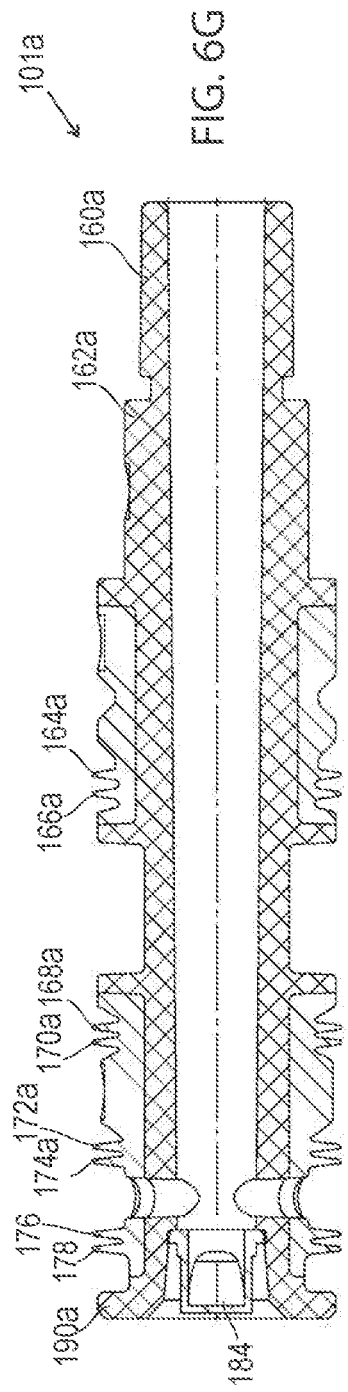
FIG. 6D
FIG. 6E
FIG. 6F
FIG. 6G

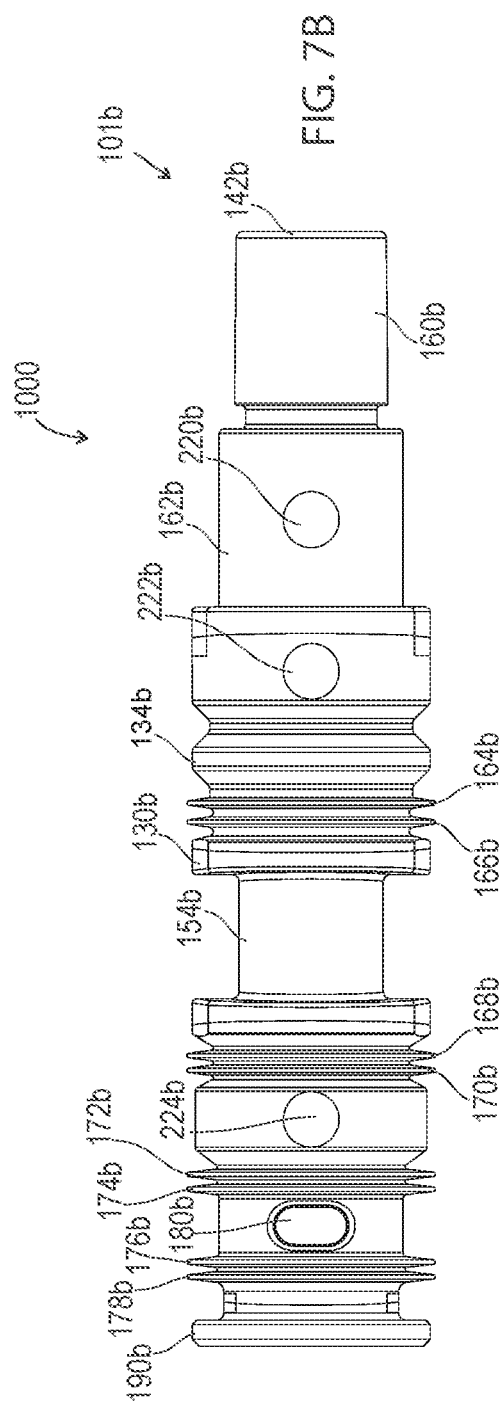
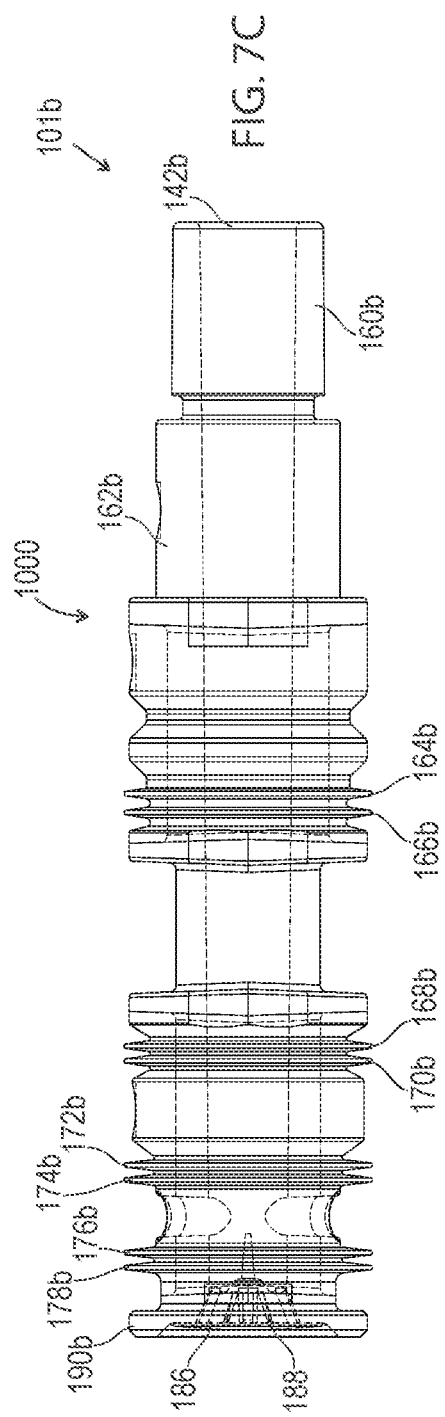

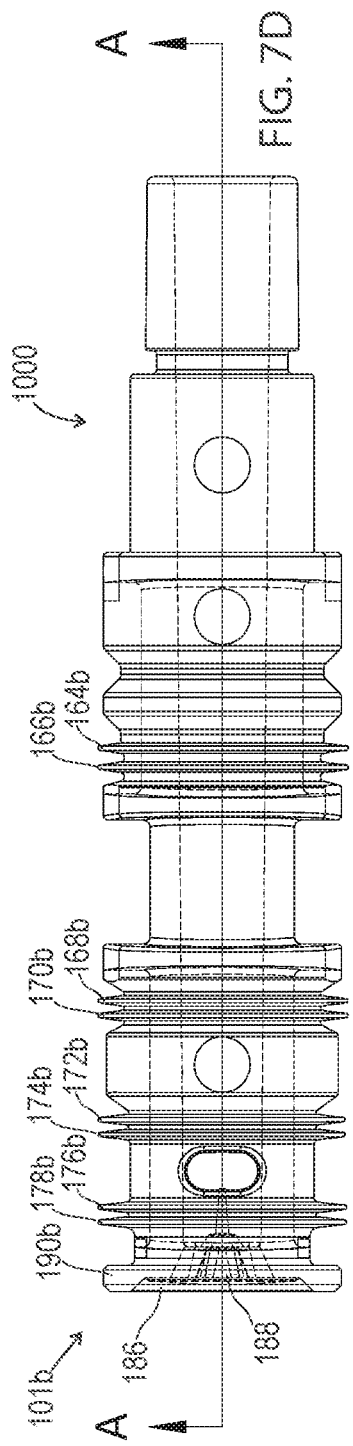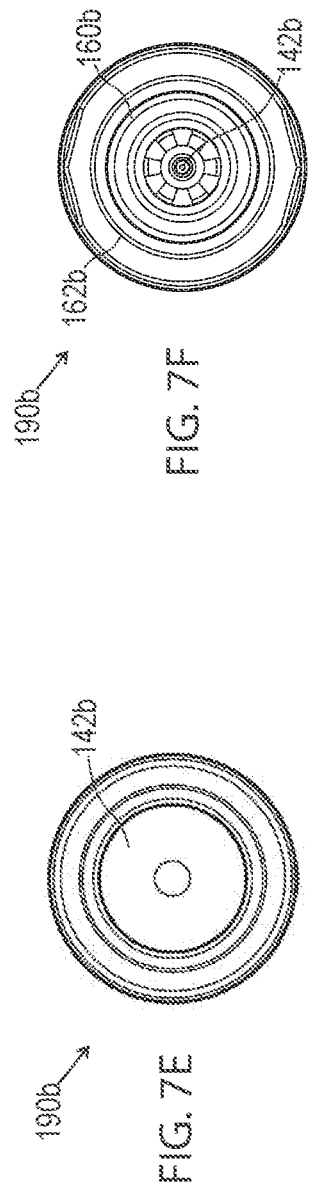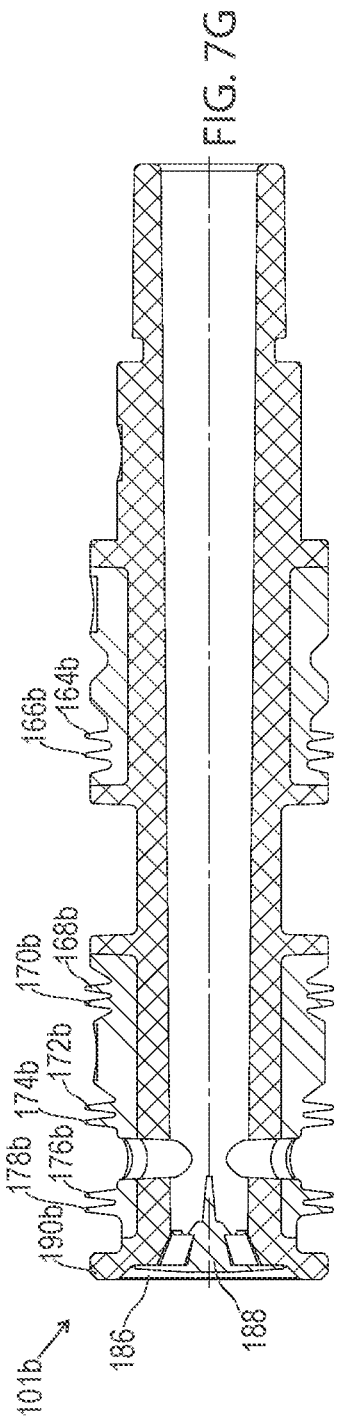

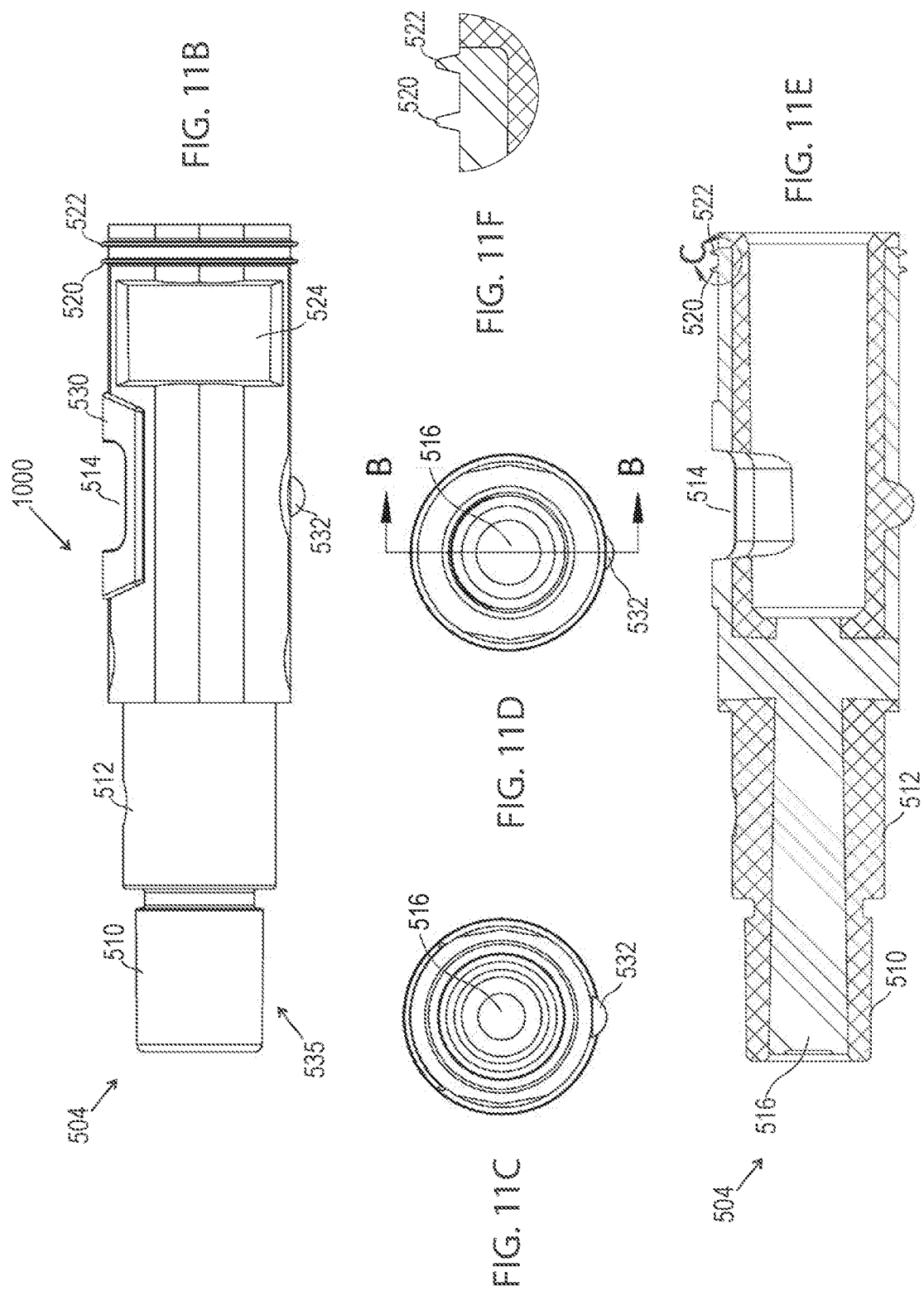

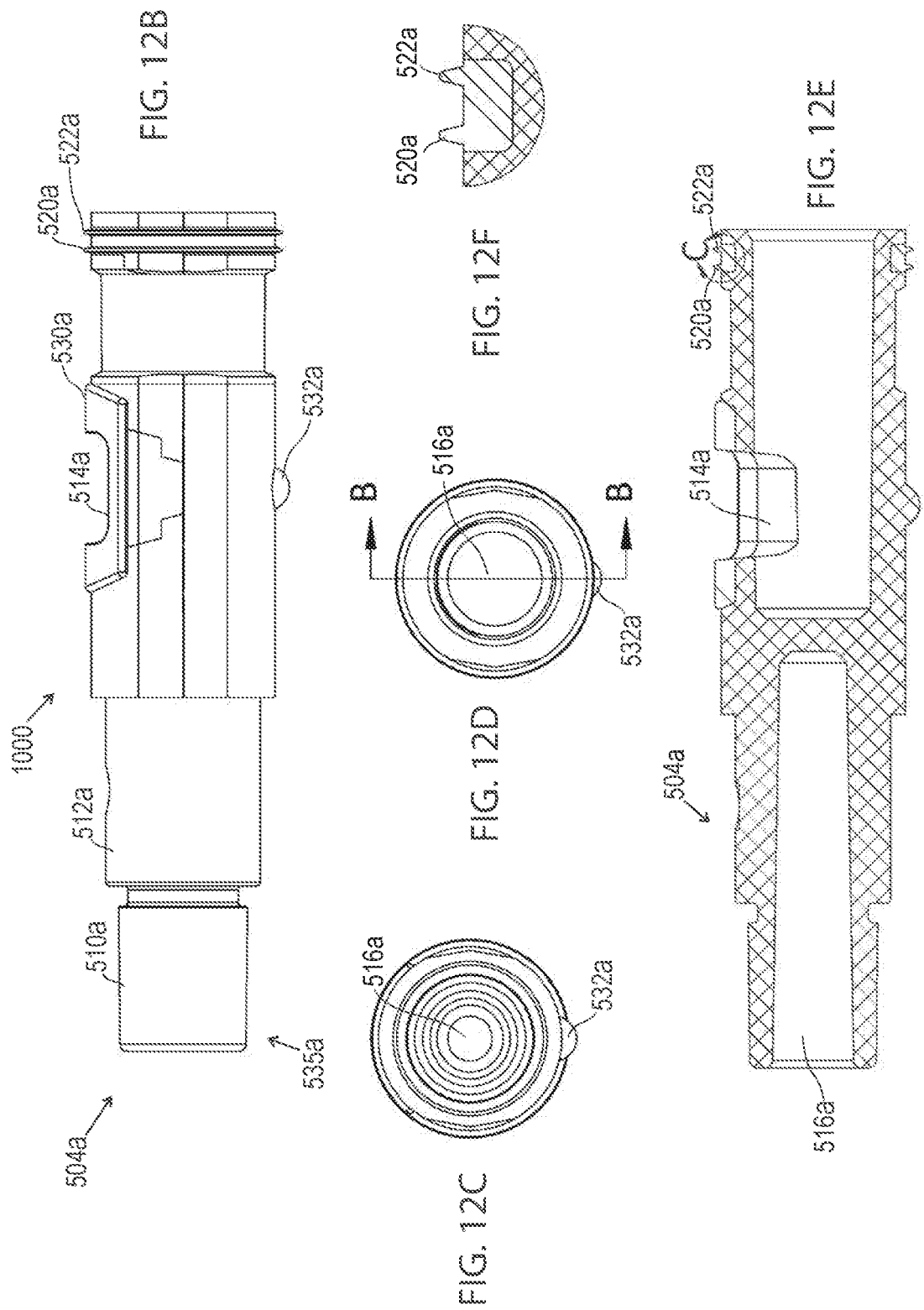

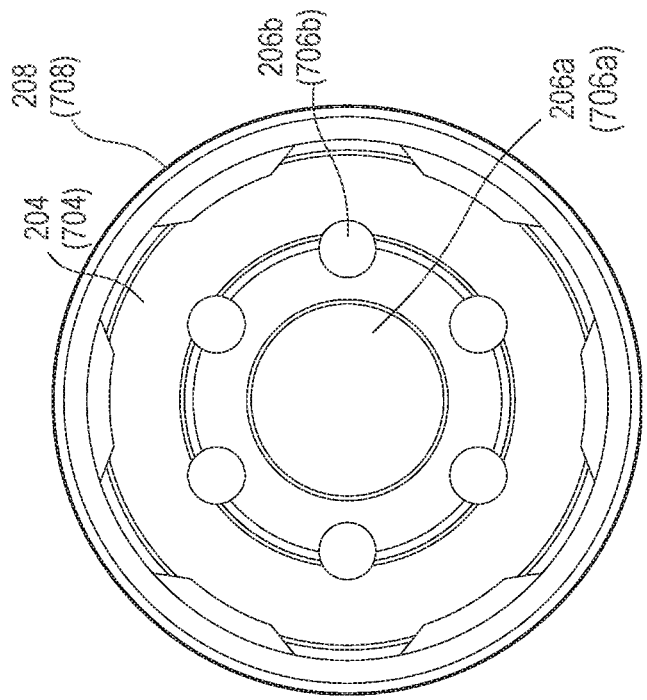
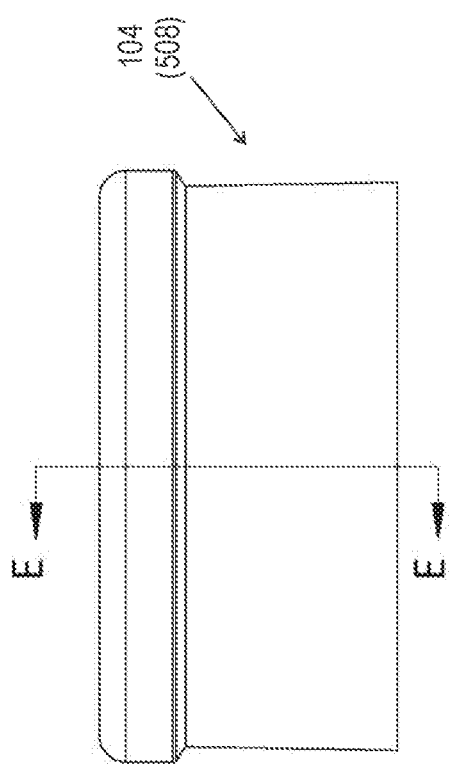
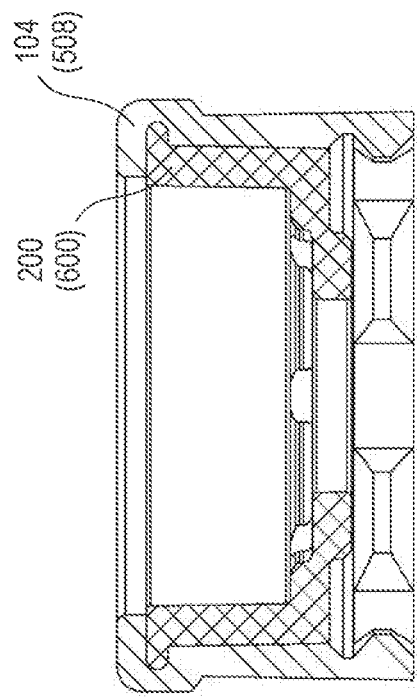
FIG. 15E
FIG. 15C
FIG. 15D

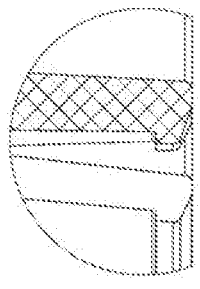
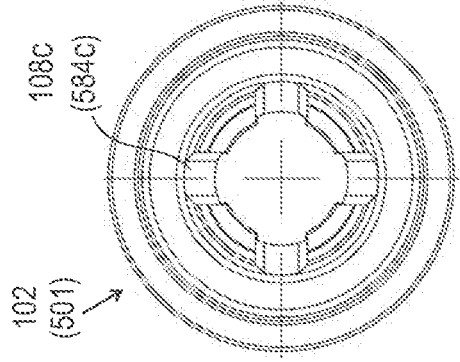
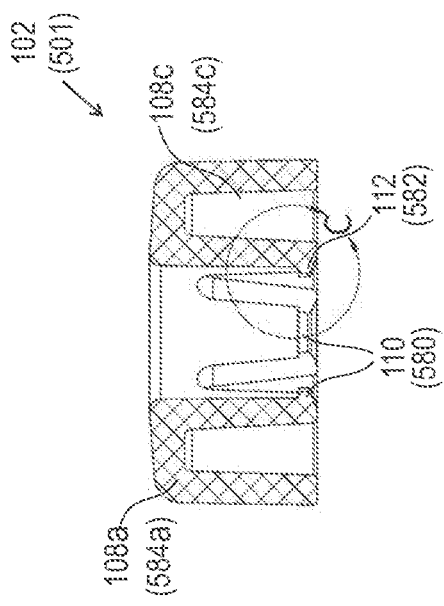
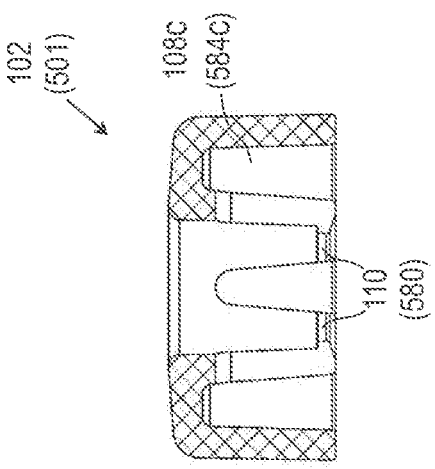
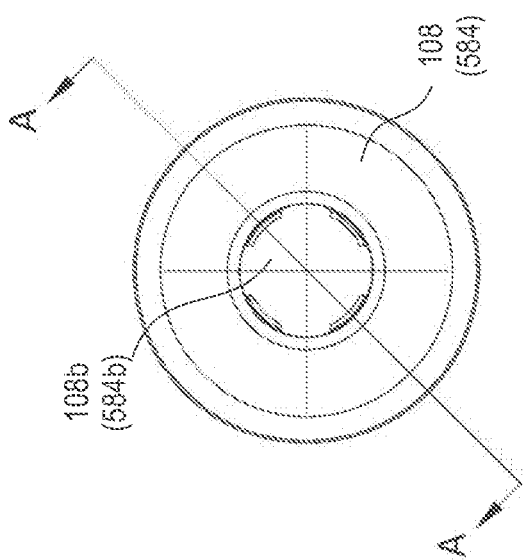
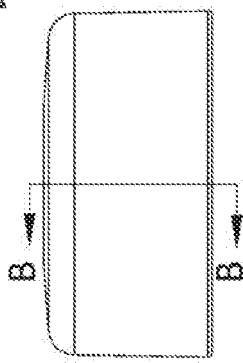

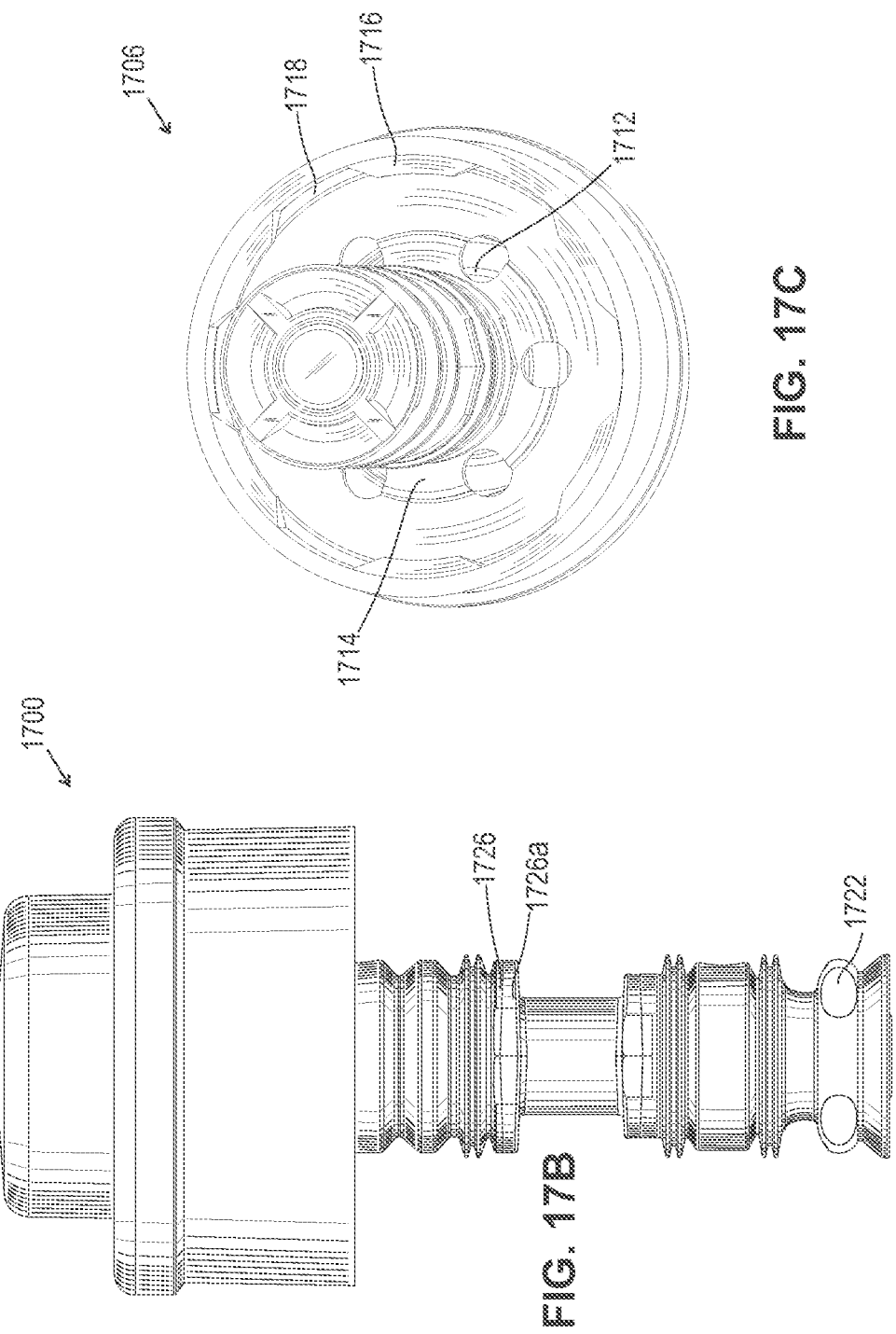

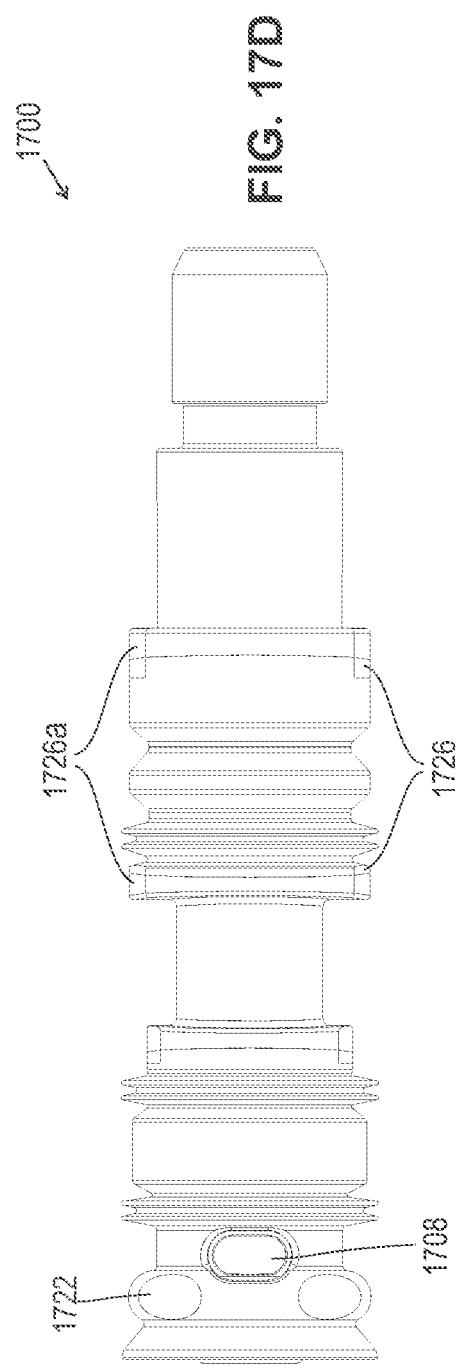

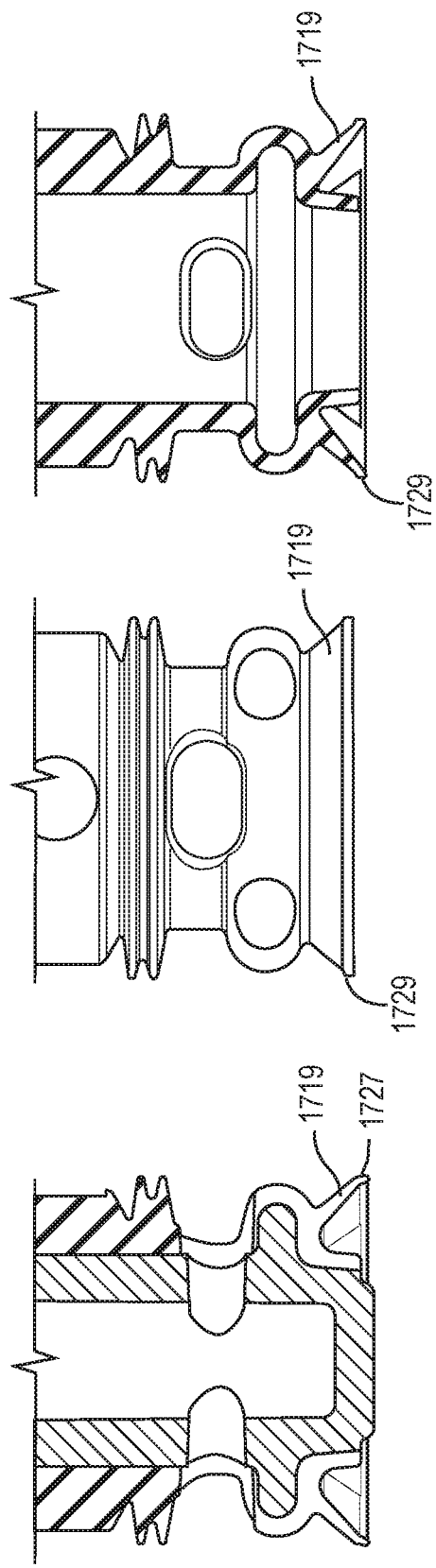

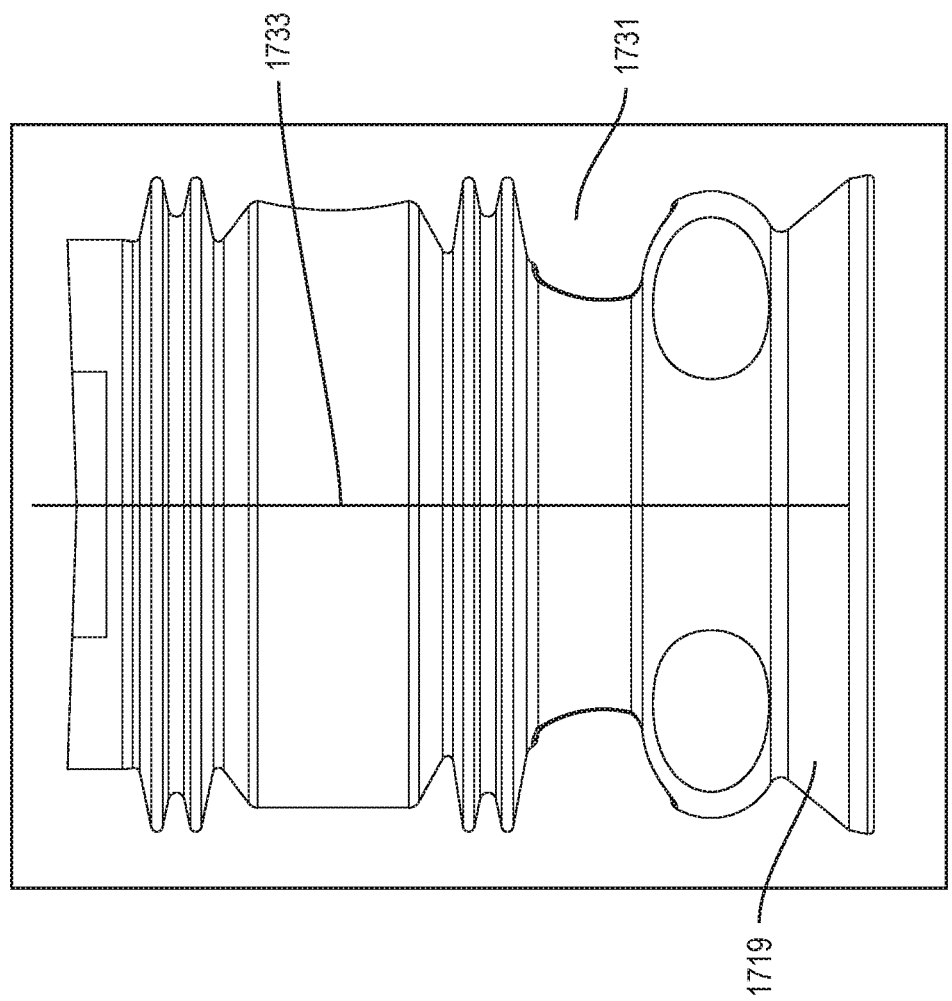

DISPOSABLE VALVE FOR AN ENDOSCOPE OPTIONALLY HAVING A LUBRICANT AND/OR AN ANTIMICROBIAL AGENT

PRIORITY CLAIM

This application claims priority to and the benefit of U.S. Provisional Application with Ser. No. 62/645,951, filed on Mar. 21, 2018, entitled DISPOSABLE VALVES FOR AN ENDOSCOPE OPTIONALLY HAVING LUBRICANT AND/OR AN ANTIMICROBIAL AGENT, which is herein incorporated by reference in its entirety.

BACKGROUND

Health care organizations are continually under pressure to find ways to lower or limit health care costs. One such opportunity for health care organizations to reduce costs is by recycling materials and supplies, in particular, by recovering single use medical devices (SUDs) that can be cleaned and sterilized for reuse.

Typically, medical devices fall into two categories. The first category is reusable devices, which are sold as reusable and can be cleaned and sterilized for reuse by a health care organization, such as a hospital. Reusable, manufacturer designated multiple-use medical devices are sold with the expectation that the medical devices can and will be processed for reuse by hospitals or surgery centers. Such medical devices are sold once and are typically cleaned and resterilized many times for use on multiple patients. These medical devices are collected after use by hospital or surgery center personnel and are cleaned, resterilized in an autoclave or by exposure to ethylene oxide or other appropriate sterilant, repackaged as necessary, and then reused.

The second category involves reprocessable devices, which are designated by the manufacturer for single use only; these medical devices can be reused only if properly reprocessed.

Among medical devices, endoscopes are well-known in the art and are commonly used for numerous medical procedures. A control section of an endoscope may include a suction cylinder, air/water cylinder, biopsy channels, and the like. Valves may be inserted into these cylinders or channels to control various functions of the endoscope.

After each use, an endoscope will undergo cleaning, disinfection, sterilization, and the like to prevent the spread of disease, germs, bacteria, and illness. Many components of an endoscope may be reusable, including valves which regulate the flow of air, water, or suction of fluids through the endoscope, and which must also be cleaned, disinfected, and/or sterilized between uses.

Unfortunately, there is usually a great expense associated with maintaining a high level of disinfection of the equipment and the reusable valves. Reusable endoscope valves must be carefully tracked together with the corresponding endoscope during cleaning and reprocessing procedures to identify breaches in reprocessing of the endoscope and its corresponding valves, which reduces the risk of cross-contamination among patients when endoscopes and their corresponding valves are reused.

Reusable valves may be assembled from the combination of several metal, plastic, and/or rubber components. As such, there are significant costs associated with the manufacturing of reusable valves for use with endoscopes.

Disposable valves eliminate the need for cleaning, disinfection, and sterilization of reusable valves, thereby eliminating the cost of repeated cleaning, disinfection, and sterilization. Disposable valves also eliminate the need to track valves to a specific endoscope model and serial number and provide the highest level of infection prevention to the patient. Additionally, disposable valves do not require expensive materials to be utilized in manufacture, thereby eliminating the high cost of manufacturing valves from expensive materials.

Thus, there is a need to develop new disposable valves for use with endoscopes that reduce or eliminate cross contamination and the need for repeated cleaning, disinfection, and sterilization. In particular, there is a need for new valves and methods that have the ability of preventing or substantially eliminating the growth of bacteria, fungi and the like during the endoscopic procedure.

SUMMARY

New disposable endoscope valves and methods are provided that reduce or eliminate the risk of contaminating the endoscope and reduce or eliminate the risk of infecting the patient. Further, new disposable endoscope valves and methods are provided that allow the disposable valve to function better by providing an improved seal using a lubricant that allows a more uniform fit in the valve chamber or channel and better suction, and/or flow of air and water. Various embodiments provide disposable valve assemblies configured for use with a FujiFilm™ endoscope and are discussed herein, including manufacturing processes for the same. The new disposable endoscope valves, in some embodiments, can have a lubricant. In addition to the lubricant or as an alternative to the lubricant, the disposable endoscope valves can have an antimicrobial agent disposed in the lubricant or coated on the disposable valve, or the antimicrobial can be made with the disposable valve and be integral with it.

In some embodiments, a disposable valve assembly is provided and may include a stem comprising, consisting essentially of or consisting of a proximal end and a distal end and a first opening disposed along a longitudinal axis of the stem and extending from the proximal end to or adjacent to the distal end of the stem, the stem comprising a second opening transverse to and intersecting with the first opening, the second opening of the stem adjacent to the distal end of the stem and extending through the stem. The stem comprises, consists essentially of, or consists of thermoplastic material. The valve assembly also includes a spring stanchion, the spring stanchion comprising an opening configured to receive the stem and allow movement of the stem in an upward and downward position relative to the spring stanchion. The valve assembly may also include a spring configured to contact the spring stanchion and the stem. In various embodiments, there is a lubricant disposed on the stem, spring stanchion and/or the spring. In some embodiments, (i) the lubricant comprises an antimicrobial agent; (ii) the thermoplastic material comprises an antimicrobial agent; and/or (iii) the thermoplastic material has an antimicrobial agent coated thereon.

In certain embodiments, there is a disposable valve assembly configured for use with a FujiFilm™ endoscope, the valve: (i) can be used to control air and water to the endoscope; (ii) has a lubricant disposed on the stem, spring stanchion and/or the spring; (iii) further comprises a cap, the cap configured to engage the stem; (iv) further comprises a cap having a fitting to snap fit with the stem; and/or (v) further comprises a boot having a diameter greater than the spring stanchion and configured to engage the spring stanchion. In some embodiments, the cap is ultrasonically welded, glued, screwed, snap-fitted or otherwise attached to the stem.

In certain implementations, the disposable valve assembly further comprises, consists essentially of or consists of an umbrella valve, a duckbill valve or a diaphragm valve disposed at the distal end of the stem. In other embodiments, (i) the duckbill or the diaphragm valve are press fit into a duckbill receptacle or a diaphragm receptacle and (ii) the umbrella valve can be over molded over the stem or otherwise attached to the stem.

In other implementations, the cap of the disposable valve assembly comprises a plurality of projections or, in some aspects, two projections, configured to receive a stem insert at one end and to snap fit onto the stem at the opposite end. In various aspects, (i) the lubricant of the disposable valve assembly comprises an antimicrobial agent; (ii) the thermoplastic material comprises an antimicrobial agent; and/or (iii) the thermoplastic material has an antimicrobial agent coated thereon.

In various implementations, (i) the lubricant of the disposable air/water valve assembly comprises silicone-based grease, non-silicone based grease, or a combination thereof; and/or (ii) the antimicrobial agent is an antibiotic, an antiseptic, an antiviral agent, an antifungal agent, a disinfectant or a combination thereof.

In certain embodiments, this disclosure provides a disposable suction valve assembly configured for use with an endoscope. The disposable suction valve assembly comprises a stem, comprising a proximal end and a distal end and a first opening disposed along a longitudinal axis of the stem, the stem comprising a thermoplastic material and a second opening transverse to and intersecting with the first opening, the second opening of the stem partially extending through the stem and a surface opposite the second opening comprising a projection extending from the stem. The disposable suction valve assembly also includes a spring stanchion comprising an opening configured to receive the stem, the spring stanchion configured to allow movement of the stem in an upward and downward position relative to the spring stanchion; and a spring configured to contact the spring stanchion.

In other implementations, (i) the disposable valve assembly is used to suction to and from the endoscope; (ii) a lubricant is disposed on the stem, spring stanchion and/or the spring; (iii) the disposable valve assembly further comprises a cap, the cap configured to engage the stem; (iv) the disposable valve assembly further comprises a cap having a fitting to snap fit with the stem; (v) the disposable valve assembly further comprises a boot having a diameter greater than the spring stanchion and configured to engage the spring stanchion; or (vi) the projection has a semicircular shape for aligning the disposable valve assembly with the endoscope.

In certain aspects, the second opening of the stem, which partially extends through the stem, further comprises a gasket contiguous with the second opening and having a raised surface or protrusion, the gasket providing better alignment of the valve assembly with the endoscope to create an air/fluid-tight seal. In other implementations, the cap of the disposable valve assembly comprises a plurality of projections or, in some aspects, 2, 3, 4, 5, 6, 7, or other even or odd numbers of projections, configured to receive a stem insert at one end and to snap fit onto the stem at the opposite end. In various aspects, (i) the lubricant of the disposable valve assembly comprises an antimicrobial agent; (ii) the thermoplastic material comprises an antimicrobial agent; and/or (iii) the thermoplastic material has an antimicrobial agent coated thereon.

In various implementations, (i) the lubricant of the disposable suction valve assembly comprises silicone-based grease, non-silicone-based grease, or a combination thereof; and/or (ii) the antimicrobial agent is an antibiotic, an antiseptic, an antiviral agent, an antifungal agent, a disinfectant or a combination thereof.

In various embodiments, this disclosure provides a method for manufacturing an air/water disposable valve assembly configured for use with an endoscope, the method comprising separately molding the valve stem, cap and spring stanchion, wherein the stem comprises a proximal end and a distal end and a first opening disposed along a longitudinal axis of the stem and extending from the proximal end to or adjacent to the distal end of the stem, the stem comprising a second opening transverse to and intersecting with the first opening, the second opening of the stem adjacent to the distal end of the stem and extending through the stem.

In other embodiments, the proximal end of the stem can be placed through the center of a spring; the proximal end of the stem is then placed through a stem opening in the spring stanchion; the cap can be attached onto the proximal end of the stem and secured with a stem insert; and a lubricant is applied onto the stem, spring and/or spring stanchion. In other aspects, the method of manufacturing further comprises, consists essentially of or consists of (i) over molding gaskets on the stem; (ii) over molding a boot onto the spring stanchion; or (iii) disposing an umbrella valve, a duckbill valve or a diaphragm valve at the distal end of the stem. In other implementations, the method of manufacturing also includes steps wherein (i) the stem of the air/water valve is color coded; (ii) the stem comprises gaskets to assure an air-tight seal within a suction port or the stem; (iii) molding of the stem is optionally in the presence of an antimicrobial; (iv) the button cap is ultrasonically welded, press fit or otherwise attached to the stem; (v) the lubricant comprises a silicone-based grease, non-silicone based grease, or a combination thereof; and/or (vi) the antimicrobial agent is an antibiotic, an antiseptic, an antiviral agent, an antifungal agent, a disinfectant or a combination thereof.

In some embodiments, a method is provided for manufacturing a disposable suction valve assembly for use with an endoscope and may include several steps. A stem is precision molded optionally in the presence of an antimicrobial agent, then placed in a mold for over molding gaskets or seals onto the stem. Prior to the next steps, the stanchion and button cap are molded. The boot can be over molded onto the stanchion. The back or proximal end of the stem is placed through the center of the stanchion/boot and resilient member (e.g., spring, rubber, elastic, etc.). The button cap is then placed on and secured to the stem. A lubricant may be applied onto the stem, spring and/or spring stanchion.

In some embodiments, a spring stanchion is molded; a bottom end of the stem is placed through the center of a spring; a bottom end of the stem is placed through a stem opening in the spring stanchion; and a lubricant is applied onto the stem, spring, and/or spring stanchion and the lubricant, in other embodiments, includes an antimicrobial agent.

In other embodiments, a method for manufacturing a disposable suction valve configured for use with an endoscope is provided, the method comprising: separately molding the valve stem, cap and spring stanchion, wherein the stem comprises a proximal end and a distal end and a first opening disposed along a longitudinal axis of the stem, the stem comprising a second opening transverse to and intersecting with the first opening, the second opening of the stem partially extending through the stem and a surface opposite the second opening comprising a projection extending from the stem; placing the proximal end of the stem through the center of a spring; placing the proximal end of the stem through a stem opening in the spring stanchion; attaching the cap onto the proximal end of the stem and securing with a stem insert; and applying a lubricant onto the stem, spring and/or spring stanchion.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIGS. 1A and 1B illustrate front views of an embodiment of a disposable air/water valve and a suction valve, respectively;

FIGS. 2A, 2B, 3A, 3B, 4A, 4B illustrate perspective views of an embodiment of a disposable air/water valve and a suction valve, respectively;

FIGS. 5B and 5D illustrate side views of the umbrella stem design of an embodiment of a disposable air/water valve for use in endoscopes and FIG. 5C illustrates a cross-sectional view of the umbrella stem design of an embodiment of a disposable air/water valve for use in endoscopes;

FIG. 5E illustrates a bottom view of the distal end of the umbrella stem design of an embodiment of a disposable air/water valve for use in endoscopes;

FIG. 5F illustrates a top view of the proximal end of an embodiment of the umbrella stem design of a disposable air/water valve for use in endoscopes;

FIG. 5G illustrates a cross-sectional view of the umbrella stem design of an embodiment of a disposable air/water valve along plane AA of FIG. 5D.

FIG. 5H illustrates an enlarged view of detail B of FIG. 5G;

FIGS. 6C and 6D illustrate cross-sectional views of the duckbill stem design of an embodiment of a disposable air/water valve suitable for use in endoscopes, and FIG. 6B illustrates a side view of the duckbill stem design of an embodiment of a disposable air/water valve suitable for use in endoscopes;

FIG. 6E illustrates a bottom view of the distal end of the duckbill stem design of an embodiment of a disposable air/water valve for use in endoscopes;

FIG. 6F illustrates a top view of the proximal end of the duckbill stem design of an embodiment of a disposable air/water valve for use in endoscopes;

FIG. 6G illustrates a cross-sectional view of the duckbill stem design of an embodiment of a disposable air/water valve along plane AA of FIG. 6D for use in endoscopes;

FIG. 7B illustrates a side view of the diaphragm stem design of an embodiment of a disposable air/water valve suitable for use in endoscopes;

FIGS. 7C and 7D illustrate cross-sectional views of the diaphragm stem design of an embodiment of a disposable air/water valve suitable for use in endoscopes;

FIG. 7E illustrates a bottom view of the distal end of the diaphragm stem design of an embodiment of a disposable air/water valve for use in endoscopes;

FIG. 7F illustrates a top view of the proximal end of the diaphragm stem design of an embodiment of a disposable air/water valve for use in endoscopes;

FIG. 7G illustrates a cross-sectional view of the diaphragm stem design of an embodiment of a disposable air/water valve along plane AA of FIG. 7D for use in endoscopes;

FIG. 11B illustrates a side view of the stem of an embodiment of a disposable suction valve suitable for use in endoscopes;

FIG. 11C illustrates a top view of the proximal end of the stem of an embodiment of a disposable suction valve for use in endoscopes;

FIG. 11D illustrate a bottom view of the distal end of the stem of an embodiment of a disposable suction valve for use in endoscopes;

FIG. 11E illustrates a cross-sectional view of the stem of an embodiment of a disposable suction valve along plane BB of FIG. 11D for use in endoscopes;

FIG. 11F is an enlarged view of detail C of FIG. 11E;

FIG. 12B illustrates a side view of the stem of an embodiment of a disposable suction valve suitable for use in endoscopes;

FIG. 12C illustrates a top view of the proximal end of the stem of an embodiment of a disposable suction valve for use in endoscopes;

FIG. 12D illustrate a bottom view of the distal end of the stem of an embodiment of a disposable suction valve for use in endoscopes;

FIG. 12E illustrates a cross-sectional view of the stem of an embodiment of a disposable suction valve along plane BB of FIG. 12D for use in endoscopes;

FIG. 12F is an enlarged view of detail C of FIG. 12E;

FIG. 15C illustrates a side view of an embodiment of a boot of a disposable air/water or a disposable suction valve suitable for use in endoscopes;

FIG. 15D illustrates a cross-sectional view of the boot of an embodiment of a disposable air/water or a disposable suction valve suitable for use with endoscopes along axis EE of FIG. 15C;

FIG. 15E illustrates a top view of an embodiment of a boot of a disposable suction valve suitable for use with endoscopes;

FIG. 16B illustrates a top view of an embodiment of a cap snap for use with a disposable air/water or a disposable suction valve;

FIG. 16C illustrates a cross-sectional view along axis AA of FIG. 16B for use with a disposable air/water or a disposable suction valve;

FIG. 16D is an enlarged view of detail C of FIG. 16C;

FIG. 16E illustrates a side view of an embodiment of a cap snap for use with a disposable air/water or a disposable suction valve;

FIG. 16F illustrates a cross-sectional view along plane BB of FIG. 16E; and

FIGS. 16G and 16H illustrate embodiments of a bottom view of cap snap for use with a disposable air/water or a disposable suction valve.

FIG. 17B illustrates a side view of an embodiment of a disposable air/water valve for use in endoscopes;

FIG. 17C illustrates a bottom view of an embodiment of a disposable air/water valve for use in endoscopes;

FIG. 17D illustrates a side view of the stem of an embodiment of a disposable air/water valve for use in endoscopes;

FIG. 17F illustrates a partial cross sectional side view of components of an embodiment of a disposable air/water valve for use in endoscopes;

FIG. 17G illustrates a partial side view of components of an embodiment of a disposable air/water valve for use in endoscopes;

FIG. 17H illustrates a partial cross sectional side view of components of an embodiment of a disposable air/water valve for use in endoscopes;

FIG. 17K illustrates a side view of components of an embodiment of a disposable air/water valve for use in endoscopes disposed in a mold during manufacturing.

Figure 2B:
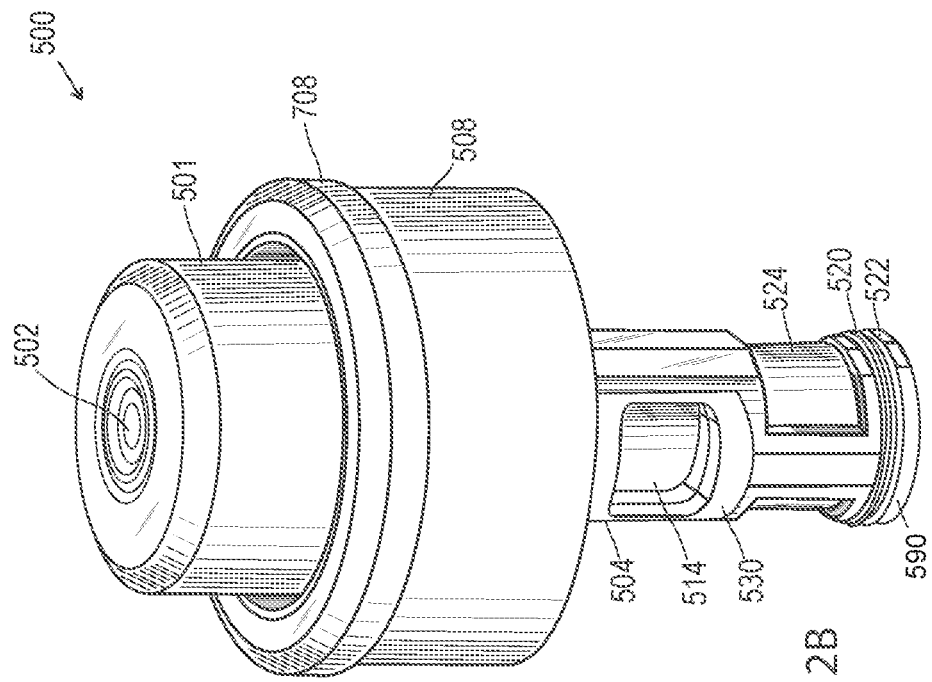
Figure 2A:
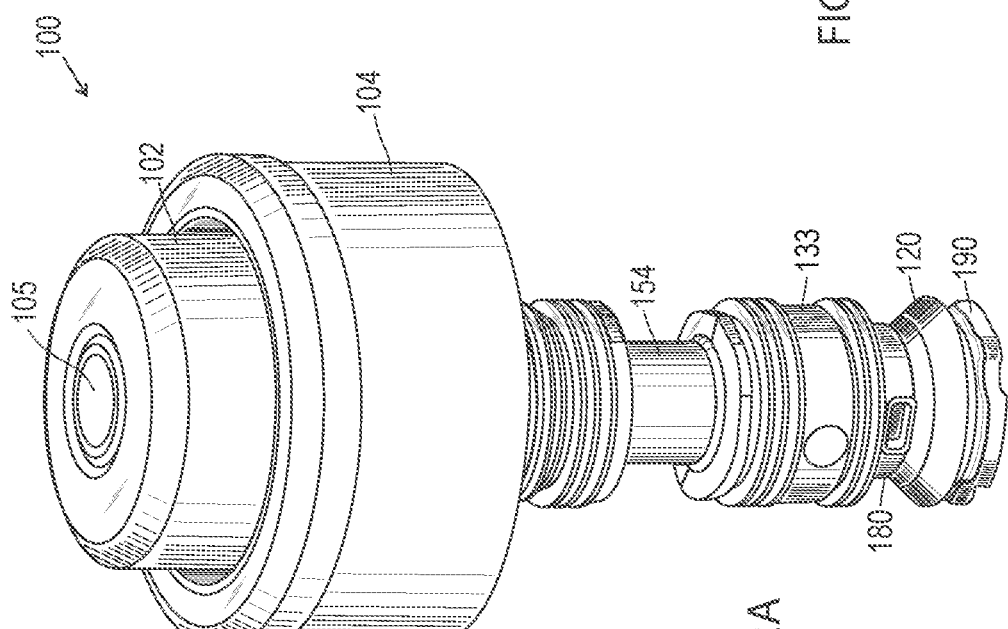

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

For the purposes of this disclosure, the phrase "effective amount" or "therapeutically effective amount" is defined as a dosage sufficient to induce a microbicidal or microbiostatic effect upon the microbes contacted by the composition on a surface.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an" and "the" include plural referents unless expressly and unequivocally limited to one referent. Thus, for example, reference to "a seal" includes one, two, three or more seals.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

Disposable Valve Assembly for Use with an Endoscope

New disposable endoscope valves and methods are provided that reduce or eliminate the risk of contaminating the endoscope and reduce or eliminate the risk of infecting the patient. New disposable endoscope valves and methods are provided that allow the disposable valve to function better by providing an improved seal. In some embodiments, the disposable valve comprises a lubricant that allows a more uniform fit in the valve chamber or channel and better suction and/or flow of air and water. Various embodiments of disposable valve assemblies configured for use with endoscopes are discussed herein, including manufacturing processes for the same. The new disposable endoscope valves, in some embodiments have a lubricant or as an alternative to the lubricant, can have an antimicrobial agent disposed in the lubricant or coated on the disposable valve or the antimicrobial can be made with the disposable valve and be integral with it.

In certain embodiments, the present disclosure provides a disposable valve assembly configured for use with an endoscope comprising: a stem comprising a first opening disposed along a longitudinal axis of the stem; a spring stanchion; the spring stanchion comprising an opening configured to receive the stem and allow movement of the stem in an upward and downward position relative to the spring stanchion; a spring configured to contact the spring stanchion and the stem; and a lubricant disposed in at least one of the stem, spring stanchion or the spring. In other embodiments, the disposable valve assembly configured for use with an endoscope does not contain a lubricant and instead, it contains an antimicrobial agent disposed in at least one of the stem, spring stanchion or the spring. In other embodiments, the valve assembly, can contain a lubricant, and/or can further comprise an antimicrobial agent in (i) a molding of the valve assembly, (ii) a coating disposed in at least one of the stem, spring stanchion or the spring of the valve assembly, or (iii) the lubricant or a combination thereof.

In various embodiments, in the disposable valve assemblies described in this disclosure, (i) the lubricant can comprise a silicone-based grease, a non-silicone based grease, or a combination thereof and/or (ii) the antimicrobial agent is an antibiotic, an antiseptic, an antiviral agent, an antifungal agent, a disinfectant, silane, or a combination thereof. In various embodiments, the antimicrobial agent comprises minocycline, gendine, genlenol, genlosan, genfoctol, aminoglycosides, beta lactams, quinolones, fluoroquinolones, macrolides, sulfonamides, sulfamethaxozoles, tetracyclines, streptogramins, oxazolidinones (linezolid), clindamycins, lincomycins, rifamycins, glycopeptides, polymyxins, lipopeptide antibiotics, pharmacologically acceptable sodium salts, pharmacologically acceptable calcium salts, pharmacologically acceptable potassium salts, and lipid formulations.

In other embodiments, the disposable valve assembly described in this disclosure further comprises a boot configured to be attached to the spring stanchion and the stem, the boot configured to contact the stem when the stem is moved in a downward position; a stem insert disposed in the first opening of the stem, the stem insert configured to prevent air passage out of the first opening, wherein the lubricant disposed in at least one of the stem, the spring stanchion, the spring, the stem insert or the boot. In yet other embodiments, the stem further comprises a second opening, the second opening disposed transverse to the first opening, the first and second openings are for allowing passage of air and/or fluid, wherein the opening in the spring stanchion is disposed in a center of the spring stanchion and the spring stanchion comprises a ledge to receive a first end of the spring and the stem comprises a ledge to receive the second end of the spring.

In certain embodiments, (i) the stem has a proximal end, the stem further comprising a plurality of ridges and grooves disposed circumferentially about the stem, the plurality of ridges and grooves being monolithic with the stem, a plurality of seals disposed in the grooves of the stem and the stem comprising a first opening disposed at the proximal end and running along a longitudinal axis of the stem; a retainer ring contacting and disposed around the stem; a button head or button cap contacting the proximal end of the stem and a resilient member contacting the retainer ring and the button head or button cap, wherein application of a downward force to the button head or button cap causes the stem to move in a downward position; (ii) the stanchion, a boot, and/or a button cap are attached to the proximal end of the stem and a resilient member contacts the stanchion, boot and/or button cap, wherein movement of the resilient member in a downward direction moves the stem in a downward position; or (iii) the stanchion comprises a diaphragm and portion that contacts the resilient member, the stanchion disposed in the center of the stem, the resilient member comprising a spring that contacts the stanchion and the button cap and the button cap is disposed at the proximal end of the stem.

In other aspects, (i) the spring stanchion further comprises at least one recess and/or projection configured to attach to the stem, the stem being movable in a downward position on application of a downward pressing force; or (ii) wherein the at least one recess and/or projection of the spring stanchion comprises a cutout configured to lock the stem to the spring stanchion.

In certain embodiments, in the disposable antimicrobial valve assembly described in this disclosure, (i) the stem comprises a plurality of points at one end, and a top portion or a button head at an opposite end configured to be contacted by a finger; (ii) the stem comprises a projection comprising a sealing member to assure a proper seal within a suction port of a medical device; (iii) the stem comprises an O-ring attached thereto to assure a proper seal within a suction port of the endoscope; or (iv) wherein the stem, and spring stanchion comprise thermoplastic material. In other embodiments, (i) the first opening of the stem contacts the second opening of the stem, and when the stem is pressed in a downward direction, the second opening aligns with a suction channel of the endoscope and allows passage of air and/or fluid to a suction connection.

In yet other embodiments, in the disposable valve assembly described in this disclosure, (i) the stem comprises a thermoplastic material, and a second opening disposed transverse to the first opening, the first and second openings intersecting with each other and configured to allow passage of air and/or fluid through at least a portion of the stem and the first and second openings intersect with each other; and/or (ii) the button cap comprises a vent running into the first opening of the stem.

Disposable Air/Water Valves

FIGS. 1A and 1B are front views of illustrative implementations of disposable air/water and suction valves for use with endoscopes. FIGS. 2A, 2B, 3A, 3B, 4A and 4B are perspective views of disposable air/water and suction valves for use with endoscopes.

Figure 5A:
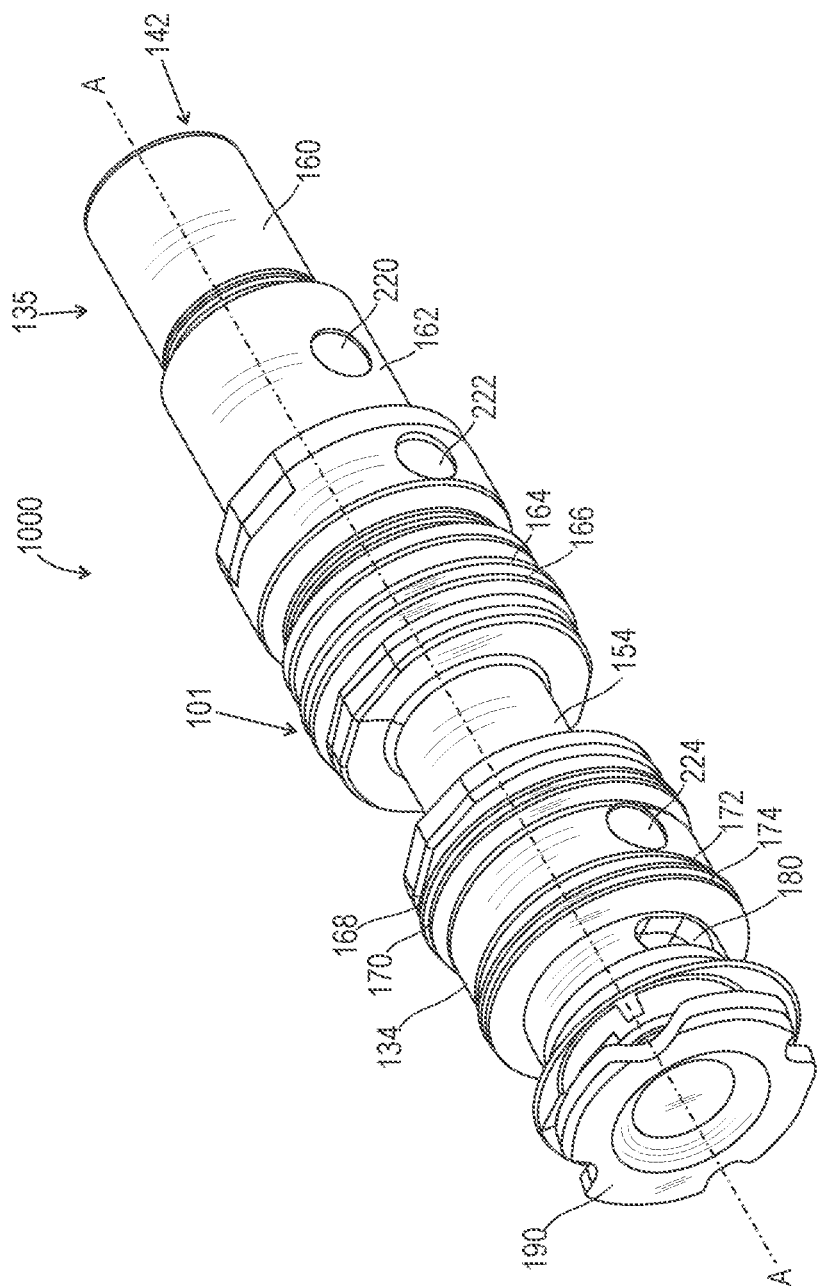
FIG. 5A illustrates a perspective view of an umbrella stem design of an embodiment of a disposable air/water valve suitable for use in endoscopes.
Figure 6A:
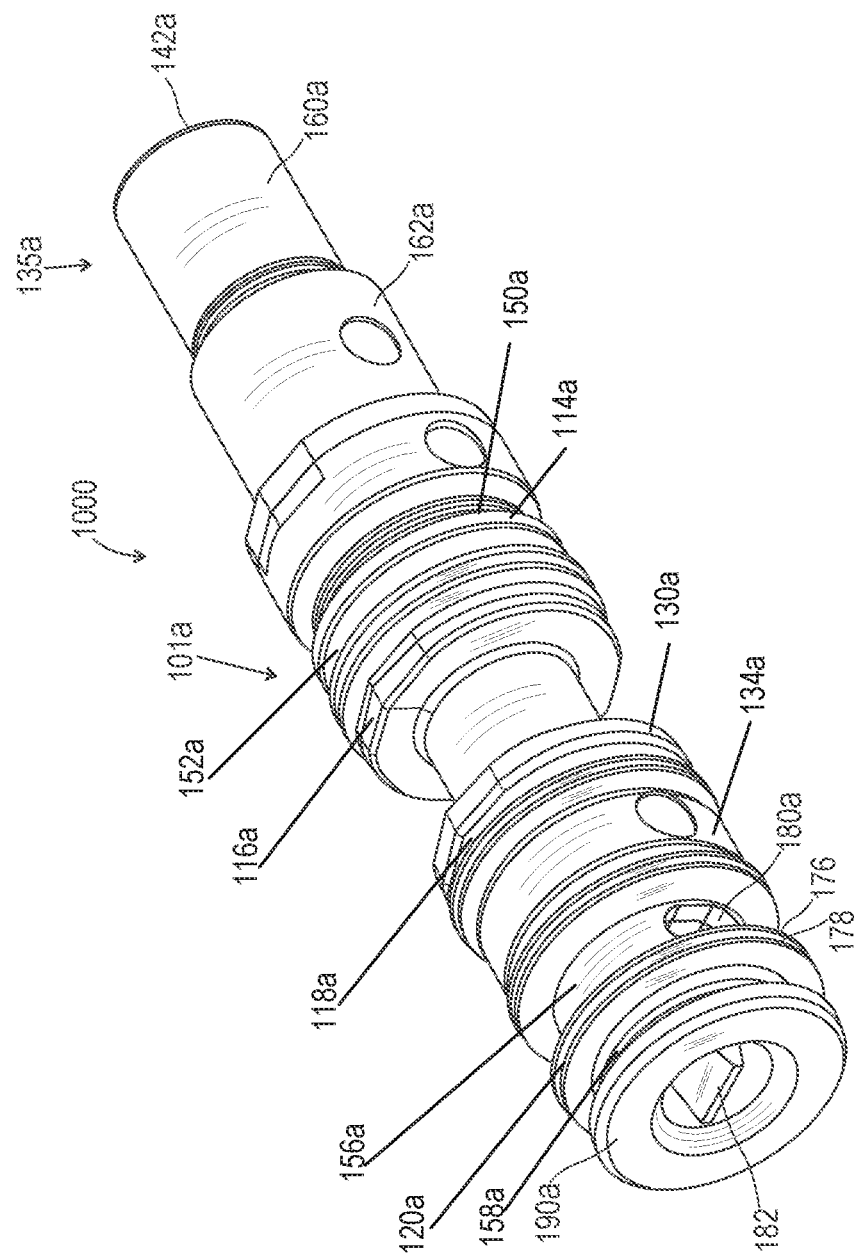
FIG. 6A illustrates a perspective view of a duckbill stem design of another embodiment of a disposable air/water valve for use in endoscopes.
Figure 7A:
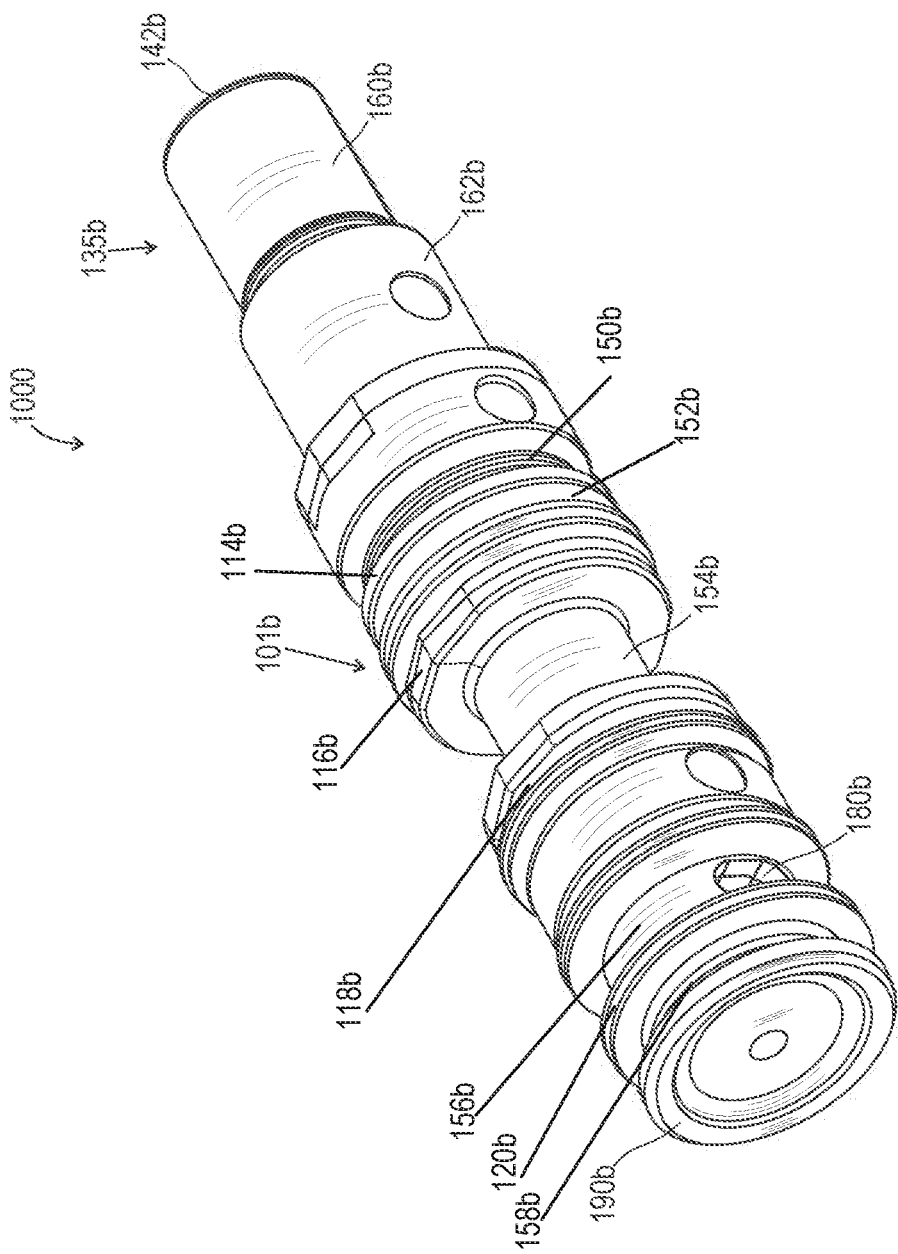
FIG. 7A illustrates a perspective view of a diaphragm stem design of another embodiment of a disposable air/water valve for use in endoscopes.

With reference to FIGS. 1A, 2A, 3A and 4A, disposable air/water valve 100 has as main components, all positioned along longitudinal axis AA, main stem 101, button head or cap 102, boot 104, resilient member or spring (not shown) and gaskets or seals 164, 166, 168, 170, 172, 174. An example of the resilient member is shown as a spring in 412 of FIG. 9A. Because there are several implementations of the air/water valve, in this application, identical elements will be referenced in parenthesis. Moreover, reference to one element applies equally to all identical air/water disposable valve elements. With reference to FIGS. 5A, 6A and 7A, main stem 101 (101a, 101b) is monolithic (e.g., a single piece). Stem 101 has gasket surfaces 150, 152 and 156, and grooves 154, 158, 160 and 162 that are molded as part of the stem and proximal end 135 positioned about opening end 142. In other implementations, main stems 101a and 101b are also monolithic and have gasket surfaces 150a, 152a, 156a, grooves 154a, 158a, 160a, 162a, gasket surfaces 150b, 152b, 156b, and grooves 154b, 158b, 160b and 162b. Main stems 101a and 101b have gaskets 164a, 166a, 168a, 170a, 172a, 174a, 176b, 178b, 164b, 166b, 168b, 170b, 172b, 174b. In some embodiments, the gaskets provide mini seals for better air/water control. The stem of the disposable suction valve shown in FIG. 1B can have an opening 514 that is transverse to the main stem. The opening 514 is disposed in the mi-section 570 of the main stem. Adjacent groove 524 is surface 526, which is adjacent gaskets or seals 520 and 522 at end rim 590 of the disposable valve.

The disposable air/water valve 100 also contains aligners 114, 116, 118 and 190 (114a, 116a, 118a, 120a, 114b, 116b, 118b, 190b). Stem 101 (101a, 101b) further contains a transverse hole 180 (180a, 180b). These ridges and/or grooves can be rigid or they can be flexible. In the embodiments shown, due to the ridges and/or grooves the main stem has a varied diameter, where the diameter is greater by the ridges and the diameter is smaller by the grooves. This configuration allows gaskets or seals to be inserted or overmolded into the grooves.

Unlike the non-disposable air/water valves that are not monolithic as many of the ridges and/or grooves are fabricated separately and contain different material than the stem, which often comprises metal, the monolithic stem (one piece) of the disposable air/water valve comprises a plurality of ridges and grooves that can be the same material as the stem. In some embodiments, gaskets or seals 164-178 can be set into the grooves of stem 101.

One or more components of the device of the current application (e.g., gaskets or seals 164-178 (164a-178a, 164b-178b), stem 101 (101a, 101b), stanchion 200, boot 104, resilient member (e.g., spring, rubber, elastic, etc.) (not shown) and button cap 102 can be made from a suitable material such as for example, thermoplastic material. An example of the resilient member is shown as a spring in 412 of FIG. 9A.

Suitable materials include, but are not limited to, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. FIGS. 1A to 7G, 15A to 16G also illustrate lubricant 1000 which may be disposed on valve 100 or at least on stem 101 (101a, 101b). Lubricant 1000 can also be disposed on the stanchion or spring stanchion 200 and spring. In some embodiments, lubricant 1000 also contains an antimicrobial agent. In some embodiments, disposable air/water valve 100 can contain the antimicrobial as part of the stem, spring stanchion, seal, and/or spring. The antimicrobial agent can be a coating on the components or homogenously disposed in the material that the stem, spring stanchion, seal, and/or spring is made from.

Stem 101 (101a, 101b) is precision molded in one piece for accuracy and rigidity. Stem 101 (101a, 101b) may be color coded to identify the product as an air/water valve. Color coding of stem 101 allows the air/water valve to be easily identified. Further, the color coding also identifies the disposable air/water valve as a disposable valve. In some embodiments, color coding can identify which endoscopes certain parts are compatible with. Stem 101 provides several gasket, gasket surfaces or seal retaining regions or grooves 150-158 for keeping gaskets or seals 164-178 (FIG. 1A to 7G) in desired positions on stem 101. Stem 101 (101a, 101b) also contains a proximal end 135 (135a, 135b) positioned about opening end 142 (142a, 142b). At proximal end 135, stem 101 contains a first opening 142. Ridges 124, 126, 128, 130, 132, 133, and 190 like the retaining regions or grooves, are molded as part of the stem 101. Gaskets or seals 164-178 of FIGS. 1A to 7G may be over-molded to stem 101 (101a, 101b) or appropriately otherwise secured to the stem 101 (101a, 101b). Over-molding the seals on the stem avoids the need to slide the seals onto stem 101, which could tear or damage the seals during assembly. Operation of an air/water valve in an endoscope is discussed in further detail below.

FIGS. 5A, 6A and 7A are perspective illustrations of different implementations of disposable air/water valves 100 for use with endoscopes. FIGS. 5B-5H, 6B-6G and 7B-7G are cross-sectional, bottom, top and detail views of air/water valves 100. While in all implementations, the air/water valves contain gaskets, in valve 100, disc and/or gasket 120 is shaped as an umbrella valve. In stem 101a, duckbill valve 182 is configured to be received within disc 190a and in stem 101b, diaphragm valve is received within disc 190b.

Umbrella shaped gasket 120 is an elastomeric valve component that is an umbrella shaped sealing disc. This elastomeric component can be used as a sealing element in a backflow prevention device such as a valve. When mounted in a seat, the convex umbrella shaped disc 120 flattens out against the valve seat and absorbs a certain amount of seat irregularities and creates a certain sealing force. The umbrella shaped sealing disc will allow forward flow once the head pressure creates enough force to lift the convex diaphragm from the seat and so it will allow flow at a predetermined pressure in one way and prevent back flow immediately in the opposite way.

Figure 5B:
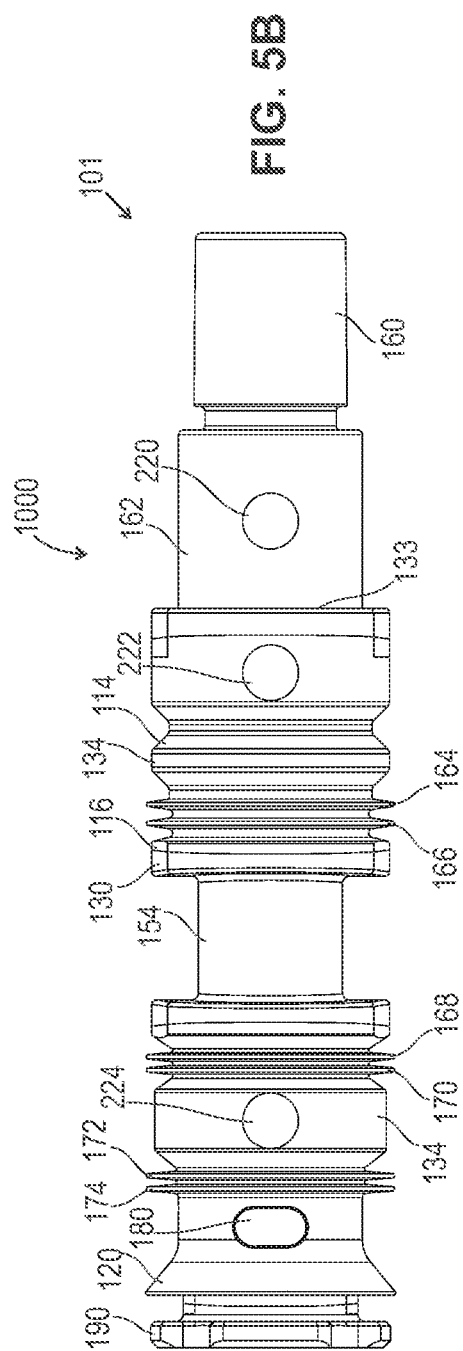
Figure 5C:
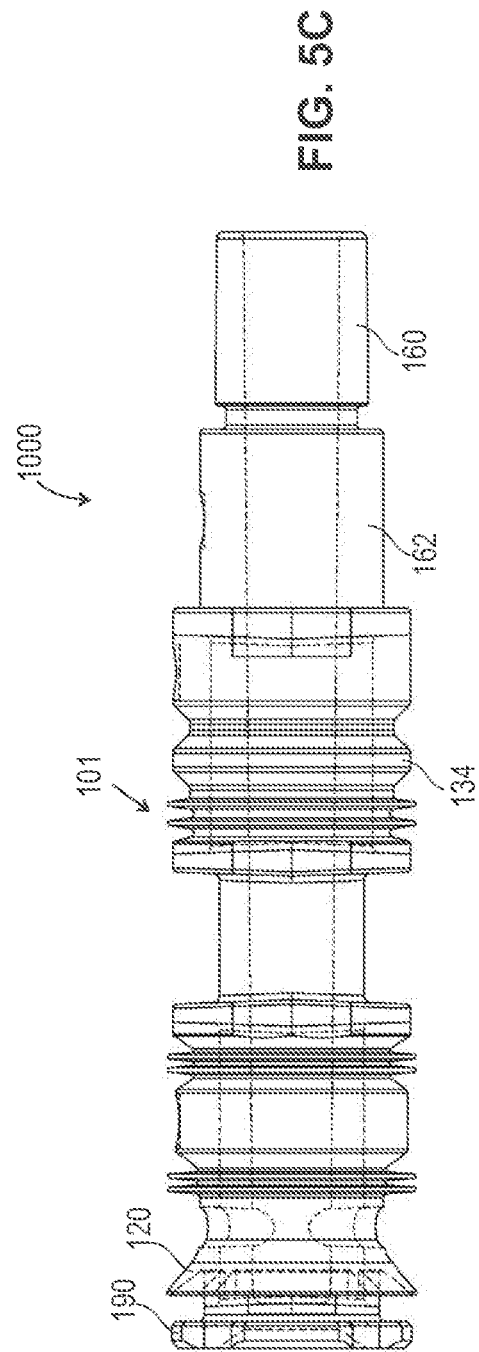

FIGS. 5B and 5D are side views of the stem of the air/water valve. FIG. 5C is a view of stem 101 illustrating a groove 154, aligners 114, 130, 172 and 190, gaskets 164, 166, 168, 170, 172 and 174, ridges 116, 118 and 134, and transverse hole 180. Cutouts 220, 222 and 224 are valve gates through which the flow of plastic (for example, polycarbonate) can be more accurately controlled whenever stem 101 is prepared by injection molding. In some embodiments, cutouts are ejector pin marks. FIGS. 5E, 5G and 5H illustrate more details regarding umbrella shaped disc 120. FIG. 5E is a bottom view of the distal end of stem 101 illustrating detail 230 of the umbrella disc 120. FIG. 5G is a cross-sectional view of stem 101 along AA plane of FIG. 5D. FIG. 5H provides an enlarged view of detail B of FIG. 5G. Detail B illustrates the position of disc 120 with respect to aligner 190. In some embodiments, gasket 120 is at about 140° with respect to the stem's axis and the gasket 120 has a taper of about 6°. The resulting design in FIG. 5H provides a reliable seal and prevents backflow for the air/water valve and allows one way only carbon dioxide and/or air to the patient.

FIG. 6A is a perspective view of the stem for the disposable air/water valve and 6B is a side view of the stem for the disposable air/water valve. FIGS. 6C and 6D are transparent views of stem 101a illustrating grooves 154a, aligners 114a, 116a, 130a, 134a and 190a, gaskets 164a, 166a, 168a, 170a, 172a, 174a, 176 and 178, ridges, and transverse hole 180a. Cutouts 220a, 222a and 224a are valve gates through which the flow of plastic (for example, polycarbonate) can be more accurately controlled whenever stem 101a is prepared by injection molding. In some embodiments, cutouts are ejector pin marks. FIGS. 6A and 6D illustrate duckbill 182 in a closed position. FIGS. 6C and 6G show receptacle 184 into which duckbill 182 can be press fit or attached to the stem by an adhesive. FIGS. 6E and 6G illustrate more details regarding disc 190a of the duckbill stem design. FIG. 6E is a bottom view of the distal end of stem 101a illustrating detail 230a of disc 190a of the duckbill stem design. FIG. 6G is a cross-sectional view of stem 101a along AA plane of FIG. 6D. When a fluid is pumped through the duckbill, the flat end of the duckbill opens to allow the pressurized fluid to pass. However, when the fluid pressure is removed, the duckbill returns to its original flat shape preventing backflow. As with the umbrella design, the duckbill design of stem 101a provides a reliable seal and prevents backflow for the air/water valve and allows one-way flow for carbon dioxide or air to the patient.

FIG. 7B is a side view of a disposable air/water valve stem. FIGS. 7C and 7D are transparent views of stem 101b illustrating grooves 154b, aligners 114b, 116b, 130b, 134b and 190b, gaskets 164b, 166b, 168b, 170b, 172b, 174b, 176b and 178b, and transverse hole 180b. Cutouts 220b, 222b and 224b are valve gates through which the flow of plastic (for example, polycarbonate) can be more accurately controlled whenever stem 101b is prepared by injection molding. In some embodiments, cutouts are ejector pin marks. FIGS. 7C, 7D and 7G illustrate more details regarding disc 190b of the diaphragm design of stem 101b. These figures illustrate diaphragm 186 which can be press fit into receptacle 188 or can be glued to the stem by an adhesive. FIG. 7E is a bottom view of the distal end of stem 101b. FIG. 7F is a top view of the proximal end of stem 101b. FIG. 7G is a cross-sectional view of stem 101b along the AA plane of FIG. 7D. The diaphragm design of stem 101b also provides a reliable seal and prevents backflow for the air/water valve and allows one way only carbon dioxide air to the patient.

Figure 8A:
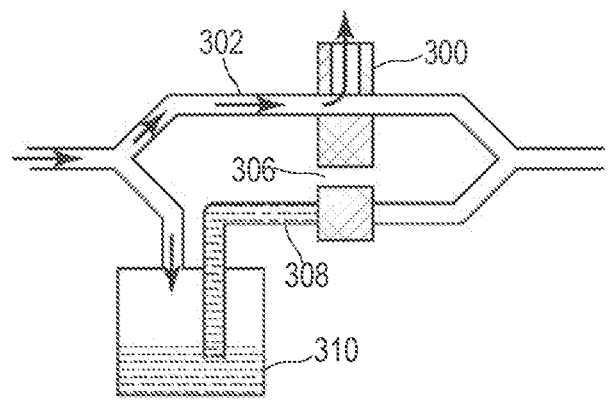
FIGS. 8A, 8B and 8C illustrate the general operation of an air/water valve in an endoscope.
Figure 8B:
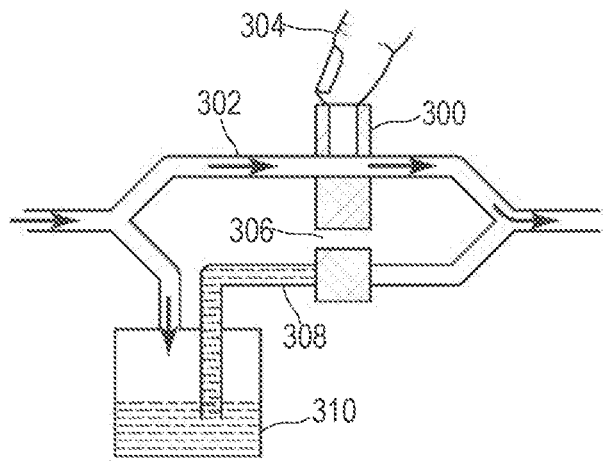
Figure 8C:
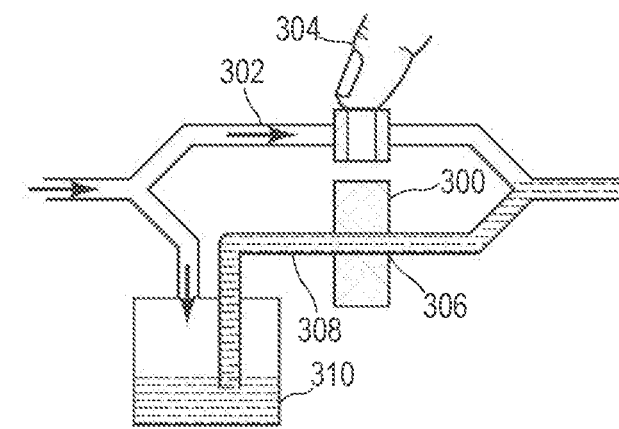

FIGS. 8A, 8B and 8C are illustrative implementations of the operation of an air/water valve in an endoscope. Note that the discussion with reference to FIGS. 8A-8C is directed toward a generic air/water valve, which can include valve 100 illustrated in FIG. 5A and other air/water valve embodiments having stems 101a or 101b as illustrated in FIGS. 6A and 7A. The discussion merely provides an explanation of how an air/water valve generally operates in an endoscope, including a FujiFilm™ endoscope.

In FIG. 8A, air/water valve 300 is positioned in the air/water cylinder of an endoscope and is shown in an un-actuated position. The endoscope provides an air channel 302 for air and a water channel 308 for water. Air channel 302 and water channel 308 are connected to water bottle 310. Water channel 308 extends into the fluid contained in water bottle 310. When air/water valve 300 is placed in the air/water cylinder of the endoscope, air/water valve 300 passes through air channel 302 and water channel 308. Air flow (provided by an air pump or the like), shown by the arrows, may flow into water bottle 310 and air channel 302. However, because water bottle 310 is sealed and water channel 308 is blocked by air/water valve 300, air tends to flow down air channel 302 towards air/water valve 300. In the un-actuated position with the air vent uncovered, air/water valve 300 allows air to escape from a vent. For example, with disposable air/water valve 100, air would flow into first opening 142 of stem 101 through the internal bore of stem 101 and out proximal end 135 of the disposable air/water valve 100. Note that disposable air/water valve 100 in FIG. 1A provides several gaskets or seals 164, 168, 170, 172 and 174 that prevent air or water from leaking from air channel 302 or water channel 308. Opening 306 of the air/water valve 300 is not aligned with the water channel 308 and, there is no movement of water away from the water bottle 310, as the water channel 308 is blocked.

In FIG. 8B, air/water valve 300 in the air/water cylinder of an endoscope is shown in an un-actuated position with the vent blocked by an operator's finger 304 or the like. Because water bottle 310 is sealed and water channel 308 is blocked by air/water valve 300, air tends to flow down air channel 302 towards air/water valve 300. However, when the air vent of air/water valve 300 is blocked by the operator 304, air flows and is pushed past air/water valve 300 towards the distal end of an endoscope. This allows the operator to insufflate a body cavity by blocking the air vent of air/water valve 300 without actuating the valve. In FIG. 8B, opening 306 of the air/water valve 300 is shown blocked.

In FIG. 8C, air/water valve 300 is shown in an actuated position. When air/water valve 300 is actuated, the resilient member (e.g., spring, rubber, elastic, etc.) in the air/water valve 300 is compressed and air channel 302 is blocked by the air/water valve 300. However, actuating air/water valve 300 moves opening 306 of the air/water valve 300 into water channel 308, thereby creating a passageway for fluid to pass through air/water valve 300. Because air channel 302 is blocked by operator 304 pressing down on the air/water valve 300, air flows into water bottle 310. As the air pressure in water bottle 310 increases, fluid is forced from water bottle 310 into water channel 308. By actuating air/water valve 300, the operator 304 causes water to flow towards the distal end of the endoscope for rinsing, irrigation, or the like.

Figure 9A:
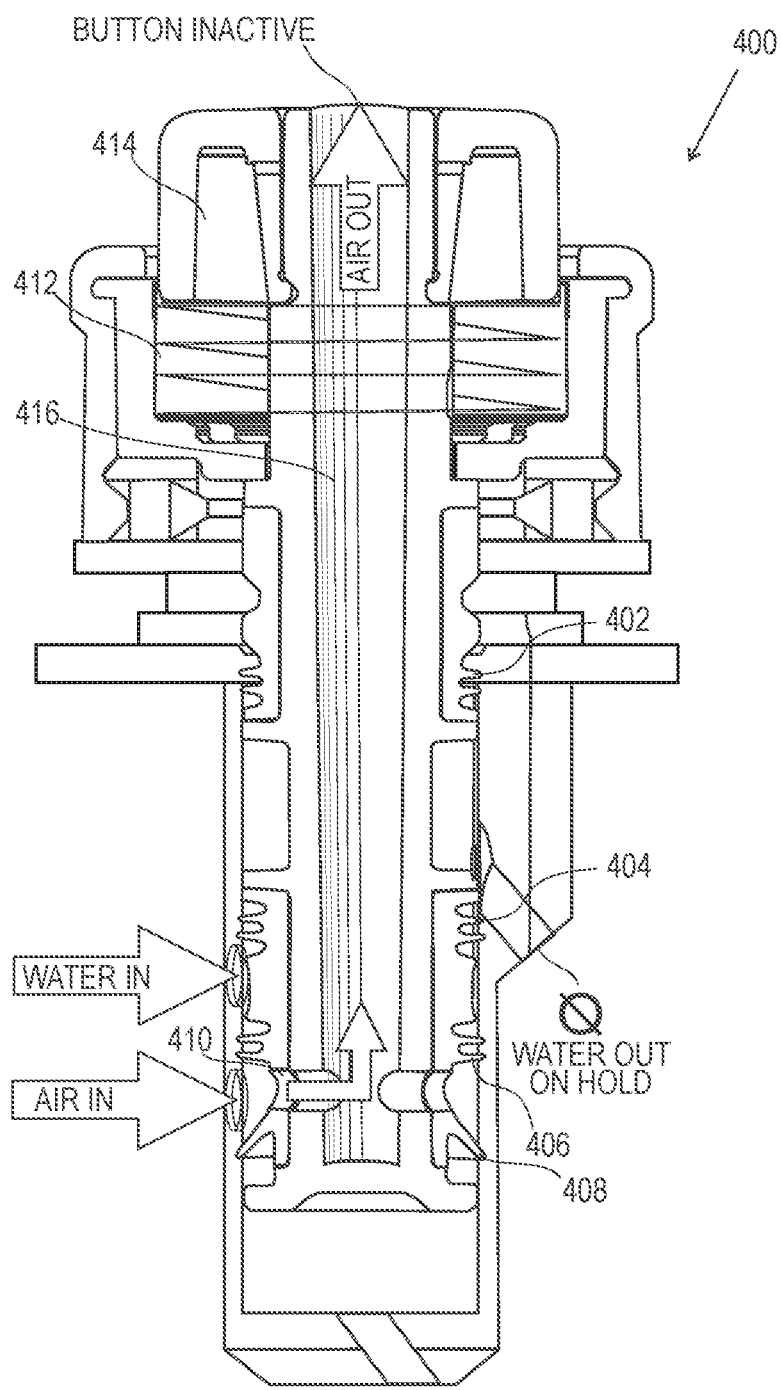
FIGS. 9A, 9B and 9C illustrate the general operation of a disposable air/water valve in an endoscope.
Figure 9B:
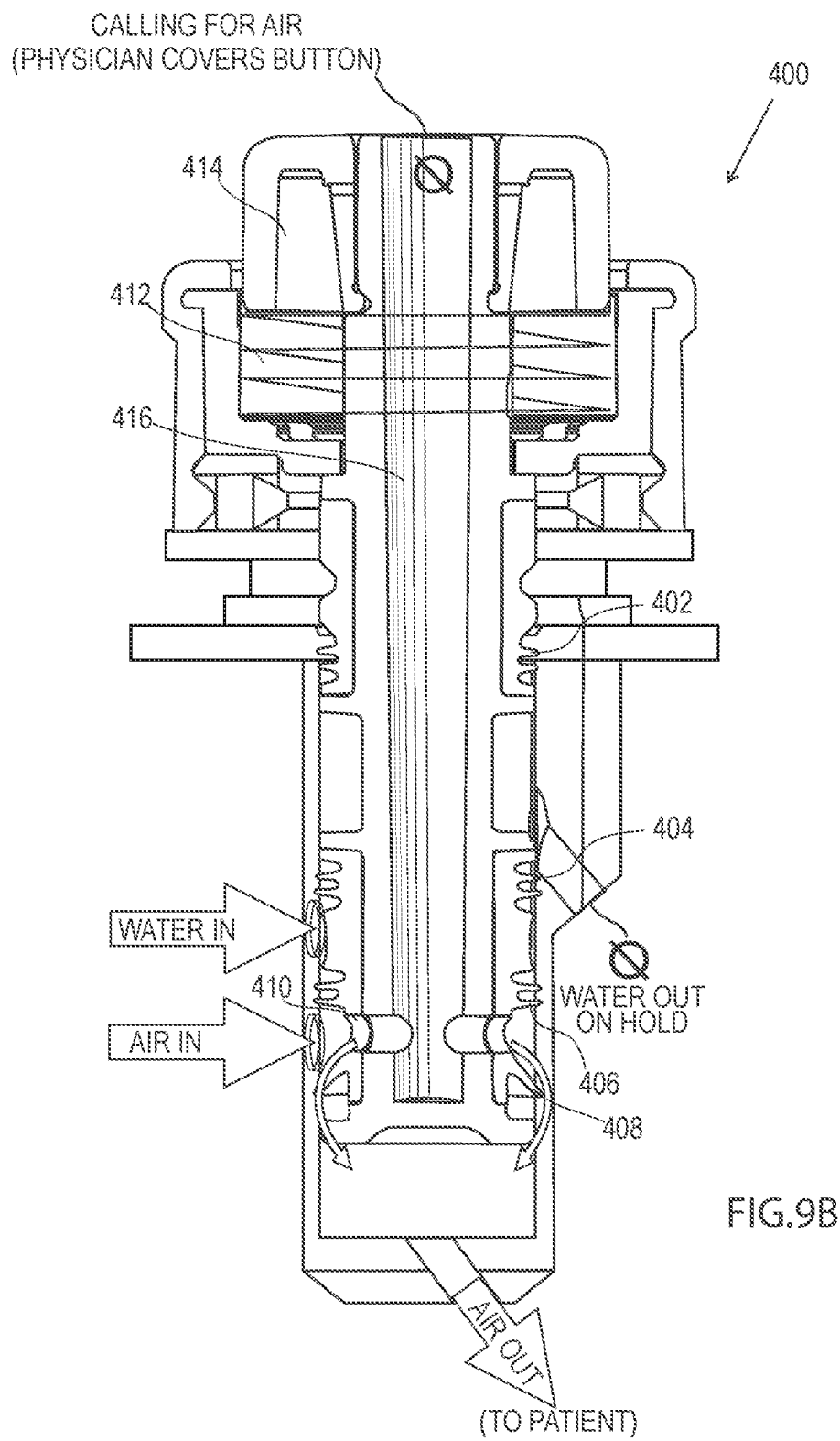
Figure 9C:
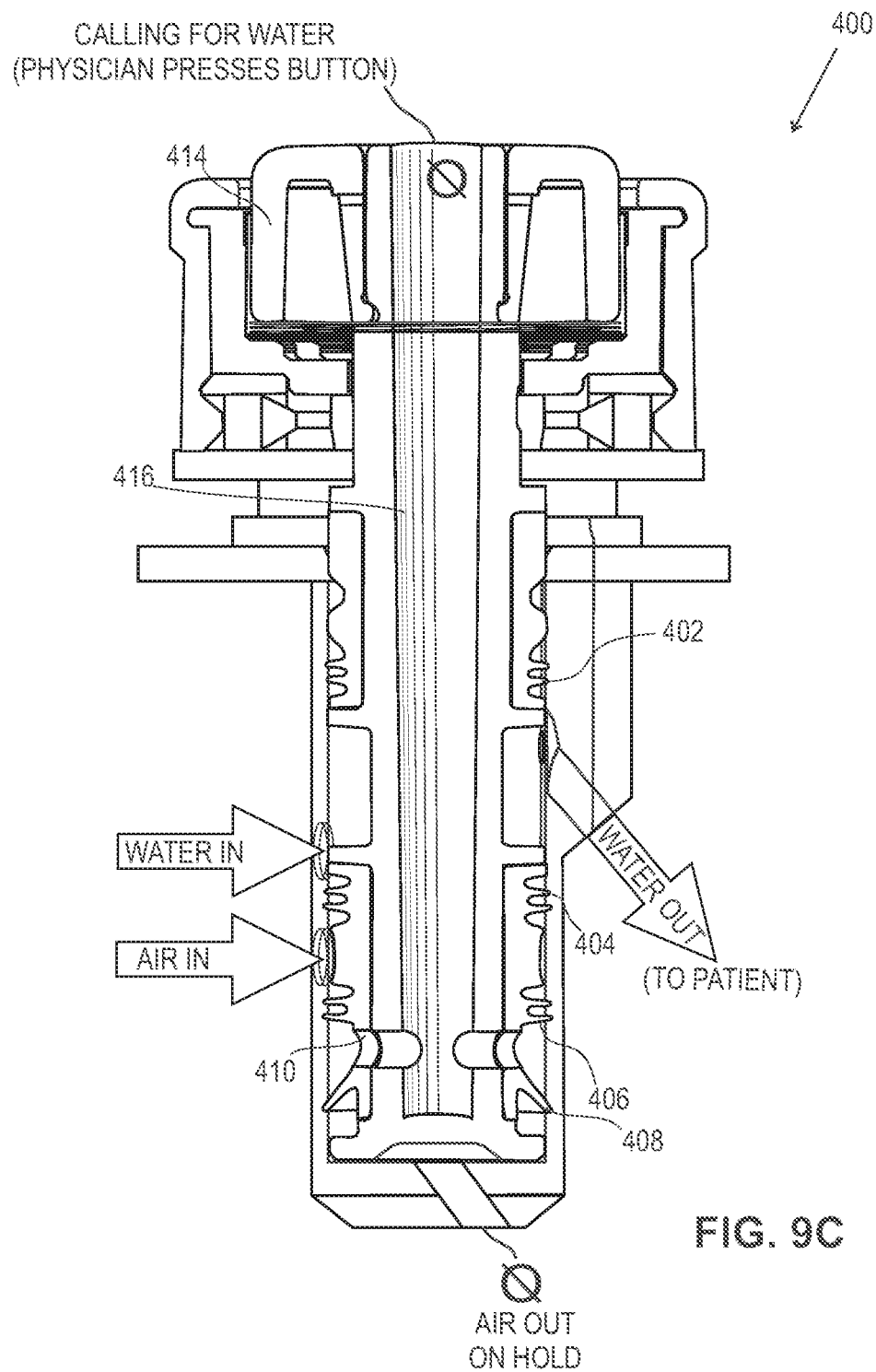

FIGS. 9A, 9B and 9C are illustrative implementations of the operation of a disposable air/water valve 400 in an endoscope. In FIG. 9A, disposable air/water valve 400 is shown in an undepressed or un-actuated position. Gaskets or seals 402, 404, 406 and 408 prevent air from escaping the chamber between seals 406 and 408. The proximal end of the air/water valve and the proximal end of the central bore, adjacent to cap 414, has an opening allowing air to leave the valve. The opening allows the air to escape through the central bore of disposable air/water valve 400 as shown. A second opening 410, between seals 406 and 408, near the distal end of the valve is transverse to a longitudinal axis along the central bore allowing air to enter the valve. The disposable air/water valve 400 also provides spring 412, cap 414, and stem 416. Spring 412, surrounding a portion of stem 416, is disposed below cap 414.

FIG. 9B illustrates when an operator places a finger on top of disposable air/water valve 400 to prevent air from escaping, pressure in the chamber between seals 406 and 408 increases. If the operator has created a sufficient seal by substantially blocking air flow out of the top of disposable air/water valve 400, the wall of seal 408 collapses to allow air to flow past the seal. Seal 406 prevents air from escaping out through the air/water cylinder of the endoscope. As a result, the air can only escape out through the outlet to the patient.

Seals 404 and 406 prevents water from escaping past disposable air/water valve 400 in the un-actuated position. Seal 404 separates the water inlet from the water outlet. It should be noted that residual water from previously depressing disposable air/water valve 400 may remain between seals 402 and 404. Seal 402 prevents the residual water from escaping further up the air/water cylinder of the endoscope.

In FIG. 9C, disposable air/water valve 400 is depressed in the air/water cylinder of an endoscope. Seals 406 and 408 prevent air from the air output (e.g., air from the patient) from flowing back into the endoscope. Seals 406 and 408 prevent air from the air input from escaping the chamber between seals 406 and 408. It should also be noted that an operator's finger is blocking air flow through the central bore of disposable air/water valve 400. In the depressed position, seal 404 no longer separates the water input and water output. Water from the water input fills the area between seals 402 and 404 and activates the water output to the patient or allows the water to flow out (or be supplied) to the patient. Seals 402 and 404 prevent water from escaping up the air/water cylinder of the endoscope.

Although the air/water valve is designed to be used with an endoscope, it will be understood that other medical instruments can be used with the present air/water valve or assembly. These instruments include, for example, gastroscopes, colonoscopes, laparoscopes, bronchoscopes, or any medical instruments with a camera that requires air and/or water use.

Figure 10:
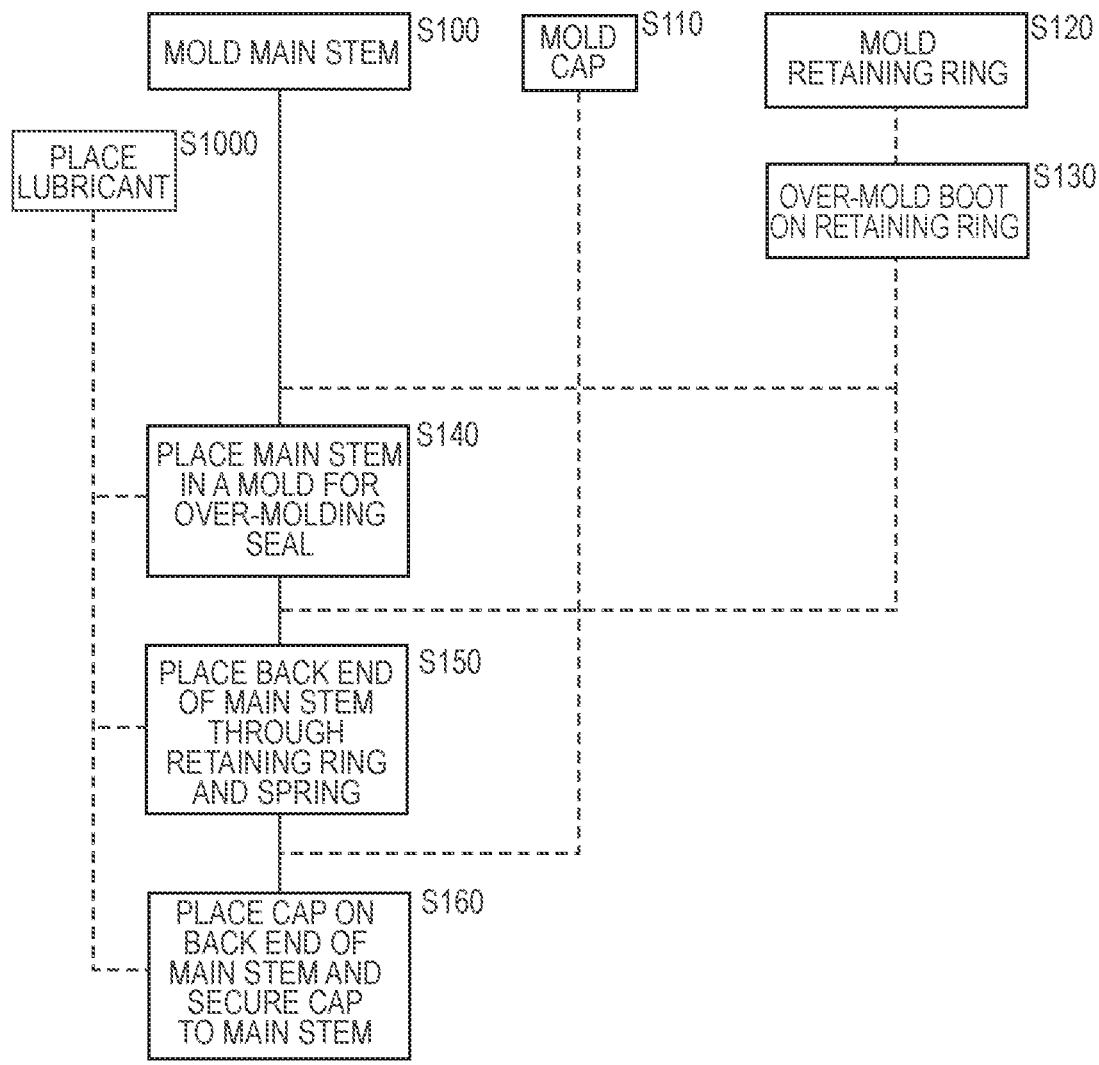
FIG. 10 illustrates an embodiment of a manufacturing process for a disposable air/water valve including placement of the lubricant on the valve.

FIG. 10 is a flow chart of a manufacturing process for a disposable air/water valve. The first step S100 of the manufacturing process is molding the stem from a suitable material, such as plastic, polymeric material(s), or any other suitable material(s). Molding the stem and using lower cost material(s) creates considerable cost savings when compared to the metal used by reusable air/water valves. Additionally, stem 101 (101*a*, 101*b*) in FIGS. 1A, 5A, 6A and 7A is a single piece that does not need to be assembled, like the stem assembly of a reusable air/water valve, thereby reducing assembly cost. For example, stem 101 (101*a*, 101*b*) is monolithic (e.g., a single piece) having gasket surfaces and grooves 150, 152, 154, 156, and 158 and ridges 126, 128, 130, 132 and 134 that are molded as part of the stem 101. Stem 101 (101*a*, 101*b*) also includes opening end 142 (142*a*, 142*b*). These ridges and/or grooves can be rigid or they can be flexible.

Unlike the non-disposable air/water valves that are not monolithic as many of the ridges and/or grooves are molded separately and contain different material than the stem, which is metal, the monolithic stem (one piece) comprises a plurality of ridges and grooves that are, in some embodiments, the same material as the stem.

Button cap 102 and stanchion 200 are also molded in steps S110 and S120. Boot 104 may be over-molded on stanchion 200 in step S130. Further, in other implementations, boot 104 may be molded separately and simply placed on stanchion 200 during assembly. However, in contrast to stem 101, button cap 102 and stanchion 200/boot 104 are not required until later in the manufacturing process. As a result, the dotted lines indicate that steps S110, S120, and S130 may occur at various times in the manufacturing process. Because the boot, button cap, and stanchion are relatively simple when compared to the stem, they may be manufactured using additional manufacturing processes that may not be suitable for stem 101, such as blow molding, over-molding, injection molding, casting, machining, stamping, or any other suitable manufacturing process.

In some embodiments, once the disposable air/water valve is assembled, in step S1000, lubricant 1000 can be applied on the stem, spring and/or spring stanchion of the air/water valve assembly. In other aspects, the method of manufacturing of a disposable valve further comprises placing tabs of the spring stanchion into recessed apertures of the stem, and over-molding a boot on the spring stanchion or over-molding a boot onto the spring stanchion, wherein (i) the stem is color coded; (ii) a sealing ledge on the boot creates a seal against a button head of the stem; (iii) the stem provides an O-ring or an alternate sealing device to assure an air-tight seal within a suction port; (iv) the stem provides a sealing means to assure an air-tight seal within a suction port or the stem; (v) the stem has a diameter that assures an air-tight seal within a suction port; (vi) the length of the stem is reduced; or (vii) the lubricant comprises an antimicrobial agent.

Stem 101 may be placed in a mold suitable for over-molding gaskets or seals 120, 164, 166, 168, 170, 172 and 174 in step S140. For example, in some embodiments, the stem may be placed in a clam-shell like mold and the material utilized to form gaskets 120, 164, 166, 168, 170, 172 and 174 may be injected into the mold. The mold forms the gaskets or seals 120, 164, 166, 168, 170, 172 and 174 of FIG. 1A in seal retaining regions, gasket surfaces or grooves 150, 152, 154, 156 and 158.

Figure 15A:
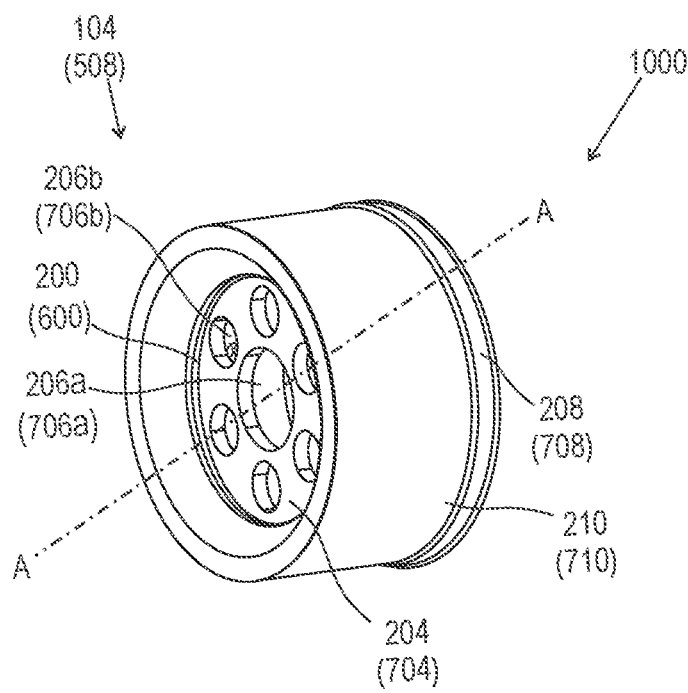
FIG. 15A illustrates a perspective view of an embodiment of a boot for use with a disposable air/water or a disposable suction valve in endoscopes.

The gaskets or seals of the current application can be made from rubber, one or more polymeric material(s), or any other suitable material(s). The seals are preferably made from a pliable material to provide a proper seal when disposable air/water valve 100 is in use. As discussed previously regarding steps S110, S120, and S130, boot, button head or cap, and stanchion can be molded at various stages of the manufacturing process. However, note that each of the components must be made before the step they are specifically needed in. For example, stanchion 200 (200*a*, 200*b*) of FIGS. 15A and 15B must be molded before step S150 because it is needed in step S150 in the manufacturing process. Similarly, button cap 102 of FIGS. 1A and 16A is needed before proceeding to step S160 and boot 104 of FIGS. 1A and 15A is needed before proceeding to step S130.

In step S150, the opening end 142 (142*a*, 142*b*) of FIGS. 5A, 6A and 7A of stem 101 is placed through the opening in the diaphragm of stanchion 200 (200*a*, 200*b*) and through resilient member (e.g., spring, rubber, elastic, etc.) not shown. Button cap 102 may then be placed on the proximal end 135 (135*a*, 135*b*) of stem 101 (101*a*, 101*b*) and secured to the stem 101 (101*a*, 101*b*) in step S160. For example, the disposable air/water valve 100 may be attached (e.g., snap fit, adhesive, glue, molding, over molding, curing with UV light, welding, ultrasonically welding, or the like or combinations thereof) to secure button cap 102 and the gaskets or seals 164, 166, 168, 170, 172 and 174 (164*a*, 166*a*, 168*a*, 170*a*, 172*a*, 174*a*, 176, 178, 164*b*, 166*b*, 168*b*, 170*b*, 172*b*, 174*b*, 176*b*, 178*b*). In other implementations, button cap 102 may be secured to stem 101 (101*a*, 101*b*) using any attachment means (e.g., snap fit, adhesive, glue, molding, over molding, curing with UV light, welding, ultrasonically welding, mechanical attachment, or the like or combinations thereof) to complete the assembly of disposable air/water valve 100.

Figure 17A:
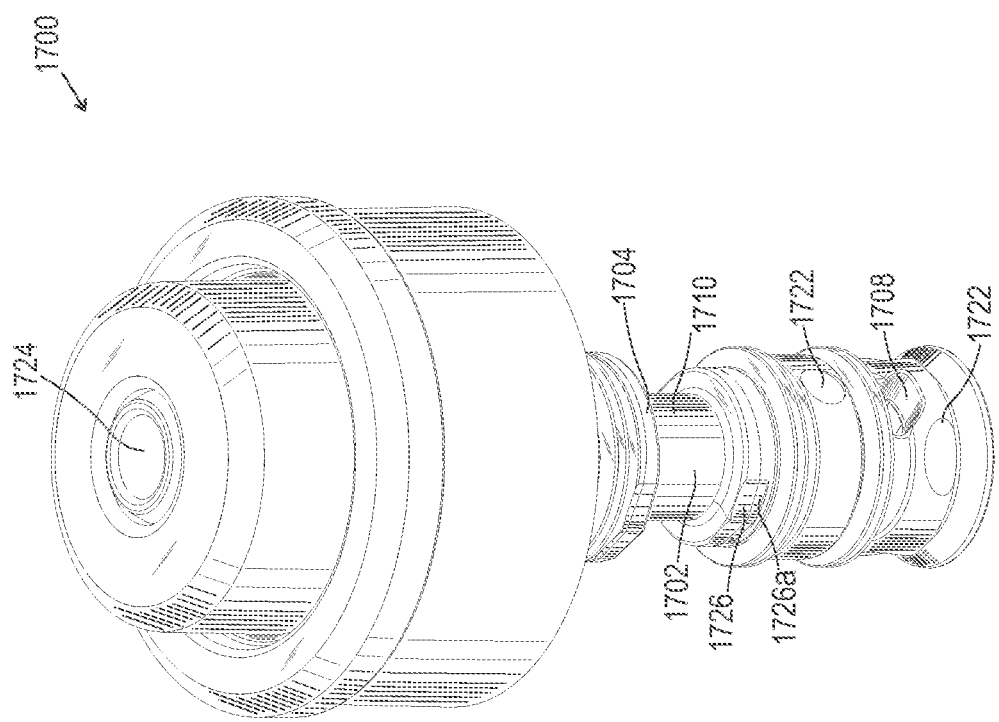
FIG. 17A illustrates a perspective view of an embodiment of a disposable air/water valve suitable for use in endoscopes.

FIG. 17A illustrates a different embodiment of disposable air/water valves 1700 for use with endoscopes. FIGS. 17A, B, C, D and E are perspective, side, bottom views of air/water valves 1700. While in all implementations, the air/water valves contain gaskets, in valve 1700, disc and/or gasket has an indentation 1722. In some embodiments, the indentation may contain various shapes including oval, rectangular, or circular for the improvement of the fluid flow and/or to stabilize fluid flow (e.g., air flow) proximally to distally. The indentation may be disposed above and/or below the opening that is transverse to the stem 1710. In some embodiments, an outer surface of the indentation may be rounded to stabilize disposable air/water valve 1700, as shown in FIG. 17D. The outer surface of the indentation limits the movement of the disposable air/water valve 1700 away from its intended central axis to prevent lateral forces at the button top from causing gasket seal breaches. In some embodiments, the gasket has one or more grooves 1702 and/or ridges 1704 adjacent to the indentations. In some embodiments, the indentation may be on the groove of the gasket. The valves comprise a spring cup/stanchion 1706 that has an opening to receive a stem and various cutouts 1712 around the opening. In some embodiments, the cutouts and the opening are connected. In some embodiments, the cutouts are separated from the opening. In some embodiments, the cutouts may have circular, oval, or rectangular shape. In some embodiments, the bottom of the spring cup/stanchion has a projected area 1714 creating a tapered level that is configured to facilitate disposable air/water valve 1700 stability onto a mating surface of an endoscope port. In some embodiments, the opening in the spring cup/stanchion is only on the projected area. The spring cup/stanchion has a boot around its outer ring. In some embodiments, the inner surface of the boot has grooves 1716 and ridges 1718 spread radially around the circumference of the inner surface. These cutouts, grooves and ridges, among other things, provide securement to an endoscope port and allows for secure attachment and easy detachment.

Figure 17E:
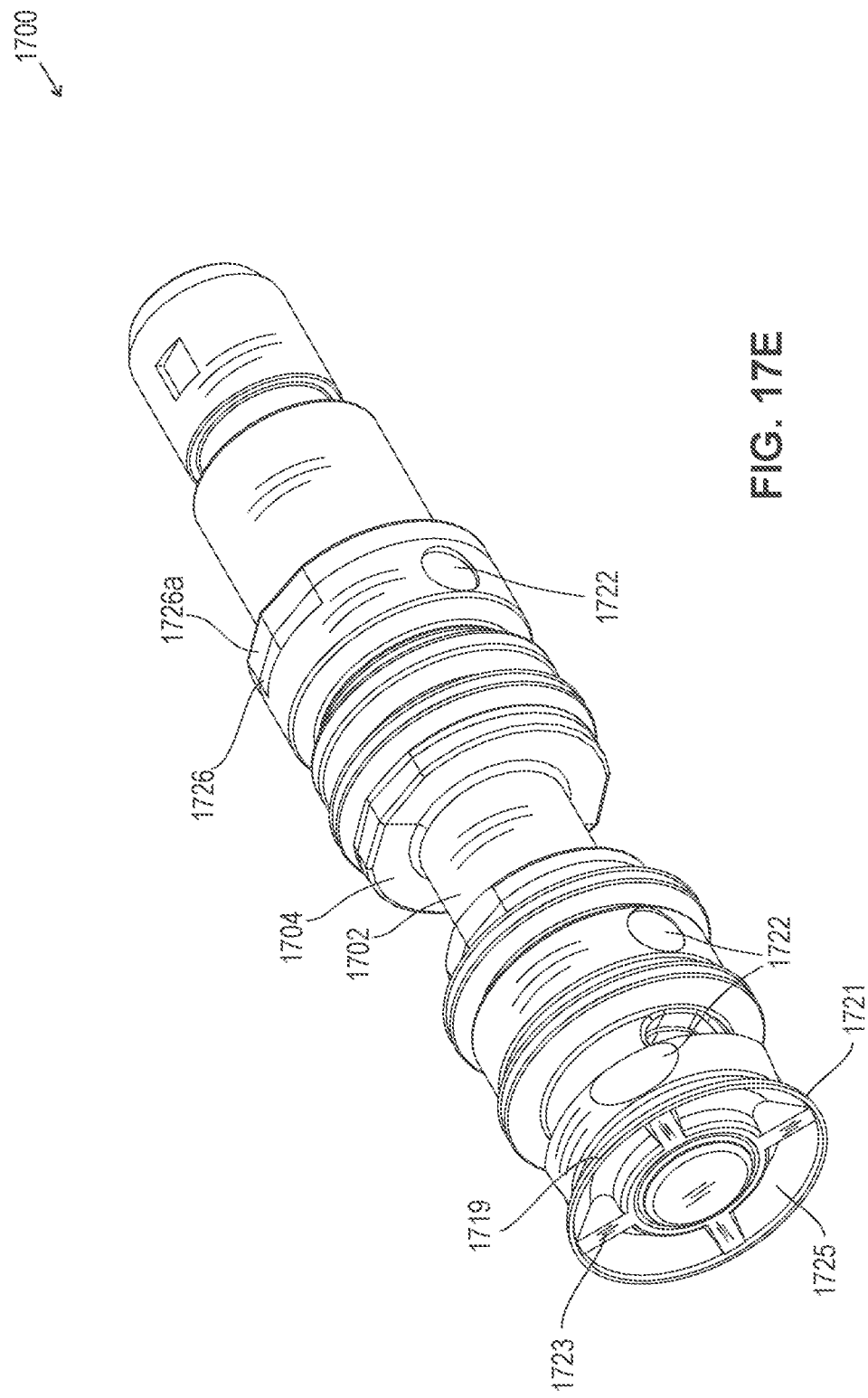
FIG. 17E illustrates a perspective view of the stem of an embodiment of a disposable air/water valve for use in endoscopes.

FIGS. 17D and 17E are a side view and a perspective view of the stem of the air/water valve. The stem 1710 has a longitudinal axis and an opening 1708 transverse to the axis. The stem has a proximal end and a distal end. The proximal end is adjacent to an opening 1724 along the axis and the distal end is adjacent to the transverse opening. In some embodiments, the proximal end of the stem has a recess. In some embodiments, the recess is rectangular. In some embodiments, the gaskets have an over-molding shutoff 1726. In some embodiments, the shutoff is adjacent to the indentation 1722. In some embodiments, the stem also has an over-molding shutoff 1726a adjacent to the ledge of the gasket. In some embodiments, during manufacture of the disposable air/water valve 1700, a seal is created at the shutoffs.

In some embodiments, as shown in FIGS. 17A, 17B, and 17D-J, the distal end of the stem includes an umbrella valve 1719 that is over molded over the stem. In some embodiments, the umbrella valve is configured for one directional movement of airflow from a proximal to a distal direction. An underside of the umbrella valve includes a plurality of supports, such as ribs 1723, as shown in FIG. 17E. The ribs are configured to provide rigidity to the umbrella valve as well as assisting in the proper configuration of the umbrella valve during movement. The ribs also prevent reverse folding of the umbrella valve with axial valve movement. A plurality of collapsible recessed portions 1725 are disposed between the ribs. The plurality of collapsible recessed portions are configured to allow an outer edge 1721, of the umbrella valve to collapse inward and allow air flow in a proximal to distal direction to flow around the outer edge of the umbrella valve when an operator places a finger on top of the disposable air/water valve 1700. In some embodiments, the ribs are thicker than the plurality of collapsible recessed portions.

In some embodiments, the outer edge of the umbrella valve is molded without a parting line and includes an angled or chamfered edge 1727, as shown in FIGS. 17E and 17F, that is configured to align and mate with an endoscope port. The angled or chamfered edge creates a substantially leak free air seal with the surface of the endoscope port to prevent retrograde air flow/leaks that would result from backpressure during use. In some embodiments, the seal distance is from about 0.008 to about 0.010 inches. In some embodiments, as shown in FIGS. 17G and 17H, the outer edge of the umbrella valve alternatively includes a protrusion 1729 that forms an outer flat edge to create a substantially leak free seal against air pressure backflow.

Figure 17J:
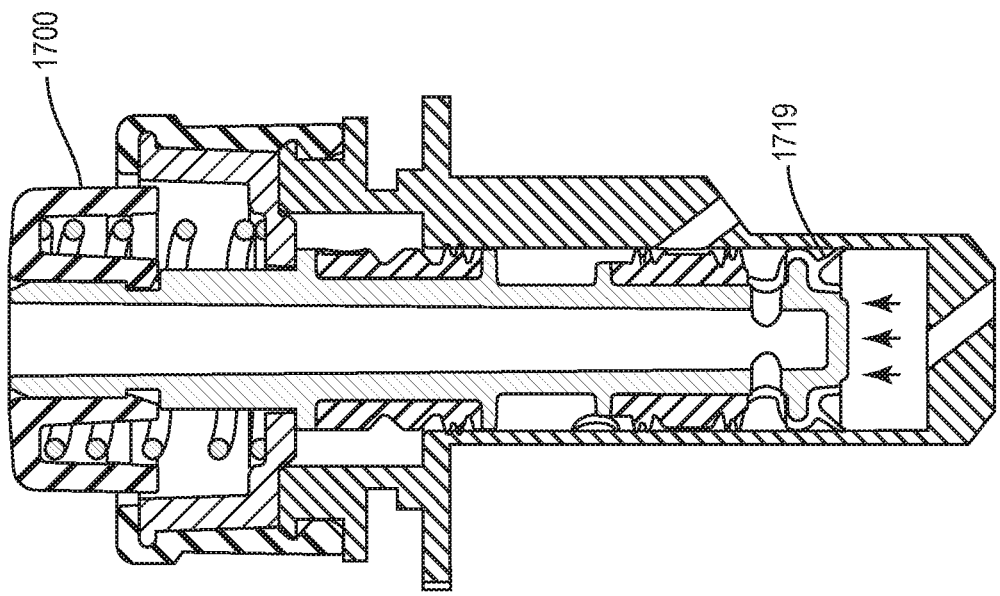
FIGS. 17I and 17J illustrate embodiments of the general operation of a disposable air/water valve in a medical instrument, such as for example, an endoscope.
Figure 17I:
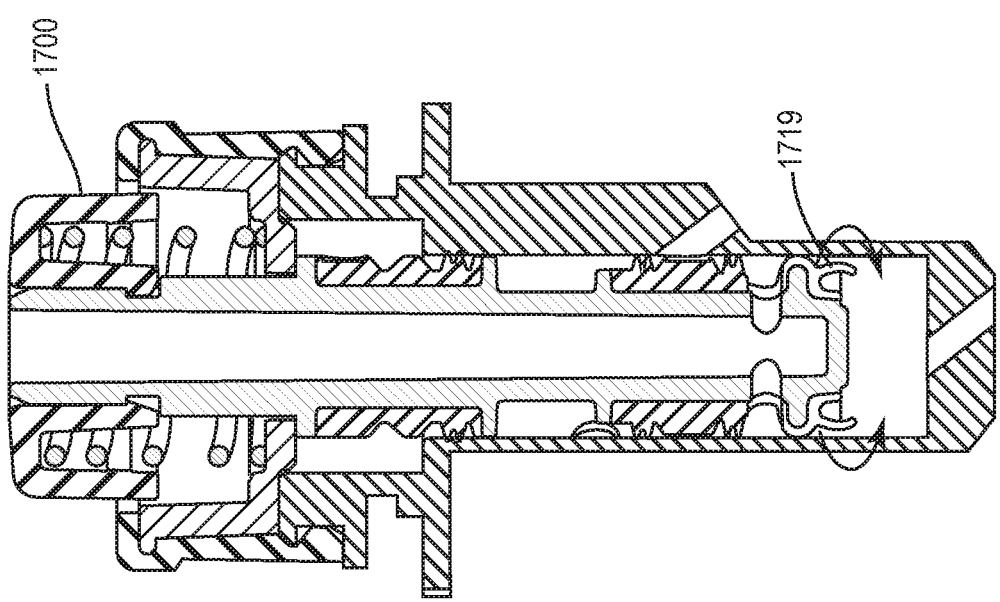

FIGS. 17I and 17J are illustrative implementations of the operation of a disposable air/water valve 1700 in an endoscope. In FIG. 17I, the disposable air/water valve 1700 is depressed in the air/water cylinder of an endoscope. An operator places a finger on top of the disposable air/water valve 1700, to prevent air from escaping. The outer edge of the umbrella valve then collapses inward to fold the umbrella valve so that air can flow in a proximal to distal direction to flow around the outer edge of the umbrella valve. As shown in FIG. 17J, when an operator uncovers the disposable air/water valve 1700 and the disposable air/water valve 1700 is in an undepressed or un-actuated position, the umbrella valve deploys and creates an air seal with the surface of the endoscope port to prevent retrograde air flow/leaks that would result from backpressure during use. The deployment of the umbrella valve will prevent backflow.

In some embodiments, as shown in FIG. 17K, during the manufacturing process, the outer edge of the umbrella valve is molded without a parting line 1733 in mold 1731 in order to form a continuous outer edge. An outer edge without a parting line creates a better seal. To manufacture the outer edge of the umbrella valve without a parting line, the outer edge is encased in the steel of the lower core pin during injection molding. In some embodiments, the umbrella valve is made from a thermoplastic elastomer (e.g., TPE) that is over molded onto the stem. In some embodiments, the stem can be made from polycarbonate.

Disposable Suction Valves

Figure 11A:
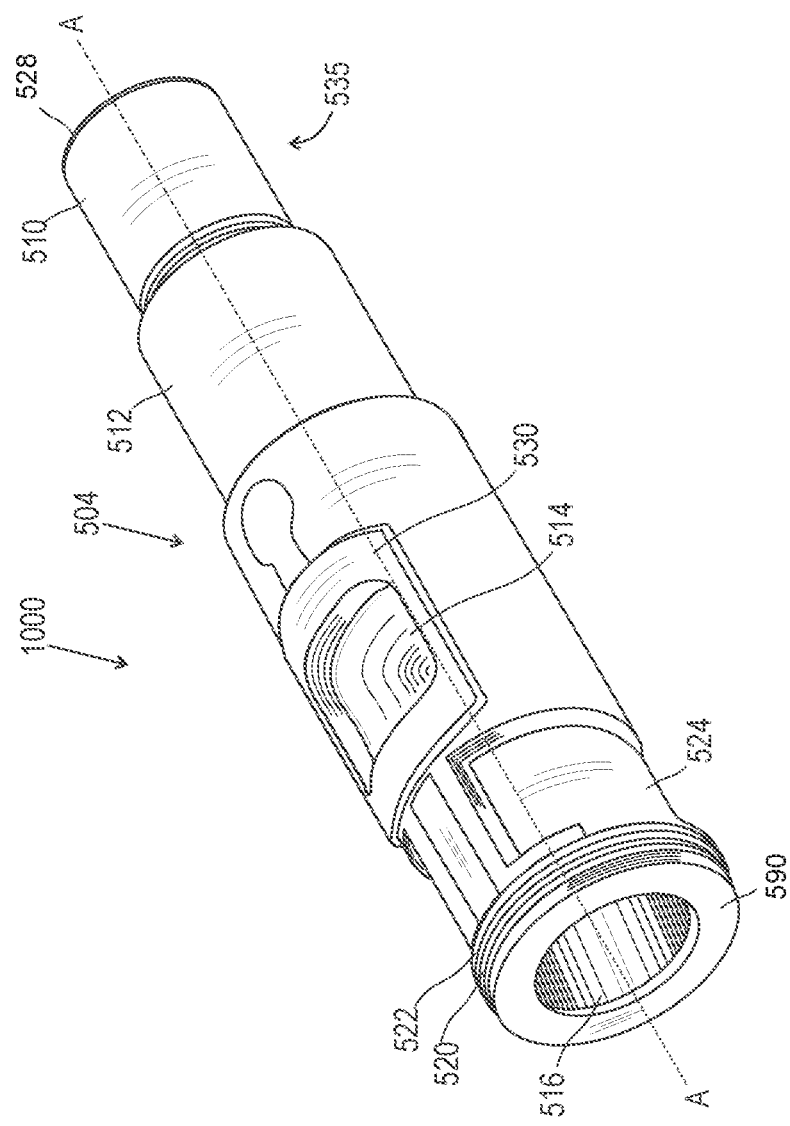
FIG. 11A illustrates a perspective view of a stem of another embodiment of a disposable suction valve for use in endoscopes.
Figure 12A:
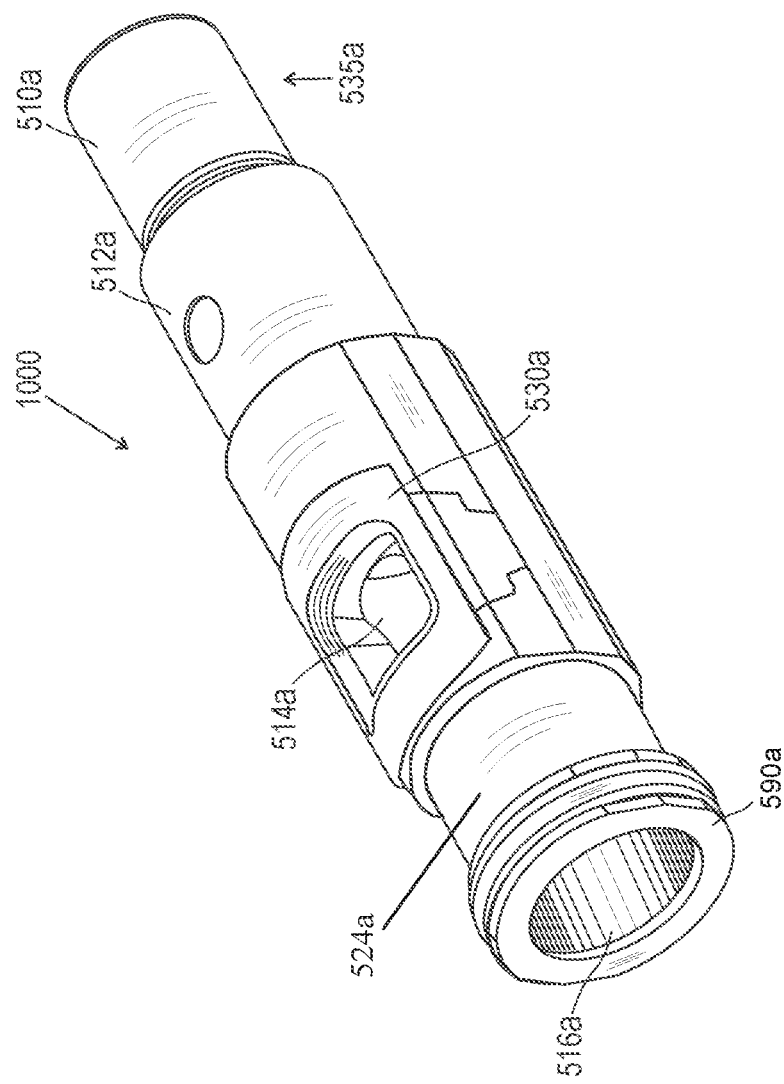
FIG. 12A illustrates a perspective view of a stem of another embodiment of a disposable suction valve for use in endoscopes.

FIGS. 1B, 2B, 3B, and 4B are front and perspective views of disposable suction valves 500. FIGS. 11A and 12A are perspective views of the disposable suction valves main stem that is made from plastic material. Because there are several implementations of the air/water valve, in this application, identical elements will be referenced in parenthesis. Moreover, reference to one element applies equally to all identical air/water disposable valve elements. Suction valve 500 has as main components, all positioned along longitudinal axis AA, main stem 504 (504a), button head or cap 501, boot 508, resilient member (not shown), gaskets, seals or surfaces 530, 520 and 522 (530a, 520a and 522a). Main stem 504 (504a) is monolithic (e.g., a single piece) has grooves 510, 512 and 524 (510a, 512a, and 524a), that are molded as part of the stem 504 (504a) and proximal end 535 (535a) positioned about opening end 522 (522a). Stem 504 (504a) further contains a partial transverse opening 514 (514a). Opening 514 (514a) is a second opening transverse to and intersecting first opening 516 (516a in FIG. 12A), which is adjacent end rim 590 in FIG. 11A, which is adjacent end rim 590a in FIG. 12A. The ridges and/or grooves can be rigid or they can be flexible. In the embodiments shown, due to the ridges and/or grooves the main stem has a varied diameter, where the diameter is greater by the ridges and the diameter is smaller by the grooves. This configuration allows gaskets or seals to be inserted into the grooves.

Disposable suction valve 500 may include a stem 504 (504a), stem insert 502 (502a), boot 508 (508a), spring cup/stanchion 600 (600a) (FIGS. 3B, 15A and 15B) and spring 506 (506*a*) (not shown). One or more components of the disposable suction valve may comprise disposable material, including, but not limited to polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. Stem 504 (504*a*) and stem insert 502 (502*a*) may be formed from a suitable material or combination of material(s), such as plastic, polymeric material(s), or the like. Stem insert 502 may be color coded (e.g. black, orange, red, etc.) to indicate the type of valve or that the valve is a suction valve. In other embodiments, stem insert 502 (502*a*) may be omitted or color coding may be provided by another means (e.g. painting).

Boot 508 (508*a*) may be formed from a suitable material, such as for example, polyurethane, polyurea, polyether (amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), or the like or combinations thereof.

In one embodiment, boot 508 (508*a*) may be formed from a pliable material for ease of assembly e.g., a material that allows boot 508 to slide over spring stanchion cup 600 during assembly and seal off the suction in the circuit. In other embodiments, boot 508 may be over-molded onto the spring stanchion cup. Spring 506 may be formed from a suitable material, such as corrosion resistant metal, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic, or the like or combinations thereof.

Spring 506 (506*a*) of suction valve 500 can be prepared of any resilient member (e.g., a member that resumes its original shape or position after being compressed). A resilient member can include, for example, a spring, plastic, rubber or other elastic member that allows its original shape or position after being compressed.

The disposable suction valve of the current application, in some embodiments, improves suction, reduces or eliminates leaks and/or fluid going into and out of unwanted areas of the valve or in unwanted areas of the medical instrument. The disposable suction valve of the current application, in some embodiments, reduces or eliminates debris from clogging the valve.

In some embodiments, as illustrated in FIGS. 1B to 4B unlike the non-disposable seven-component suction valves in the prior art, the disposable suction valve of the current application, comprises four components: a stem 504, boot 508, spring cup/stanchion 600 (FIG. 3B) and spring 506 (not shown). In some embodiments, unlike the non-disposable seven-component suction valves in the prior art, the disposable suction valve of the current application, comprises five components: a stem 504, boot 508, spring cup/stanchion 600 (FIG. 3B), spring 506, and stem insert 502.

In some embodiments, the difference from the disposable suction valve of the current application and the prior art is that the prior art valve has a stem (with a threaded button head end) plus a metal backing plate (to thread onto stem and offer a secure joint for the plastic button head) and a plastic button head. In the disposable suction valve of the current application, in some embodiments, the stanchion cup is molded and then the boot is overmolded onto this piece. Accordingly, in some embodiments, as further discussed below the stanchion cup is monolithic with the boot (e.g., they are one piece) and therefore, the manufacturing process is simpler. Therefore, the disposable suction valve of the current application can be easier to manufacture and there is less chance of the components malfunctioning when compared to prior art non-disposable seven-component suction valves.

In contrast, the stem of a re-usable suction valve may be formed from one or more components made of a material that is suitable for repeated cleaning, disinfection, and sterilization, such as stainless steel or the like. While this material allows a re-usable suction valve to be repeatedly cleaned, disinfected, and sterilized for re-use, such material may be costly. It is difficult to properly clean, requires more components, requires additional manufacturing and assembly steps, requires costlier manufacturing processes, and the like. In addition to being costlier to manufacture than a disposable suction valve, a re-usable suction valve also requires equipment and materials that are utilized to repeatedly clean, disinfect, and sterilize the valve.

Figure 4B:
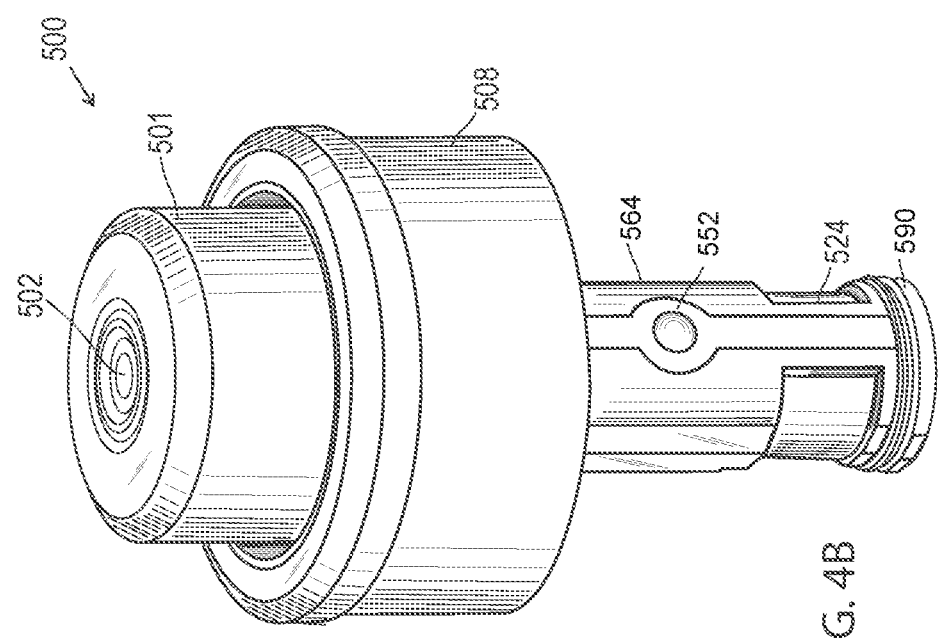
Figure 4A:
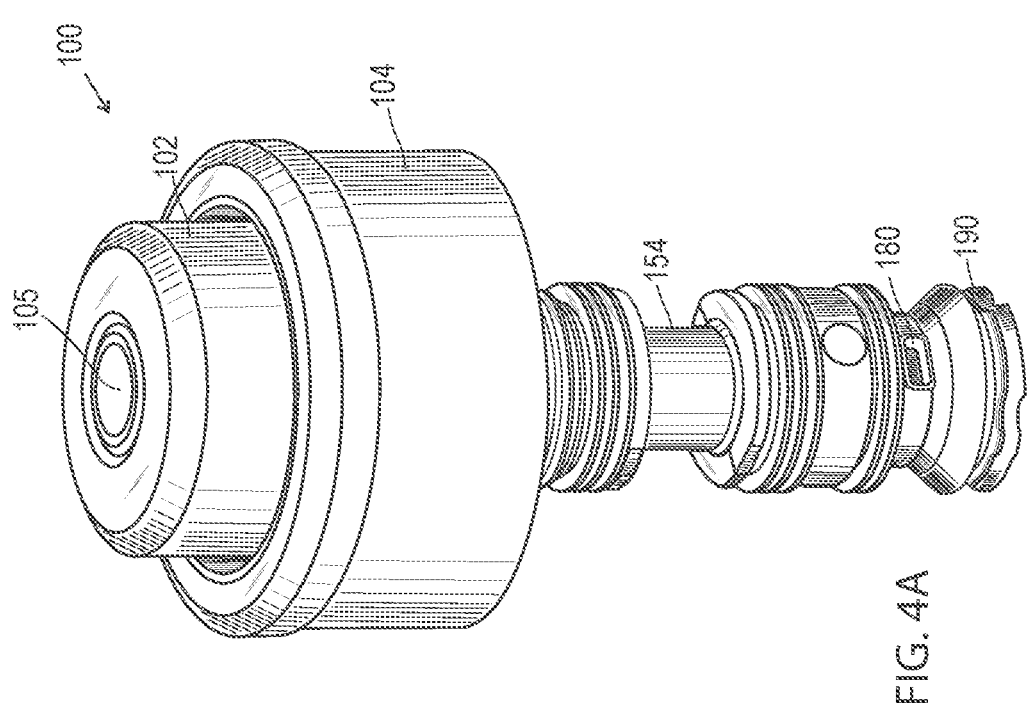

FIGS. 1B to 4B also illustrate lubricant 1000 which may be disposed on valve 500 and at least on stem 504. In some embodiments, lubricant 1000 also contains an antimicrobial agent. In FIG. 4B, the disposable suction valve on surface 564 of the stem has circular region 552 that assists in aligning the valve in the endoscope.

As illustrated in FIGS. 1B to 4B, disposable suction valve 500 contains components found in other valves, for example, stem 504, stem insert 502, boot 508, spring cup/stanchion 600 (FIG. 3B), spring 506 (not shown) and stem cap or button cap 501. Stem 504 of disposable suction valve 500 contains a transverse opening 514 supported by an opening rim/surface 530*a* and protrusion 532*a* (FIG. 12A, 12B), however the transverse opening 514 does not contain a through opening hole that extends transversely and completely through stem 504 (504*a*). As such, the embodiments discussed herein may be modified to accommodate other types and/or brands of endoscopes. In some embodiments, the disposable valves have a plurality of mini-seals (e.g., two, three, four, five, six, seven, eight, nine, ten, eleven, twelve seals, etc.) about the stem either monolithic with the stem or seals that are placed around the stem (e.g., 0 ring seals, or bands placed about the stem).

FIGS. 11A and 12A are perspective illustrations of different implementations of disposable suction valve 500. FIGS. 11B-11F and 12B-12F are cross-sectional, bottom, top and detail views of stems 504 and 504*a* of different implementations of suction valve 500. With reference to FIGS. 11A and 12A, stems 504 and 504*a* are monolithic (e.g., a single piece) containing grooves or recesses 510 (510*a*), 512 (512*a*), and 524 (524*a*), and gaskets 520 (520*a*) and 522 (522*a*). Recess 510 is adjacent to proximal end rim 528 in FIG. 11A. Stem 504 (504*a*) also contains a first opening 516 (516*a*) along axis AA. Stem 504 also contains a transverse opening 514 (514*a*) which has a rim or surface 530 (530*a*). Surface 530 has a gasket surface, which in some aspects can have a rough texture. Similarly, stem 504*a*, illustrated in FIG. 12A, has a surface 530*a*, which is a gasket surface, and, in some aspects, can have a rough texture.

One or more components of the disposable suction valve 500 may comprise disposable material, including, but not limited to polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. Stems 504 and 504a and stem inserts 502 and 502a may be formed from a suitable material or combination of material(s), such as plastic, polymeric material(s), or the like. Stem inserts 502 and 502a may be color coded (e.g., black, red, orange) to indicate the type of valve or that the valve is a suction valve. In other embodiments, color for stem inserts 502 and 502a may be omitted or color coding may be provided by other means (e.g., painting).

Boot 508 (508a) may be formed from a suitable material, such as for example, polyurethane, polyurea, polyether (amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), or the like or combinations thereof.

In one embodiment, boot 508 (508a) may be made from a pliable material for ease of assembly e.g., a material that allows boot 508 (508a) to be slid over spring stanchion cup (not shown) during assembly and to seal off the suction in the circuit. In other embodiments, boot 508 (508a) may be over-molded onto the spring stanchion cup. Spring 506 (506a) may be formed from a suitable material, such as corrosion resistant metal, polyurethane, polyurea, polyether (amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic, or the like or combinations thereof. It will be understood that any resilient member (e.g., a member that resumes its original shape or position after being compressed) can be used for spring 506 (506a). A resilient member can include, for example, a spring, plastic, rubber or other elastic member that allows its original shape or position after being compressed.

FIGS. 1B-4B also illustrate lubricant 1000 which may be disposed on valve 500 and at least on stem 504. In some embodiments, lubricant 1000 also contains an antimicrobial agent.

In contrast, the stem of a re-usable suction valve may be formed from one or more components made of a material that is suitable for repeated cleaning, disinfection, and sterilization, such as stainless steel or the like. While this material allows a re-usable suction valve to be repeatedly cleaned, disinfected, and sterilized for re-use, such material may be costly. It is difficult to properly clean, requires more components, requires additional manufacturing and assembly steps, requires costlier manufacturing processes, and the like. In addition to being costlier to manufacture than a disposable suction valve, a re-usable suction valve also requires equipment and materials that are utilized to repeatedly clean, disinfect, and sterilize the valve.

FIG. 11B and FIG. 12B show views of illustrative embodiments of suction valve stems 504 and 504a illustrating grooves or recesses 510 (510a), 512 (512a), 524 (524a), gaskets 520 (520a) and 522 (522a), a transverse opening 514 (514a) and protrusion 532 (532a). Stem 504 (504a) also contains surface 530 (530a), meant for enhancing contact with an endoscope. Protrusions 532 and 532a are illustrated in FIGS. 11C, 11D, 12C and 12D.

FIGS. 11B and 12B are views of stems 504 and 504a. FIGS. 11C and 12C are top views of stems 504 and 504a, respectively, taken at the proximal end. FIGS. 11D and 12D are bottom views taken at the distal end of stems 504 and 504a, respectively. FIGS. 11E and 12E are cross sectional view along BB plane of FIGS. 11D and 12D, respectively. FIGS. 11F and 12F show detail C of gaskets 520 (520a) and 522 (522a) illustrated in FIGS. 11E and 12E. Found at the distal end of stems 504 and 504a, gaskets 520 (520a) and 522 (522a) can be made from polycarbonate or elastomer. Gaskets 520 (520a) and 522 (522a) provide dual seals, a design which provides more efficient suction, prevents leakage, and eliminates cross sectional clogging. Generally, protrusions 532 and 532a provide better alignment with an endoscope, in particular a FujiFilm™ endoscope.

Figure 13A:
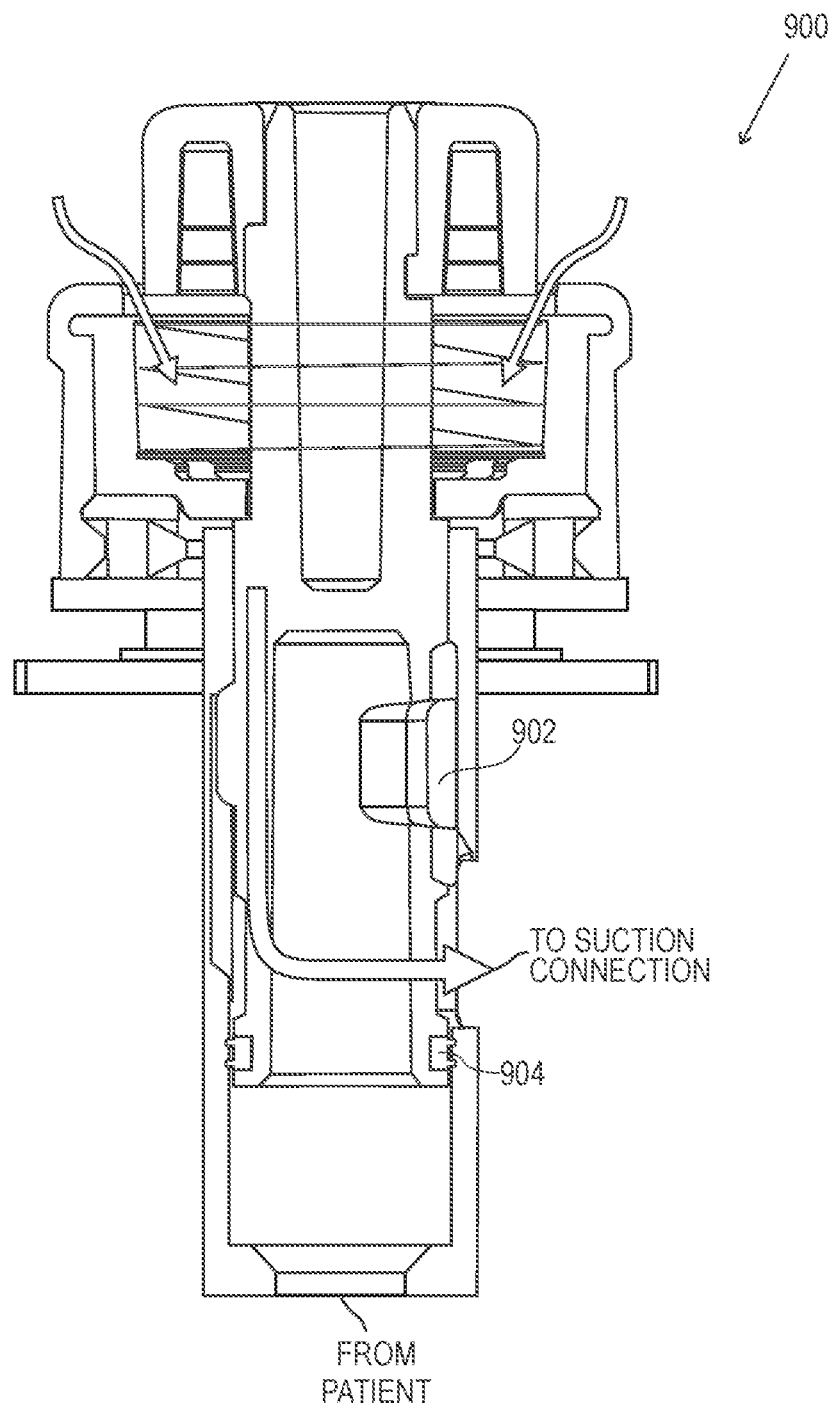
FIGS. 13A and 13B illustrate embodiments of the general operation of a disposable suction valve in a medical instrument, such as for example, an endoscope.
Figure 13B:
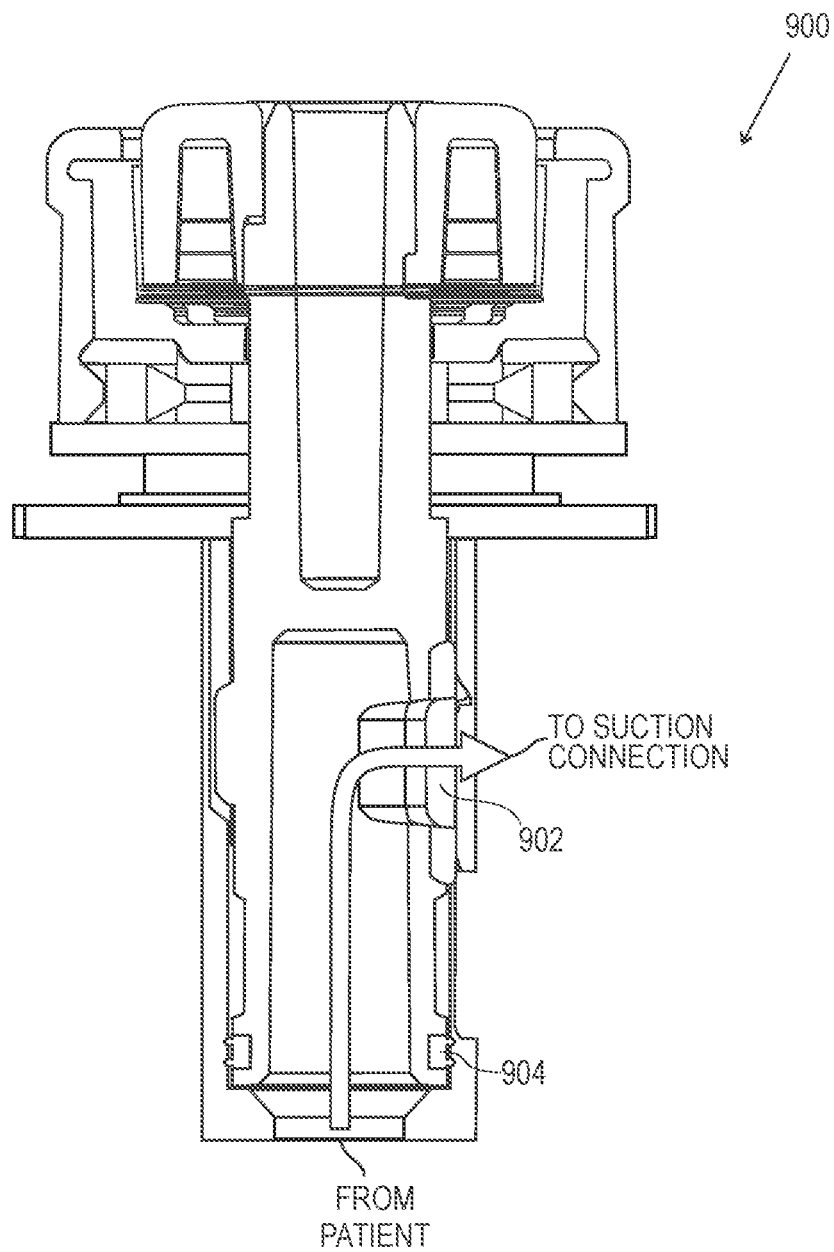

FIGS. 13A and 13B are illustrative embodiments of the general operation of a disposable suction valve 900 in an endoscope. Disposable suction valve 900 may be placed into the suction cylinder of an endoscope. The suction channel of the endoscope is linked to the instrument channel and leads to the distal end of an endoscope or leads toward the patient. The endoscope may be connected to a suction pump or the like to create negative pressure in the suction channel when a suction valve is actuated. The disposable suction valve has a first opening that is disposed at the distal end of the valve along a longitudinal axis of the central bore. The valve has a second opening 902 disposed near the middle of the valve and at the top of an internal channel of the valve. The second opening 902 is transverse to the longitudinal axis along the central bore. The second opening 902 is surrounded by a layer of sealing ledge providing support to opening and which prevents unwanted suction to other portions of the valve. In an un-actuated position shown in FIG. 13A, the second opening 902 is out of position with the suction channel, thereby preventing the suction pump from creating negative pressure in the suction channel. Suction valve 900 has not created a seal against surface 904 in an un-actuated position, which may allow air to enter through suction cylinder/port of the endoscope through suction valve 900. The disposable suction valve 900 also has a spring, a cap, and a stem. Spring surrounding a portion of stem is disposed below the cap.

For example, when spring 506 is not compressed, disposable suction valve 900 may allow air to enter through suction valve 900. Note that stem 504 does not create a seal against spring cup/stanchion 600, and stem 504 does not create a seal against the cylinder wall of the suction cylinder of the endoscope in the non-actuated position. When an operator actuates disposable suction valve 900 (e.g. depressing stem 504 and compressing spring 506), opening 902 moves into position with the suction channel from the distal end of the endoscope or from the patient as shown in FIG. 13B. Further, disposable suction valve 900 creates a seal between the stem 504 and surface 904 when actuated.

By aligning opening 902 with the suction pathway to the suction connection and sealing the suction cylinder of the endoscope, the negative pressure created by a suction pump or the like cause flow from the distal end of the endoscope towards the suction connection as shown in FIG. 13B. As a result, air and/or fluid may be suctioned from the distal end of the endoscope when disposable suction valve 900 is in an actuated position. When the operator releases the suction valve, spring 506 causes disposable suction valve 900 to return to the un-actuated position shown in FIG. 13A.

This procedure of aligning opening 902 with the suction pathway to the suction connection and sealing the suction cylinder of the endoscope, and the negative pressure created by a suction pump or the like causing flow from the distal end of the endoscope towards the suction connection as shown in FIG. 13B, can be accomplished with various suction valves and/or components, for example, those valve stems described in FIGS. 11A and 12A. As a result, air and/or fluid may be suctioned from the distal end of the endoscope when disposable suction valve 900 is in an actuated position. When the operator releases the stem 504 of the suction valve 900, spring 506 causes disposable suction valve 900 to return to the un-actuated position shown in FIG. 13A.

Although the suction valve is designed to be used with an endoscope, it will be understood that other medical instruments can be used with the present suction valve or assembly. These instruments include, for example, colonoscopes, laparoscopes, bronchoscopes, or any medical instrument with a camera that requires suctioning.

In some embodiments, there is a method for manufacturing a disposable suction valve comprising: molding a stem; molding a flange for a resilient member; placing a top end of the stem through the center of the resilient member; placing the bottom end of the stem through a stem opening in the flange for the resilient member; and placing tabs of the flange for the resilient member into recessed apertures of the stem.

In some embodiments, there is a disposable suction valve wherein the stanchion or flange is monolithic with the boot (e.g., they are one piece).

In some embodiments, there is a suction valve assembly comprising: a stem comprising a first opening disposed along a longitudinal axis of the stem, and a second opening disposed transverse to the first opening, the first and second openings for allowing passage of air and/or fluid; a flange for supporting a resilient member comprising at least one recess and/or projection configured to attach to the stem; the flange comprising an opening configured to receive the stem and allow movement of the stem in an upward and downward position and the resilient member configured to contact the flange and the stem, and/or the spring stanchion.

Figure 14:
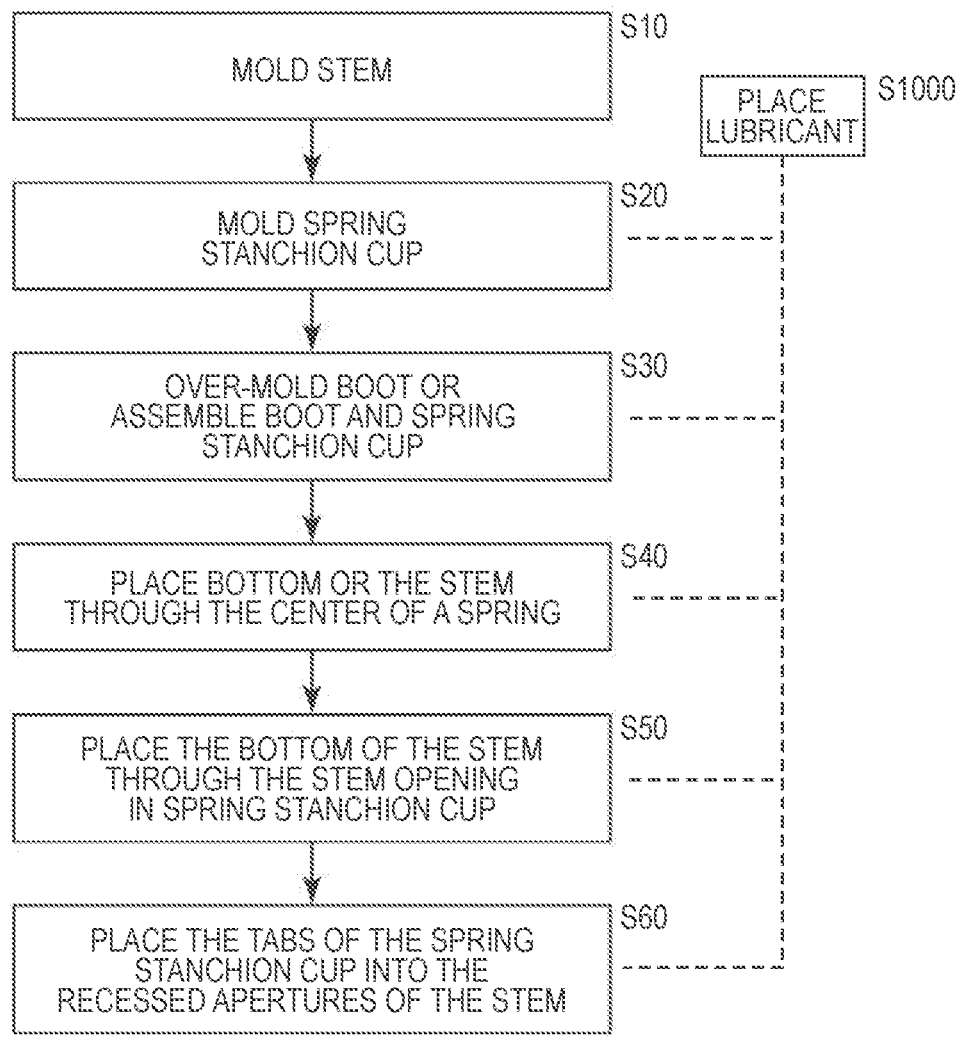
FIG. 14 illustrates a flow chart of an embodiment of a manufacturing process for a disposable suction valve, including placement of a lubricant on the valve.

FIG. 14 illustrates a flow chart of a manufacturing process for a disposable suction valve. In contrast to disposable suction valves, a re-usable suction valve may include metal components that are suitable for repeated cleaning, disinfection, and sterilization. These metal components may require costlier manufacturing and more complicated assembly than the components of a disposable suction valve. For example, metal components may be manufactured by precision machining/grinding, threading, stamping, machine pressing, or the like. Further, during assembly, the metal components may need to be welded together, glued using an adhesive, or the like. These steps may complicate manufacturing and increase cost.

A disposable suction valve provides a low-cost manufacturing and simplified assembly process, thereby significantly reducing the cost of the suction valve. The low-cost materials, manufacturing processes, and assembly process of disposable suction valves provides an alternative to utilizing a costly re-usable suction valve. Further, disposable suction valves allow the number of components to be reduced.

In step S10, a stem is molded using a suitable molding process, such as injection molding or the like. In step S20, a spring stanchion cup is molded using suitable thermoplastic processing techniques, such as, for example, injection molding, rotational molding, or the like, extrusion techniques (for example, extrusion, co-extrusion, multi-layer extrusion, and so forth) and casting.

The stem and spring stanchion cup are formed from a suitable material such as for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. The stem and spring stanchion cup may be formed from a rigid material that is capable of withstanding forces exerted on a suction valve by an operator.

In another embodiment of the manufacturing process, the stem and spring stanchion may be joined by ultrasonically welding molded pieces. A boot may be molded or assembled onto spring stanchion cup in step S30. The boot may be injection molded, over molded on the spring stanchion cup, or molded using any suitable molding process. When the boot is molded separately, the boot may also be assembled on the spring stanchion cup during step S30. The boot is formed from a suitable material or combination of material(s), such as rubber, plastic, polymeric material(s), or the like. In steps S40 and S50, the top of the stem is placed through the center of a spring and the stem opening in the spring stanchion cup. Next, spring stanchion cup tabs are placed into recess apertures of the stem in step S60 to complete the assembly of the disposable suction valve.

In other embodiments, once the valve assembly 500 is manufactured, in step S1000 a lubricant 1000 can be placed onto the valve by applying lubricant 1000 onto the main stem. In certain aspects, the lubricant comprises an antimicrobial agent, wherein (i) the main stem is color coded and the resilient member is a spring; (ii) the button cap is ultrasonically welded, glued, screwed, snap-fitted or otherwise attached to the stem; and/or (iii) the button cap centers the resilient member. In other aspects, the method of manufacturing the disposable valve assembly further comprises the step of placing the stanchion in a second mold, wherein a boot is over-molded onto the stanchion.

Spring Cup with Boot and Cap Snap for Air/Water and Suction Disposable Valves

Air/water and suction disposable valves 100 (500) of this disclosure can utilize the same spring cup with boot 104 (508). In addition, button cap 102 (501) can be snapped into both types of disposable valves 100 (500). Because these elements are applicable to both types of valves, this disclosure will use two numbers, the first applicable to the air/water valve and the second one to the suction valve.

Boot 104 (508) of FIG. 15A contains a stanchion ring 200 (600) in its interior and its exterior is bordered by a top rim 208 (708). Stanchion ring 200 (600) contains an outer ring (not shown) which provides an outside surface to hold boot 104 (508), a partition or diaphragm 204 (704), with a cutout opening 206a (706a) for receiving proximal end 135 (535) of stem 101 (504). While cutout opening 206a (706a) is shaped as a larger diameter circle with several peripheral cutouts 206b (706b) along the radius of the larger diameter circle, it should be recognized that any other suitably shaped cutout opening may be utilized (for example, square, triangle). Proximal end 135 (535) of stem 101 (504) may be placed through stanchion 200 (600) and resilient member 125 (506) (e.g., spring, rubber, elastic, not shown) and then it can be secured to button cap 102 (501) (not shown).

The outer diameter of proximal end 135 (535) of stem 101 (504) is smaller than a hollow center bore of button cap 102 (501), thereby allowing end 135 (535) of stem 101 (504) to be inserted into the center bore of button cap 102 (501). Proximal end 135 (535) may protrude slightly from button cap 102 (501) to provide an operator with tactile confirmation that the vent hole is sealed with the finger. Stem 101 (504) may be secured to button cap 102 (501) using ultrasonic welding, a suitable adhesive, mechanical attachment (for example, threading or the like) or any suitable attachment method.

In another implementation of the disposable air/water valve 100 or suction valve 500, boot 104 (508) and retaining ring 200 (600) may be molded as a single piece. In another implementation of the disposable air/water valve 100 or suction valve 500, stem 101 (504), and button cap 102 (501) may be molded as a single piece. In other implementations, boot 104 (508) may be molded separately from retaining ring 200 (600) and placed on the retaining ring 200 (600) during assembly.

Figure 15B:
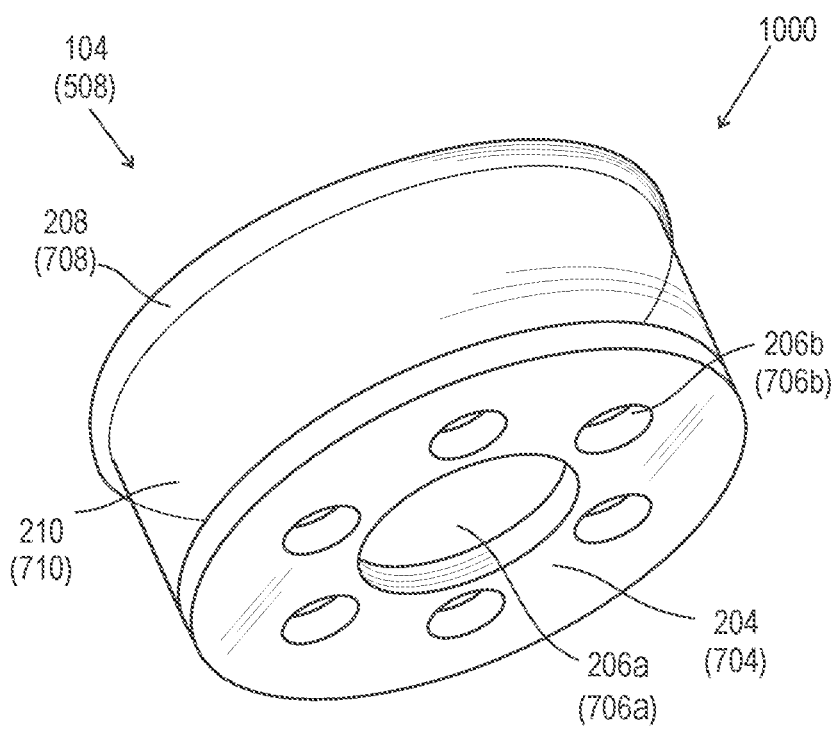
FIG. 15B illustrates a perspective view of another embodiment of a boot for use with a disposable air/water or a disposable suction valve in endoscopes.
Figure 16A:
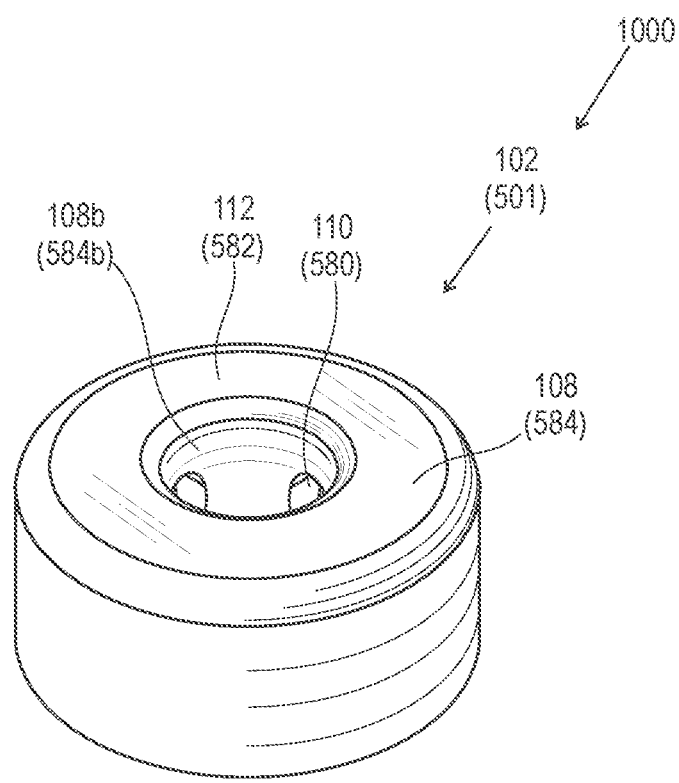
FIG. 16A illustrates a perspective view of an embodiment of a cap snap for use with a disposable air/water or a disposable suction valve.
Figure 16H:
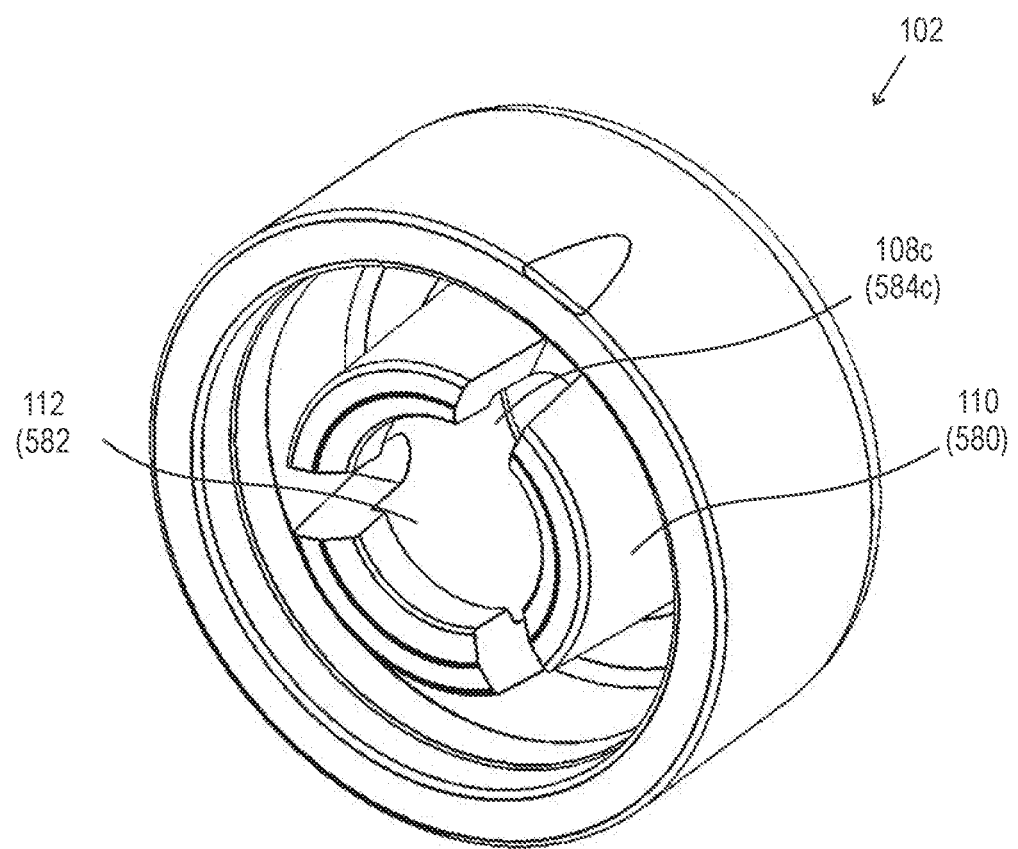

FIG. 15B is a perspective view of the stanchion ring 200 (600). Stanchion ring 200 (600) comprises a top rim 208 (708), and an outer ring 210 (710) which provides a surface to hold boot 104 (508). Stanchion ring 200 (600) also comprises a cutout opening 206a (706a) with several peripheral cutouts 206b (706b) around the radius of the cutout opening 206a (706a). It should be recognized that any other suitably shaped cutout opening 206a (706a) may be utilized (e.g. square, triangle and the like). Stanchion ring 200 (600) also includes diaphragm(s) 204 (704) positioned among cutout opening 206a (706a) and peripheral cutouts 206b (706b). The diaphragm(s) 204 (704) provide partitions to the cutouts and a surface to support spring 125 (506). The shapes of the diaphragms 204 (704) can vary depending on the shapes of cutout opening 206a (706a). The shapes of the cutouts and diaphragms affect the laminar flow of the air and the water. In another embodiment, the cutout opening 206a (706a) is a circle and the peripheral cutouts 206b (706b) are also circles with diaphragms in the shape of an arc.

In some applications, boot 104 (508) may also be made from a pliable material for ease of assembly e.g., a material that allows boot 104 (508) to be slid over retaining ring 200 (600). Retaining ring 200 (600), stem 101 (504), and button cap 102 (501) are formed from a suitable material or combination of material(s), such as plastic, polymeric material(s), polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or combinations thereof. In some other implementations, boot 104 (508) is overmolded onto the stanchion ring 200 (600). In other embodiments, boot 104 (508) is monolithic with stanchion cup 200 (600).

FIG. 15C is a front view of boot 104 (508). FIG. 15D is a cross-sectional view along EE plane of FIG. 15C illustrating the boot 104 (508) and stanchion 200 (600). FIG. 15E is a top view of boot 104 (508) illustrating top rim 208 (708) of boot, and cutout opening 206a (706a), peripheral cutouts 206b (706b) and diaphragm 204 (704) of stanchion.

FIG. 16A is a perspective view of button cap 102 (501) that can be snapped onto stem 101 (504) to engage stanchion 200 (600) of either disposable air/water valve 100 or disposable suction valve 500 for use in endoscopes. In some embodiments, button cap 102 (501) can be applied onto stem 101 (504) using a suitable adhesive, ultrasonic welding, threaded connection, or press fit.

FIG. 16C is a cross-sectional view along AA plane of FIG. 16B and illustrates projections 110 (580) and 112 (582) which facilitate snapping onto boot 104 (508). FIG. 16D is an enlarged view of detail C of FIG. 16C. In some implementations, button cap 102 (501) has a surface 108 (584) configured to form an annular shape 108a (584a) with the outer perimeter of button cap 102 (501) and gap 108c (584c). The annular shape 108a (584a) has a hollow center 108b (584b) where projections 110 (580) and 112 (582) are positioned. In some implementations, projections 110 (580) and 112 (582) are configured to receive stem insert 105 (502), (FIGS. 2A, 2B), applicable to either a disposable air/water valve or a suction valve. In some embodiments, stem insert 105 (502) may be formed from a suitable material or combination of material(s), such as plastic, polymeric material(s), or the like. Stem insert 105 (502) may be color coded (e.g., black, red, orange) to indicate the type of valve. In other embodiments, stem insert 105 (502) may be omitted or color coding may be provided by another means (e.g., painting).

In other implementations, boot 104 (508) may be molded separately from stanchion 200 (600) and placed on the stanchion 200 during assembly. Stem 101 (504) may be color coded or color matched by forming stem 101 (504) from a colored material, painting, or the like. The color coding of disposable air/water valve 100 or suction valve 500 is easily visible when the valve is out of an endoscope, thereby making air/water valve 100 or suction valve 500 easy to identify as a disposable air/water or suction valve in contrast to a non-disposable air/water or suction valve. Further, the color coding eliminates the need for separate color components necessary to produce an air/water or suction valve. Because stem 101 (504) is inserted into the center bore of button cap 102 (501), the color coding of stem 101 (504) is also visible from the top of button cap 102 (501) or when disposable air/water valve 100 or suction valve 500 is placed in the cylinder of an endoscope.

The outside diameter of the top end of button cap 102 (501) is larger than the diameter of resilient member (e.g., spring, rubber, elastic, etc.) 125 (506), which resumes its original shape or position after being compressed, and the inside diameter of cutout opening 206a (706a) in diaphragm 204 (704) is smaller than the diameter of resilient member (e.g., spring, rubber, elastic, etc.) 125 (506) to retain resilient member (e.g., spring, rubber, elastic, etc.) 125 (506) between stanchion 200 (600) and button cap 102 (501).

When button cap 102 is depressed by an operator, resilient member (e.g., spring, rubber, elastic, etc.) 125 is compressed causing button cap 102 to move towards stanchion 200. Because stem 101 is secured to button cap 102, it also moves when button cap 102 is depressed, thereby allowing the trumpet-like valve to move into alignment with a desired endoscope port. When the operator releases button cap 102, resilient member (e.g., spring, rubber, elastic, etc.) 125 forces button cap 102 away from stanchion 200, which causes stanchion 200 to move along stem 101. However, the cutout opening 206a in diaphragm 204 of stanchion 200 is smaller than the diameter of stem 101 just above seal retaining region 133, thereby preventing stanchion 200 from advancing past seal retaining region 133 on stem 101.

Gaskets 164 to 178 are formed from pliable material suitable for creating a seal, such as rubber, polymeric material(s), or a suitable material or a combination of suitable material(s). Boot 104 may also be made from a pliable material for ease of assembly e.g., a material that allows boot 104 to be slid over stanchion 200 (600). Stanchion 200 (600), stem 101 (504), and button cap 102 (501) are formed from a suitable material or combination of material(s), such as plastic, polymeric material(s), or the like. However, stanchion 200 (600), stem 101 (504), and button cap 102 (501) can be formed of a more rigid material than gaskets or seals 164-178 and boot 104 (508). It may be preferable to have a more rigid stanchion 200 (600), stem 101 (504), and button cap 102 (501) because they are subjected to forces exerted by resilient member (e.g., spring, rubber, elastic, etc.) 125 (506), an operator, or the like.

It will be recognized by one of ordinary skill in the art that numerous steps in the manufacturing process may be optional or may be performed in a different sequence than specifically shown. The scope of the manufacturing process is not limited to the particular sequence and steps discussed herein, except as expressly recited in the claims.

All the valves described in this disclosure are disposable, but may be sterilizable before single use. In various embodiments, one or more components of these valves are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In some embodiments, gamma radiation is used in the terminal sterilization step, which involves utilizing ionizing energy from gamma rays that penetrate deeply into the device. Gamma rays are highly effective in killing microorganisms; they leave no residues nor have sufficient energy to impart radioactivity to the device. Gamma rays can be employed when the device is in the package and gamma sterilization does not require high pressures or vacuum conditions; thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

In some embodiments, gas sterilization is used to sterilize one or more components of the device. The gas sterilization can be with ethylene oxide or steam sterilization.

In various embodiments, a kit is provided that may include additional parts along with each valve described in this disclosure, combined together to be used with the respective valve. For example, the kit may include the air/water, suction or a biopsy valve device in a first compartment. The second compartment may include a canister holding the air/water, suction or biopsy valve and any other instruments needed for the procedure. A third compartment may include a lubricant with or without an antimicrobial agent, gloves, drapes, wound dressings and other procedural supplies for maintaining sterility, as well as an instruction booklet. A fourth compartment may include additional cannulas and/or needles. A fifth compartment may include an agent for radiographic imaging. Each device may be separately packaged in a plastic pouch that is radiation sterilized. A cover of the kit may include illustrations of the use of the device and a clear plastic cover may be placed over the compartments to maintain sterility.

Lubricants

Oftentimes, disposable valve assemblies for use with an endoscope, develop leaks between the endoscope valve ports and the valve because the fit is not sufficiently tight. Lubricants covering a disposable valve assembly and, in particular, the portion of the valve assembly that sits in an endoscope port can prevent air or water leaks and provide a tight fit. In some embodiments, useful lubricants that can be used with the disposable valve assemblies discussed in this disclosure comprise silicone-based lubricants, non-silicone-based lubricants and/or a combination thereof.

In some embodiments, lubricant 1000 comprises an oil lubricant. The oil lubricant can be polydimethyl siloxane, polytrifluoropropylmethyl siloxane, or a copolymer of dimethylsiloxane and trifluoropropylmethylsiloxane. The viscosity of the oil lubricant can be from about 20 cp to about 1,000,000 cp. In some embodiments, a solvent is added to the oil lubricant with very high viscosity to facilitate application of the antimicrobial lubricant onto the disposable valve assemblies for use with an endoscope described in this disclosure.

For example, silicone-based lubricants comprise Dow Corning medical fluid. Other silicone-based lubricants can include other components, for example, diisopropyl adipate, purcellin oil, glycerol tribehenate, silicone oil, a surfactant, sorbitan monooleate, and sorbitan trioleate.

A suitable lubricant is a silicone oil or a mixture thereof having a molecular weight of about 20,000 to 60,000, preferably about 35,000 to 45,000. In certain embodiments, lubricants are polydialkylsiloxanes of general structure I:

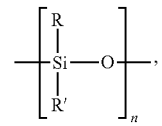

wherein each of R and R' may be independently a lower alkyl of 1 to 20 carbon atoms, preferably 1 to 8 carbon atoms, or may be joined into a silicone containing ring of 5 to 8 carbon atoms, and n may be an integer from 1 to 2000, in some embodiments, 1 to 800. In other embodiments, the lubricants of structure I have viscosities from about 10 to 1,000,000, in yet other embodiments, about 100 to 20,000 centistokes. In one embodiment, the lubricant is Dow Corning DC-360® silicone oil of 12,500 centistokes viscosity.

In other embodiments, another useful formulation of the silicone oil solution for the disposable valve assemblies described in this disclosure uses approximately 1500 to 3500 grams, preferably between about 2000 to 2,500 grams, of volatile solvent methylsiloxane (available as Dow Corning® OS-10) in combination with approximately 150 to 400 grams, preferably between about 200 to 300 grams, of a not as volatile solvent solution that contains about 30% polydimethylsiloxane copolymers dispersed in xylene (sold under the trade name MED-4162 by the NuSil Technology Company). The OS-10 solvent and the MED-4162 solvent solution are combined by a spinning or mixing process using any one of a number of conventional mixing machines known in the field. For this formulation, the spinning or mixing process continues for a given time period, for example from a minimum of 10 minutes to about 30 minutes. In one particular practice of this formulation, an acceptable silicone oil solution was made by spinning or mixing about 2,262 grams of OS-10 with about 250 grams of MED-4162 for approximately 10 minutes.

In some embodiments, the disposable valve assemblies described in this disclosure may be dipped into a solvent solution of chlorhexidine and a silicone lubricant whereby a layer of chlorhexidine and lubricant is applied to the surface of the article. An effective coating of chlorhexidine may be obtained when the solvent solution contains from about 0.02 to 5%, in other embodiments, from about 0.1 to 3.0% of chlorhexidine and from about 0.1 to about 8%, or in yet other embodiments, from about 1% to 4% (w/v) of silicone.

In other embodiments, non-silicone-based lubricants include, without limitation, a water soluble lubricant, an insoluble lubricant, a viscous gel lubricant, a solid lubricant or a combination thereof. Water soluble lubricants include, without limitation, polyethylene oxide, polyvinylpyrrolidone, polyvinyl alcohol, and derivatives thereof.

In some embodiments, lubricant 1000 comprises at least one of a water soluble lubricant, an insoluble lubricant, a viscous gel lubricant, a solid lubricant and a shapeable lubricant.

Lubricant 1000 with or without an antimicrobial agent may be applied to outer surface of disposable valve assemblies 100, and 500 as illustrated in FIGS. 5A, 5B, 5C, 5D, 6A, 6B, 6C, 6D, 7A, 7B, 7C, 7D, 11A, 11B, 12A, 12B, 15A, 15B and 16A by dipping, brushing, spraying, or any other compatible techniques known to one of skill in the art.

In some embodiments, the layer of lubricant 1000 on the disposable valve assemblies described in this disclosure is uniform and can, for example, have a thickness of from about one micrometer to about five micrometers.

In various embodiments, lubricant 1000 generally comprises an antimicrobial or biocidal agent effective against various forms and strains of bacteria which may cause infection within a patient. The terms "biocidal agent" or "biocide," as used herein refer to an agent that destroys, inhibits and/or prevents the propagation, growth, colonization and multiplication of unwanted organisms. The term "organism" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Specific examples of such organisms include the fungi *Aspergillus niger, Aspergillus flavus, Rhizopus nigricans, Cladosprorium herbarium, Epidermophyton floccosum, Trichophyton mentagrophytes, Histoplasma capsulatum*, and the like; bacteria such as *Pseudomanas aeruginosa, Escherichia coli, Proteus vulgaris, Staphylococcus aureus, Staphylococcus epidermis, Streptococcus faecalis, Klebsiella, Enterobacter aewgenes, Proteus mirabilis*, other gram-negative bacteria and other gram-positive bacteria, mycobactin and the like; and yeast such as *Saccharomcyces cerevisiae, Candida albicans*, and the like. Additionally, spores of microorganisms, viruses and the like are organisms within the scope of the present disclosure.

Antimicrobial or biocide agents suitable for use in the present invention include, but are not limited to phenol, quaternary ammonium, guanidine, taurolidine, parachlorometaxylenol, silver sulfadiazine, silver oxide, silver nitrate, pyridinium, benzalkonium chloride, cetrimide, benethonium chloride, cetylpyridinium chloride, dequalinium acetate, dequalinium chloride, and chloroxylenol. Further, in some embodiments lubricant 1000 comprises a microbial agent selected from chlorhexidine base, chlorhexidine gluconate, chlorhexidine acetate, chlorhexidine hydrochloride, chlorhexidine dihydrochloride, dibromopropamidine, halogenated diphenylalkanes, carbanilide, salicylanilide, tetrachlorosalicylanilide, trichlorocarbanilide, and mixtures thereof. Still further, in some embodiments lubricant 1000 comprises a microbial agent selected from chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride, and combinations thereof. The antimicrobial agent can be solid particles that are insoluble in the lubricant or in liquid form. The antimicrobial agent is well mixed within a lubricant prior to application to the disposable valve assembly.

In some embodiments, lubricant 1000 comprises one or more antimicrobial agents in an amount from about 0.01, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5% (w/v) to about 10.0% (w/v) of lubricant 1000. In other embodiments, lubricant 1000 comprises one or more antimicrobial agents in an amount from about 0.001, 0.0015, 0.0020, 0.0025, 0.0030, 0.0035, 0.0040, 0.0045, 0.0050, 0.0055, 0.0060, 0.0065, 0.0070, 0.0075, 0.0080, 0.0085, 0.0090, 0.0095, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5% (w/v) to about 5.0% (w/v) of lubricant 1000. Further, in some embodiments lubricant 1000 comprises one or more antimicrobial agents in an amount from about 0.01% to about 10.0% (w/v).

In some embodiments, lubricant 1000 further comprises one or more fugitive solvents, such as tetrahydrofuran (THF), methylethylketone (MEK) and hexane solvents. In some embodiments, lubricant 1000 comprises a fugitive solvent in an amount about equal to 70% (w/v) of lubricant 1000. In other embodiments, lubricant 1000 comprises two or more fugitive solvents.

In other embodiments, lubricant 1000 comprises one or more alcohol components. Suitable alcohol components generally include a lower alcohol having between one and six carbons ($C_1$-$C_6$). In some embodiments, lubricant 1000 comprises an alcohol component selected from the group consisting of ethyl alcohol, isopropanol, propanol, and butanol. In other embodiments, lubricant 1000 comprises two or more lower alcohol components, for example a mixture of isopropyl alcohol and ethyl alcohol in a ratio of about 1:10 to about 1:1. Further, in some embodiments lubricant 1000 comprises a mixture of more than two alcohol components.

In some embodiments, lubricant 1000 comprises an alcohol component in an amount about equal to 40% (w/v) of lubricant 1000. In other embodiments, lubricant 1000 comprises an alcohol component in an amount from about 20%, 25%, 30%, 35%, 40%, 45%, 50%, 55%, 60%, 65% 70%, 75%, 80%, 85%, 90% (w/v) to about 95% (w/v). In yet other embodiments, antimicrobial lubricant 1000 further comprises a lubricant, such as silicone oil.

In various embodiments, non-silicone lubricants useful to cover the valves described in this disclosure include hydrophilic polymer coatings, Teflon (PTFE) lubricants and coatings, thermoplastic coatings, cyanoacrylate coatings, Parylene coatings, plasma surface treatments, cornstarch powder coatings liquid soaps, Astroglide lubricants, mineral oil, glycerin, alcohol, saline, Krytox lubricants, molybdenum disulfide lubricants and graphite.

Antimicrobial Agents

It has been unexpectedly found that the application of lubricant containing an antimicrobial agent to the surface or a portion of the disposable valve assemblies for use with an endoscope described in this disclosure can prevent or substantially eliminate the growth of harmful bacteria, fungi and the like present or growing in the colon or any other body part accessible during an endoscopic procedure. In particular, activating the lens-rinsing function can distribute the antimicrobial agent by itself or contained in a lubricant along the endoscope channel, along the lens and has the ability of destroying harmful bacteria and/or fungi that may form in the endoscope channel, the lens and other ancillary components of the endoscope, for example the disposable valve assemblies.

Referring to the disposable valve assemblies described in this disclosure, an antimicrobial agent by itself or with a lubricant can be applied to any component of the disposable valve assembly. For example, it can be part of the material of the disposable valve, or applied to the disposable valve assembly by hand or machine spraying or coating. In particular, the antimicrobial agent can be applied to the stem, the spring stanchion and/or the spring.

In various embodiments, the antimicrobial agent useful for this disclosure comprises, essentially consists of or consists of an antibiotic, an antiviral agent, an antifungal agent, an antiseptic, a disinfectant or combination thereof. In some embodiments of this disclosure, the lubricant comprises an antimicrobial agent. In other embodiments, the thermoplastic material comprises the antimicrobial agent and in yet other embodiments, the thermoplastic material has an antimicrobial agent coated thereon. In various embodiments, the antimicrobial agent is an antibacterial agent. While any antibacterial agent may be used with lubricants, the thermoplastic material or coatings covering the thermoplastic material, some non-limiting exemplary antibacterial agent(s) include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymyxins, lipopeptide antibiotics, as well as pharmacologically acceptable sodium salts, pharmacologically acceptable calcium salts, pharmacologically acceptable potassium salts, lipid formulations, derivatives and/or analogs of the above.

Each of these classes of antibacterial agents have different mechanisms of action and are represented by several antibiotics, a discussion of which is presented below. However, the skilled artisan will recognize that the invention is in no way limited to the agents set forth here and that these agents are described merely as examples.

The aminoglycosides are bactericidal antibiotics that bind to the 30S ribosome and inhibit bacterial protein synthesis. They are typically active against aerobic gram-negative bacilli and staphylococci. Exemplary aminoglycosides that may be used in some specific aspects of the invention include amikacin, kanamycin, gentamicin, tobramycin, or netilmicin.

Beta lactams are a class of antibacterials that inhibit bacterial cell wall synthesis. A majority of the clinically useful beta-lactams belong to either the penicillin group (penam) or cephalosporin (cephem) groups. The beta-lactams also include the carbapenems (e.g., imipenem), and monobactams (e.g., aztreonam). Inhibitors of beta-lactamase such as clavulanic acid and its derivatives are also included in this category.

Non-limiting examples of the penicillin group of antibiotics that may be used in the solutions of the present invention include amoxicillin, ampicillin, benzathine penicillin G, carbenicillin, cloxacillin, dicloxacillin, piperacillin, or ticarcillin. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan. Other examples of beta lactams include mipenem or meropenem which are extremely active parenteral antibiotics with a spectrum against almost all gram-positive and gram-negative organisms, both aerobic and anaerobic and to which *Enterococci, B. fragilis,* and *P. aeruginosa* are particularly susceptible.

Examples of beta lactamase inhibitors include clavulanate, sulbactam, or tazobactam. In some aspects of the present invention, the antibacterial solutions may comprise a combination of at least one beta lactam and at least one beta lactamase inhibitor.

Macrolide antibiotics are another class of bacteriostatic agents that bind to the 50S subunit of ribosomes and inhibit bacterial protein synthesis. These drugs are active against aerobic and anaerobic gram-positive cocci, with the exception of *enterococci*, and against gram-negative anaerobes. Exemplary macrolides include erythromycin, azithromycin, clarithromycin.

Quinolones and fluoroquinolones typically function by their ability to inhibit the activity of DNA gyrase. Examples include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin.

Sulfonamides are synthetic bacteriostatic antibiotics with a wide spectrum against most gram-positive and many gram-negative organisms. These drugs inhibit multiplication of bacteria by acting as competitive inhibitors of p-aminobenzoic acid in the folic acid metabolism cycle. Examples include mafenide, sulfisoxazole, sulfamethoxazole, and sulfadiazine.

The tetracycline group of antibiotics include tetracycline derivatives such as tigecycline, minocycline, doxycycline or demeclocycline and analogs such as anhydrotetracycline, chlorotetracycline, or epioxytetracycline. The present inventors have previously shown that minocycline has a higher penetration of the microbial biofilm layer than vancomycin and that EDTA is unique in effectively preventing and dissolving polysaccharide-rich microbial glycocalyx.

The streptogramin class of antibacterial agents is exemplified by quinupristin, dalfopristin or the combination of two streptogramins. Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin.

Other antibacterial drugs are glycopeptides such as vancomycin, teicoplanin and derivatives thereof. Yet other antibacterial drugs are the polymyxins which are exemplified by colistin.

In addition to these, several other antibacterial agents such as prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, ketolide etc. may be used in preparing the compositions described herein. Of these, metronidazole is active only against protozoa, such as *Giardia lamblia, Entamoeba histolytica* and *Trichomonas vaginalis*, and strictly anaerobic bacteria. Spectinomycin, is a bacteriostatic antibiotic that binds to the 30S subunit of the ribosome, thus inhibiting bacterial protein synthesis and nitrofurantoin is used orally for the treatment or prophylaxis of UTI as it is active against *Escherichia coli, Klebsiella-Enterobacter* species, staphylococci, and *enterococci*.

In other embodiments, the antimicrobial agent is an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole, posaconazole, ravuconazole or flutrimazole; the polyene antifungals such as amphotericin B, liposomal amphoterecin B, natamycin, nystatin and nystatin lipid formulation; the cell wall active cyclic lipopeptide antifungals, including the echinocandins such as caspofungin, micafungin, anidulfungin, cilofungin; LY121019;

LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other embodiments of the invention, the antimicrobial agent is an antiviral agent. Non-limiting examples of antiviral agents include cidofovir, amantadine, rimantadine, acyclovir, gancyclovir, pencyclovir, famciclovir, foscarnet, ribavirin, or valcyclovir. In some embodiments the antimicrobial agent is an innate immune peptide or proteins. Some exemplary classes of innate peptides or proteins are transferrins, lactoferrins, defensins, phospholipases, lysozyme, cathelicidins, serprocidins, bactericidal permeability increasing proteins, amphipathic alpha helical peptides, and other synthetic antimicrobial proteins.

In other embodiments of the invention, the antimicrobial agent is an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5, 7-triazo 1-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate. In some embodiments, a useful antiseptic that can be used with the disposable valve assemblies configured for use with an endoscope include silver halides, for example, silver iodide and silver chloride colloidal compositions. In some embodiments, some antiseptics contain silver in the presence of protein. For example, some mild silver protein antiseptics contain from about 19% to about 23% silver weight by weight. In some embodiments, Argyrol®, a mild protein antiseptic containing 30% silver weight by weight can be used with the disposable valve assemblies described in this disclosure. Other strong silver protein antiseptics contain from about 7.5% to about 8.5% silver weight by weight.

In some embodiments, a composition that includes an antiseptic agent may be applied to the surface by any method known to those of ordinary skill in the art. For example, if the surface is a surface of a disposable valve assembly as described in this disclosure, the disposable valve assembly may be immersed in the composition, or the composition may be painted or sprayed onto the device. In some embodiments, the coating composition may include a dye. The self-impregnating property of the dyes such as, for example, the triarylmethane dyes, removes the need for another binding agent.

For example, in one embodiment, one method of coating the disposable valve assembly first requires application or absorption of a layer of surfactant, such as tridodecylmethyl ammonium chloride (TDMAC) followed by the antibiotic coating layer, to the surface of the disposable valve assembly. Another method used to coat surfaces of the disposable valve assembly with antibiotics involves first coating the selected surfaces with benzalkonium chloride followed by ionic bonding of the antibiotic composition (Solomon and Sherertz, 1987; U.S. Pat. No. 4,442,133). Other methods of coating surfaces of medical devices with antibiotics are taught in U.S. Pat. No. 4,895,566 (a medical device substrate carrying a negatively charged group having a pH of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

In certain embodiments, antiseptic derivative compounds with broad-spectrum antiseptic activity against bacteria and fungi including nosocomial and multidrug-resistant varieties may be used to impregnate, bind, coat, adhere and/or attach to various device surfaces without the assistance of impregnating vehicles such as tridodecylmethylammonium chloride (TDMAC).

In some embodiments, one example of a broad-spectrum antiseptic is a composition that includes a combination of gentian violet and chlorhexidine ("Gendine"). Gentian violet, on its own, is a good impregnating triarylmethane dye. However, after impregnating the surfaces of various polymers, including polyvinylchloride, gentian violet on its own has no activity against *Pseudomonas aeruginosa*, which is the second most common cause of nosocomial pneumonia and the third most common cause of nosocomial urinary tract infections. Compositions with antiseptic properties that are specifically contemplated for use in this application include, but are not limited to Gendine, Genlenol and Genfoctol.

In some embodiments, the antimicrobial agent that can be used with the disposable valve assemblies described in this disclosure are present in an amount from at least 0.01% (w/v) to about 5.0%.

The above antimicrobials can be delivered in solvents. Non-limiting examples of a solvent as used herein may be an aqueous solvent or a nonaqueous solvent. In particular embodiments, the solvent is inert in that it has no ability to alter or modify the chemical structure of the antimicrobial agent. Nonlimiting examples of solvents include water, methylene chloride, alcohols (such as methanol and ethanol), ketones (such as acetone, methylethylketone), esters (such as tetrahydrofuran), aldehydes (such as formaldehyde), acetonitrile, acetic acid, chloroform, butyl acetate, or a combination thereof. In some embodiments, the solvent is a dipolar aprotic solvent, such as dimethylsulfoxide or N,N-dimethylformamide. The solvent may also be a protic solvent or an aprotic solvent.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. A disposable valve assembly configured for use with an endoscope, the disposable valve assembly comprising: a stem comprising a proximal end and a distal end and a first opening disposed along a longitudinal axis of the stem and extending from the proximal end to the distal end of the stem, the stem comprising a thermoplastic material and a second opening transverse to and intersecting with the first opening, the second opening of the stem extending through the stem; a spring stanchion comprising an opening configured to receive the stem, the spring stanchion and/or a spring configured to allow movement of the stem in an upward and downward direction relative to the proximal and/or distal end; and the spring configured to contact the spring stanchion, wherein the disposable valve assembly comprises an umbrella valve disposed adjacent to the distal end and the umbrella valve has a convex shape concaving downward toward the distal end of the stem.

2. The disposable valve assembly of claim 1, wherein the disposable valve assembly is used to control the flow of air and water to the endoscope.

3. The disposable valve assembly of claim 1, wherein a lubricant is disposed on the stem, spring stanchion and/or the spring.

4. The disposable valve assembly of claim 1, wherein the disposable valve assembly further comprises a cap, the cap configured to engage the stem.

5. The disposable valve assembly of claim 1, wherein the disposable valve assembly further comprises a cap having a fitting to snap fit with the stem.

6. The disposable valve assembly of claim 5, wherein the cap comprises a plurality of projections configured to receive a stem insert at one end and to snap fit onto the stem at the opposite end.

7. The disposable valve assembly of claim 1, wherein the disposable valve assembly further comprises a boot having a diameter greater than the spring stanchion and configured to engage the spring stanchion.

8. The disposable valve assembly of claim 1, wherein the second opening of the stem is adjacent to the distal end of the stem and extends through the stem.

9. The disposable valve assembly according to claim 1, wherein (i) the umbrella valve comprises an outer edge comprising an angled or chamfered edge; or (ii) the umbrella valve comprises an outer edge comprising a protrusion.

10. The disposable valve assembly of claim 9, wherein (i) the lubricant comprises silicone-based grease, non-silicone based grease, or a combination thereof; and/or (ii) the antimicrobial agent is an antibiotic, an antiseptic, an antiviral agent, an antifungal agent, a disinfectant or a combination thereof.

11. The disposable valve assembly according to claim 1, wherein (i) the thermoplastic material comprises an antimicrobial agent; and/or (ii) the thermoplastic material has an antimicrobial agent coated thereon.

12. A method for manufacturing a disposable air/water valve assembly configured for use with an endoscope, the method comprising: separately molding a valve stem, cap and spring stanchion, wherein the stem comprises a proximal end and a distal end and a first opening disposed along a longitudinal axis of the stem and extending from the proximal end to the distal end of the stem, the first opening facing the longitudinal direction at an end face of the distal end of the stem, the stem comprising a second opening transverse to and intersecting with the first opening, the second opening of the stem extending through the stem; placing the proximal end of the stem through a stem opening in the spring stanchion; placing the proximal end of the stem through the center of a spring; and attaching the cap onto the proximal end of the stem and securing with a stem insert, wherein the method further comprises disposing an umbrella valve adjacent to the distal end and the umbrella valve has a convex shape concaving downward toward the distal end of the stem.

13. The method of manufacturing of claim 12, wherein the method further comprises applying a lubricant onto the stem, spring and/or spring stanchion.

14. The method of manufacturing of claim 13, wherein the lubricant comprises a silicone-based grease, non-silicone based grease, or a combination thereof.

15. The method of manufacturing of claim 12, further comprising (i) over molding gaskets on the stem; or (ii) over molding a boot onto the spring stanchion.

16. The method of manufacturing of claim 12, wherein the stem comprises gaskets to assure an air-tight seal within a suction port or the stem.

17. The method of manufacturing of claim 12, wherein molding of the stem is in the presence of an antimicrobial agent.

18. The method of manufacturing of claim 17, wherein the antimicrobial agent is an antibiotic, an antiseptic, an antiviral agent, an antifungal agent, a disinfectant or a combination thereof.

19. The method of manufacturing of claim 12, wherein the cap is ultrasonically welded, press fit or otherwise attached to the stem.

* * * * *